(12) United States Patent
Kosuge et al.

(10) Patent No.: US 8,557,401 B2
(45) Date of Patent: Oct. 15, 2013

(54) CHRYSENE COMPOUND AND ORGANIC LIGHT-EMITTING DEVICE HAVING THE COMPOUND

(75) Inventors: Tetsuya Kosuge, Yokohama (JP); Jun Kamatani, Tokyo (JP); Yosuke Nishide, Kawasaki (JP); Kengo Kishino, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 182 days.

(21) Appl. No.: 13/146,315

(22) PCT Filed: Oct. 3, 2010

(86) PCT No.: PCT/JP2010/054472
§ 371 (c)(1),
(2), (4) Date: Jul. 26, 2011

(87) PCT Pub. No.: WO2010/107037
PCT Pub. Date: Sep. 23, 2010

(65) Prior Publication Data
US 2011/0279025 A1    Nov. 17, 2011

(30) Foreign Application Priority Data

Mar. 16, 2009 (JP) ................... 2009-063012
Oct. 13, 2009 (JP) ................... 2009-236435
Jan. 20, 2010 (JP) ................... 2010-010192

(51) Int. Cl.
| | | |
|---|---|---|
| H01L 51/54 | (2006.01) | |
| C07C 13/547 | (2006.01) | |
| C07C 211/57 | (2006.01) | |
| C07C 13/62 | (2006.01) | |
| C07C 13/573 | (2006.01) | |
| C07D 471/04 | (2006.01) | |
| C07F 15/00 | (2006.01) | |

(52) U.S. Cl.
USPC ........... 428/690; 428/917; 313/504; 313/506; 546/4; 546/88; 564/434; 585/26; 585/27

(58) Field of Classification Search
None
See application file for complete search history.

(56) References Cited

U.S. PATENT DOCUMENTS

| | | |
|---|---|---|
| 7,429,425 B2 | 9/2008 | Ikeda et al. |
| 8,026,664 B2 | 9/2011 | Saitoh et al. |

(Continued)

FOREIGN PATENT DOCUMENTS

| | | |
|---|---|---|
| CN | 1675149 A | 9/2005 |
| JP | 2004-75567 A | 3/2004 |

(Continued)

OTHER PUBLICATIONS

European Communication issued in counterpart application No. 10753529.6 dated Aug. 1, 2012—6 pages.

(Continued)

*Primary Examiner* — Dawn Garrett
(74) *Attorney, Agent, or Firm* — Fitzpatrick, Cella, Harper & Scinto

(57) ABSTRACT

To provide a novel chrysene compound and an organic light-emitting device having high emission efficiency and excellent driving durability, provided is a novel triaryl-substituted chrysene compound represented by the general formula [1]:

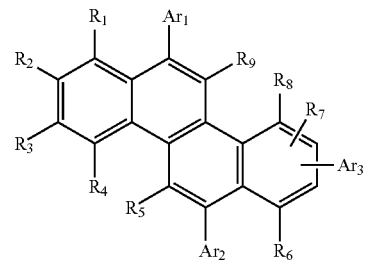

[1]

wherein $Ar_1$ to $Ar_3$ each represent a substituent selected from the group consisting of a substituted or unsubstituted naphthyl group, a substituted or unsubstituted phenanthryl group, and a substituted or unsubstituted fluorenyl group.

8 Claims, 1 Drawing Sheet

(56) References Cited

U.S. PATENT DOCUMENTS

| | | |
|---|---|---|
| 2004/0076853 A1* | 4/2004 | Jarikov .................. 428/690 |
| 2006/0134456 A1 | 6/2006 | Ikeda et al. |
| 2007/0230052 A1 | 10/2007 | Ajan et al. |
| 2008/0154040 A1 | 6/2008 | Kosuge et al. |
| 2009/0008605 A1 | 1/2009 | Kawamura et al. |
| 2009/0008606 A1 | 1/2009 | Kawamura et al. |
| 2009/0008607 A1 | 1/2009 | Kawamura et al. |
| 2009/0009065 A1 | 1/2009 | Nishimura et al. |
| 2009/0009066 A1 | 1/2009 | Nishimura et al. |
| 2009/0009067 A1 | 1/2009 | Nishimura et al. |
| 2009/0009073 A1 | 1/2009 | Ikeda et al. |
| 2009/0009074 A1 | 1/2009 | Ikeda et al. |
| 2009/0039317 A1 | 2/2009 | Kawamura et al. |
| 2009/0045730 A1 | 2/2009 | Nishimura et al. |
| 2009/0045731 A1 | 2/2009 | Nishimura et al. |
| 2009/0102371 A1 | 4/2009 | Hashimoto et al. |
| 2009/0200919 A1 | 8/2009 | Kamatani et al. |
| 2010/0194270 A1 | 8/2010 | Kawamura et al. |
| 2010/0219407 A1 | 9/2010 | Kamatani et al. |
| 2010/0327274 A1 | 12/2010 | Okajima et al. |
| 2011/0024737 A1 | 2/2011 | Horiuchi et al. |
| 2011/0108810 A1 | 5/2011 | Kishino |
| 2011/0272683 A1* | 11/2011 | Kosuge et al. .................. 257/40 |
| 2011/0315973 A1* | 12/2011 | Yamada et al. .................. 257/40 |

FOREIGN PATENT DOCUMENTS

| | | |
|---|---|---|
| JP | 2007-273055 A | 10/2007 |
| WO | 2009/008311 A1 | 1/2009 |
| WO | 2009/008354 A1 | 1/2009 |

OTHER PUBLICATIONS

U.S. Appl. No. 13/144,622, filed Jul. 14, 2011.
U.S. Appl. No. 13/254,907, filed Sep. 6, 2011.
Chinese Office Action issued in counterpart application No. 201080012238.6 dated Jun. 5, 2013, along with its English-language translation—16 pages.

* cited by examiner

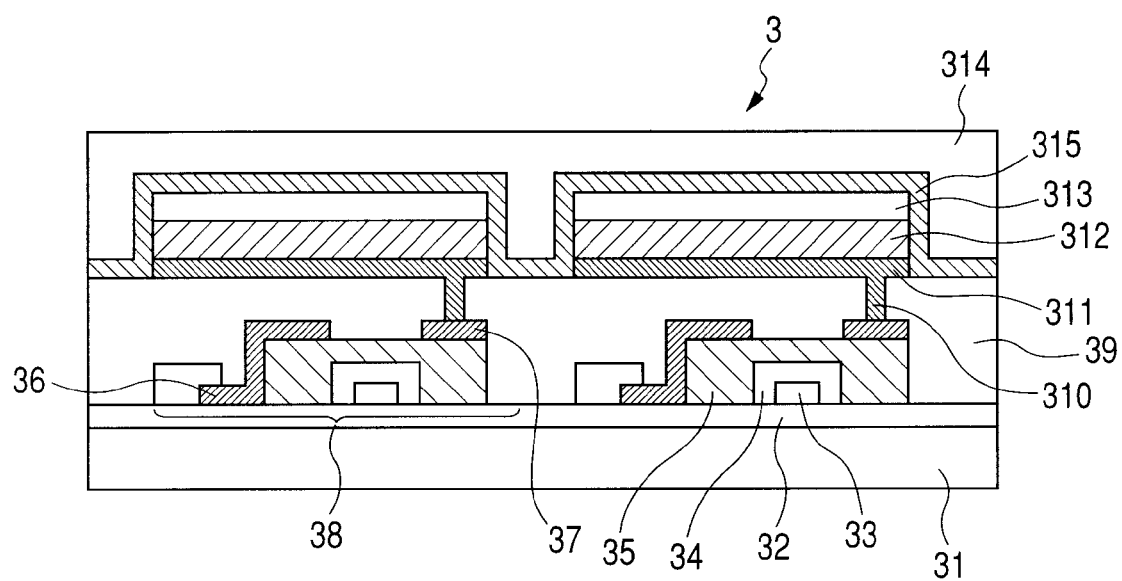

CHRYSENE COMPOUND AND ORGANIC LIGHT-EMITTING DEVICE HAVING THE COMPOUND

TECHNICAL FIELD

The present invention relates to a novel chrysene compound and an organic light-emitting device having the compound.

BACKGROUND ART

An organic light-emitting device is such a device that a thin film having a fluorescent organic compound or phosphorescent organic compound is interposed between an anode and a cathode serving as a pair of electrodes.

In addition, the emission efficiency and durability of the organic light-emitting device are susceptible to improvement.

A chrysene derivative has been known as one kind of fused polycyclic aromatic compound. Japanese Patent Application Laid-Open No. 2004-75567 discloses a 6,12-diaryl-substituted chrysene derivative. Japanese Patent Application Laid-Open No. 2007-273055 discloses a 3,6,9,12-tetraaryl-substituted chrysene derivative and Chem. Commun. 2008, 2319 discloses a 2,6,8,12-tetraaryl-substituted chrysene derivative. In addition, WO 2009/008311 discloses a 2,6,12-triphenyl-substituted chrysene derivative.

DISCLOSURE OF THE INVENTION

An object of the present invention is to provide a novel compound capable of sufficiently satisfying emission efficiency and durability. To be more specific, the object is to provide a novel chrysene compound and an organic light-emitting device having the compound.

According to the present invention, there is provided a chrysene compound represented by the following general formula [1].

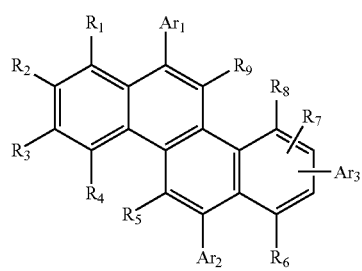

[1]

(In the general formula [1], $R_1$ to $R_9$ are each independently selected from the group consisting of a hydrogen atom, a substituted or unsubstituted alkyl group, and a substituted or unsubstituted alkoxy group, and $Ar_1$, $Ar_2$, and $Ar_3$ are each independently selected from the group represented by the following formulae [2].)

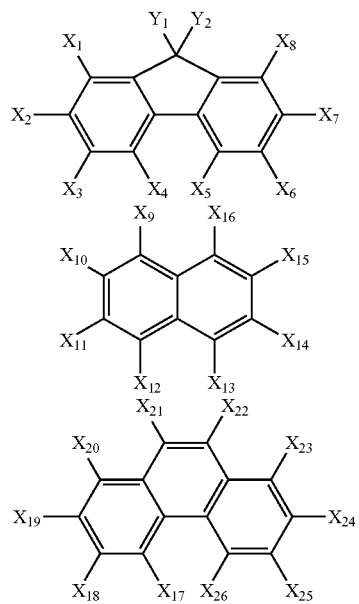

[2]

(In the formula [2], $X_1$ to $X_{26}$ are each independently selected from the group consisting of a hydrogen atom, a substituted or unsubstituted alkyl group, a substituted or unsubstituted alkoxy group, a substituted or unsubstituted phenyl group, a substituted or unsubstituted naphthyl group, a substituted or unsubstituted phenanthryl group, and a substituted or unsubstituted fluorenyl group, provided that one of $X_1$ to $X_8$, one of $X_9$ to $X_{16}$, and one of $X_{17}$ to $X_{26}$ each represent the chrysene ring represented by the general formula [1], and $Y_1$ and $Y_2$ are each independently selected from a hydrogen atom and a substituted or unsubstituted alkyl group.)

According to the present invention, there can be provided a novel chrysene compound having high chemical stability, a deep HOMO level, a wide energy gap, a small dihedral angle, and good carrier transport property. In addition, there can be provided an organic light-emitting device having the compound, the device having high emission efficiency and excellent driving durability.

BRIEF DESCRIPTION OF THE DRAWINGS

FIG. 1 is a schematic cross-sectional view illustrating an organic light-emitting device and a switching device connected to the organic light-emitting device.

BEST MODE FOR CARRYING OUT THE INVENTION

A chrysene compound according to the present invention is represented by the following general formula [1].

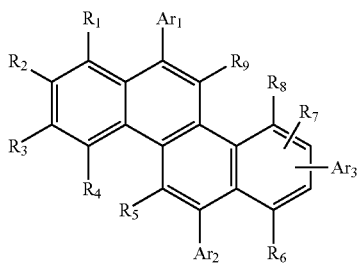

[1]

In the formula [1], $R_1$ to $R_9$ are each independently selected from the group consisting of a hydrogen atom, a substituted or unsubstituted alkyl group, and a substituted or unsubstituted alkoxy group.

Specific examples of the alkyl group include a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group, and an adamantyl group.

Specific examples of the alkoxy group include a methoxy group, an ethoxy group, an iso-propoxy group, a tert-butoxy group, an aryloxy group, and a benzyloxy group.

The above-mentioned alkyl group and alkoxy group may have a substituent. Examples of the substituent include: alkyl groups such as a methyl group, an ethyl group, and a propyl group; hydrocarbon aromatic ring groups such as a phenyl group, a naphthyl group, a phenanthryl group, and a fluorenyl group; heteroaromatic ring groups such as a thienyl group, a pyrrolyl group, and a pyridyl group; substituted amino groups such as a dimethylamino group, a diethylamino group, a dibenzylamino group, a diphenylamino group, a ditolylamino group, and a dianisolylamino group; alkoxy groups such as a methoxy group and an ethoxy group; aryloxy groups such as a phenoxy group and a naphthoxy group; halogen atoms such as fluorine, chlorine, bromine, and iodine; a hydroxyl group; a cyano group; and a nitro group.

The substituents $Ar_1$, $Ar_2$, and $Ar_3$ in the formula [1] are each independently selected from the group of substituents represented by the following formulae [2].

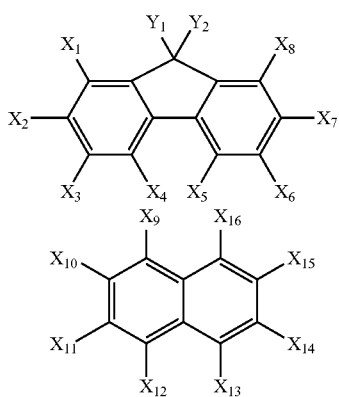

[2]

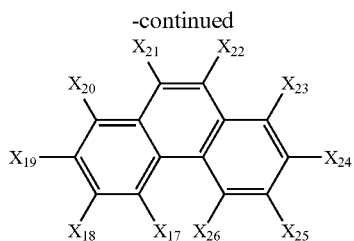

-continued

In the formula [2], $X_1$ to $X_{26}$ each independently represent substituents selected from the group consisting of a hydrogen atom, a substituted or unsubstituted alkyl group, a substituted or unsubstituted alkoxy group, a substituted or unsubstituted phenyl group, a substituted or unsubstituted naphthyl group, a substituted or unsubstituted phenanthryl group, and a substituted or unsubstituted fluorenyl group, provided that one of $X_1$ to $X_8$, one of $X_9$ to $X_{16}$, and one of $X_{17}$ to $X_{26}$ each represent the chrysene ring represented by the general formula [1].

Specific examples of the alkyl group represented by any one of $X_1$ to $X_{26}$ are identical to the above-mentioned specific examples of the alkyl group represented by any one of $R_1$ to $R_9$ in the formula [1]. Specific examples of the substituent which the alkyl group may further have are identical to the above-mentioned specific examples of the substituent which, when any one of $R_1$ to $R_9$ in the formula [1] represents an alkyl group, the alkyl group may further have.

Specific examples of the alkoxy group represented by any one of $X_1$ to $X_{26}$ are identical to the above-mentioned specific examples of the alkoxy group represented by any one of $R_1$ to $R_9$ in the formula [1]. Specific examples of the substituent which the alkoxy group may further have are identical to the above-mentioned specific examples of the substituent which, when any one of $R_1$ to $R_9$ in the formula [1] represents an alkoxy group, the alkoxy group may further have.

Specific examples of the substituent which the phenyl group, naphthyl group, phenanthryl group, and fluorenyl group represented by any one of $X_1$ to $X_{26}$ may further have include: an alkyl group such as a methyl group, an ethyl group, an iso-propyl group, a tert-butyl group, an n-hexyl group, and a cyclohexyl group; an aromatic hydrocarbon ring group such as a phenyl group, a tolyl group, a tert-butylphenyl group, a xylyl group, a mesityl group, a naphthyl group, a phenanthryl group, a fluorenyl group, a 9,9-dimethylfluorenyl group, a 9,9-diethylfluorenyl group, and a 9,9-di-(n-hexyl)fluorenyl group; an aromatic heterocyclic group such as a thienyl group, a pyrrolyl group, a pyridyl group, and a phenanthrolinyl group; a substituted amino group such as a dimethylamino group, a diethylamino group, a dibenzylamino group, a diphenylamino group, a ditolylamino group, and a dianisolylamino group; an alkoxy group such as a methoxy group and an ethoxy group; an aryloxy group such as a phenoxy group and a naphthoxy group; a halogen atom such as fluorine, chlorine, bromine, and iodine; a hydroxyl group; a cyano group; and a nitro group.

$Y_1$ and $Y_2$ in the formula [2] are each independently selected from a hydrogen atom and a substituted or unsubstituted alkyl group.

Specific examples of the alkyl group represented by any one of $Y_1$ and $Y_2$ are identical to the above-mentioned specific examples of the alkyl group represented by any one of $R_1$ to $R_9$ in the formula [1]. Specific examples of the substituent which the alkyl group may further have is identical to the above-mentioned specific example of a substituent which, when any one of $R_1$ to $R_9$ in the formula [1] represents an alkyl group, the alkyl group may further have.

In addition, all or part of the hydrogen atoms present at the main skeleton (this refers to the chrysene skeleton represented in the general formula [1]) or substituents in the main skeleton in the chrysene compound represented by the formula [1] may each be replaced with deuterium.

The chrysene compound represented by the formula [1] is preferably a compound represented by any one of the formulae [3] and [4].

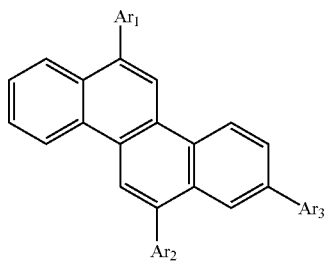

[3]

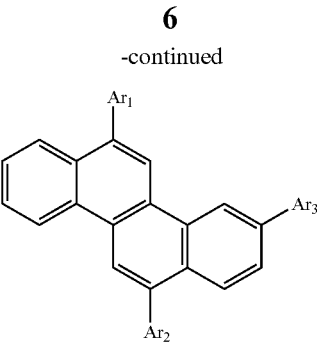

[4]

It should be noted that the substituents $Ar_1$ to $Ar_3$ in each of the formulae [3] and [4] are identical to the substituents $Ar_1$ to $Ar_3$ in the formula [1].

Next, methods of synthesizing a 2,6,12-triaryl-substituted chrysene compound represented by the formula [3] and a 3,6,12-triaryl-substituted chrysene compound represented by the formula [4] according to this embodiment are described.

The 2,6,12-triaryl-substituted chrysene compound can be synthesized by a Suzuki-Miyaura coupling reaction represented by the following formula [5].

That is, a 2-Cl intermediate is synthesized from 6,12-dibromo-2-chlorochrysene, and further, an aryl group is introduced so that the 2,6,12-triaryl-substituted chrysene compound may be obtained.

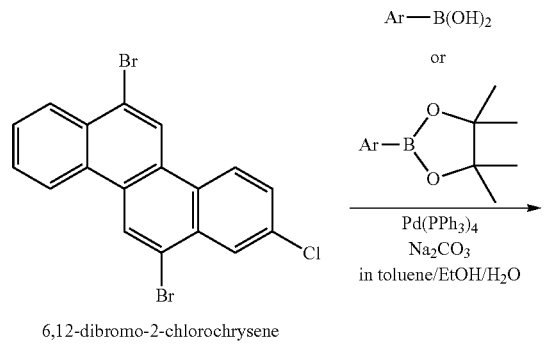

6,12-dibromo-2-chlorochrysene

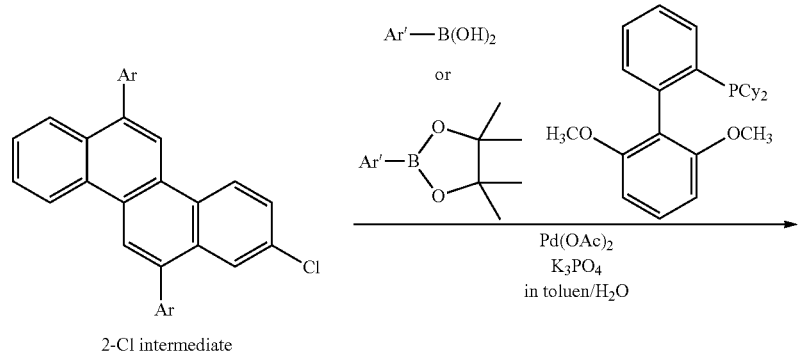

2-Cl intermediate

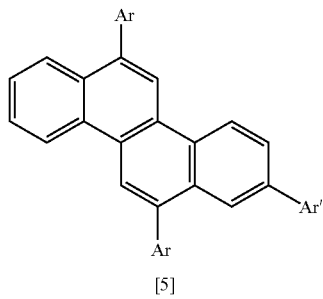

[5]

2,6,12-triaryl-substituted chrysene compound (In the formula, Ar and Ar' represent substituents each independently selected from the group consisting of a substituted or unsubstituted naphthyl group, a substituted or unsubstituted phenanthryl group, and a substituted or unsubstituted fluorenyl group.)

Similarly, the 3,6,12-triaryl-substituted chrysene compound can be synthesized from 6,12-dibromo-3-chlorochrysene via a 3-Cl intermediate as represented by the following formula [6].

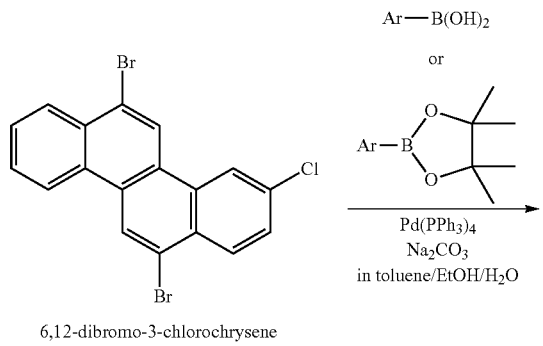

6,12-dibromo-3-chlorochrysene

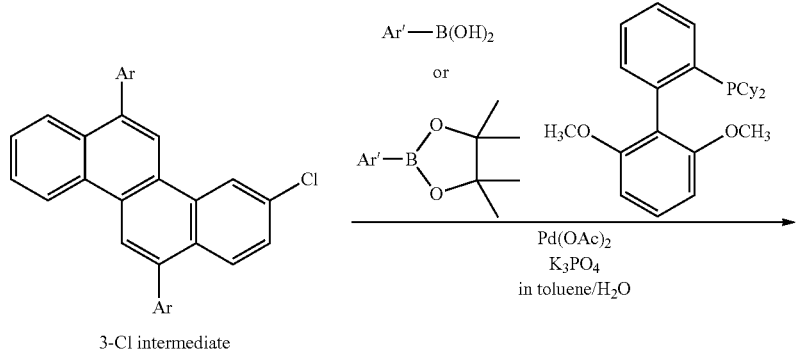

3-Cl intermediate

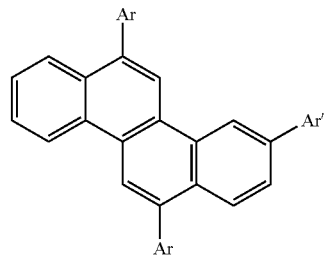

[6]

3,6,12-triaryl-substituted chrysene compound (In the formula, Ar and Ar' represent substituents each independently selected from the group consisting of a substituted or unsubstituted naphthyl group, a substituted or unsubstituted phenanthryl group, and a substituted or unsubstituted fluorenyl group.)

When, in each of the formulae [5] and [6], a Cl intermediate into which a desired aryl group is introduced as Ar is synthesized, and desired Ar' is introduced in the subsequent coupling reaction, a chrysene compound substituted with desired Ar and Ar' can be synthesized. In this case, a boronic acid compound corresponding to each of desired Ar and Ar' is used as a boronic acid compound in each of the formulae.

It should be noted that, when an alkyl group or alkoxy group is introduced into the chrysene compound as the finally synthesized substance in each of the formulae, the dibromo-chlorochrysene in the formula has only to be alkylated or alkoxylated.

Hereinafter, specific structural formulae of the chrysene compound according to the present invention are exemplified.

C101
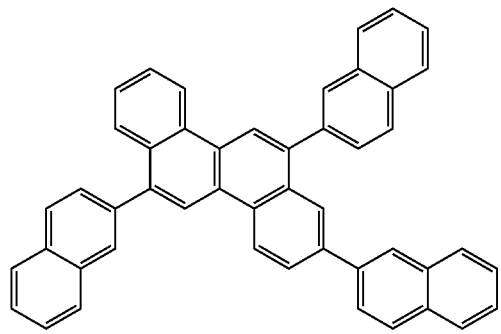

C102
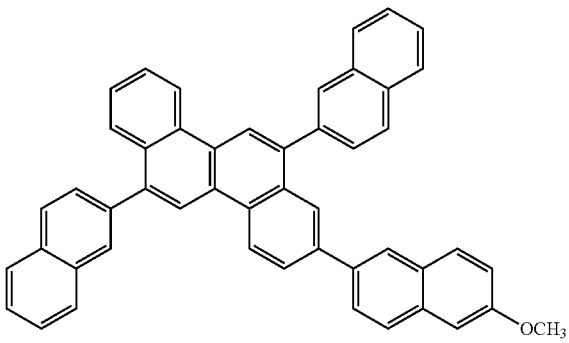

C103
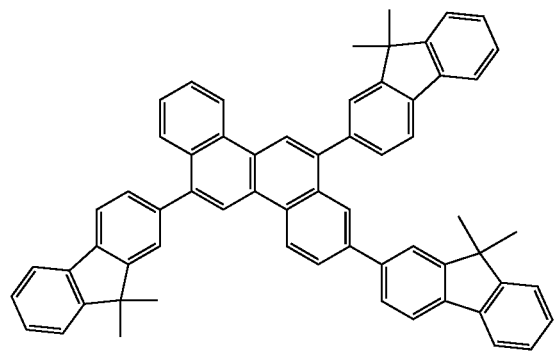

C104
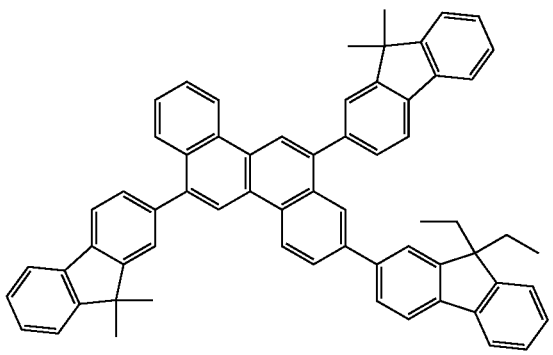

C105
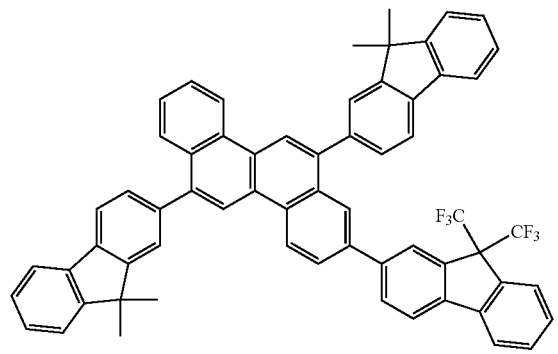

C106
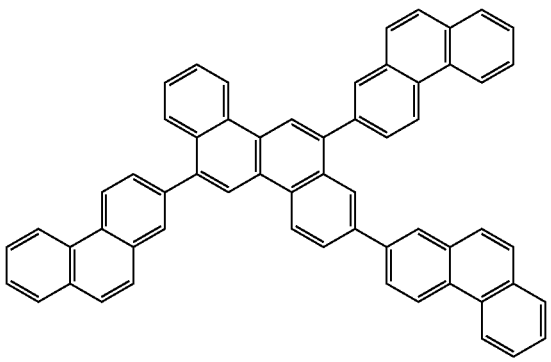

-continued
C107
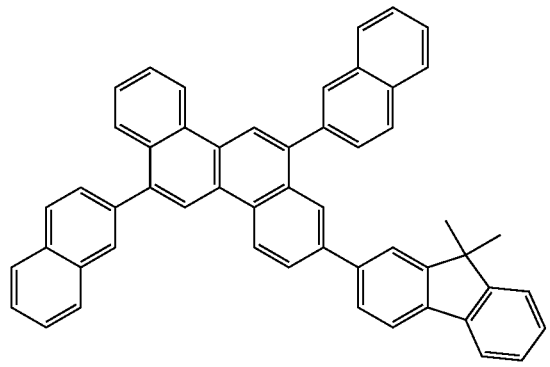
C109
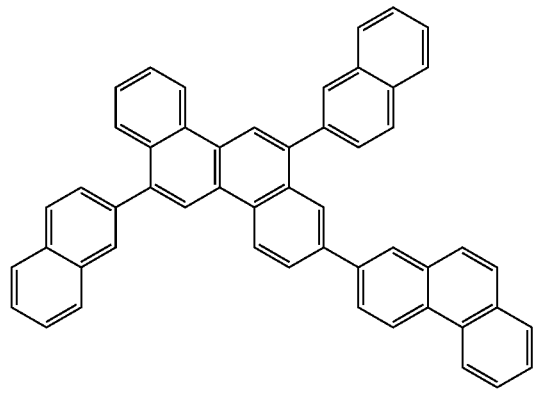
C110
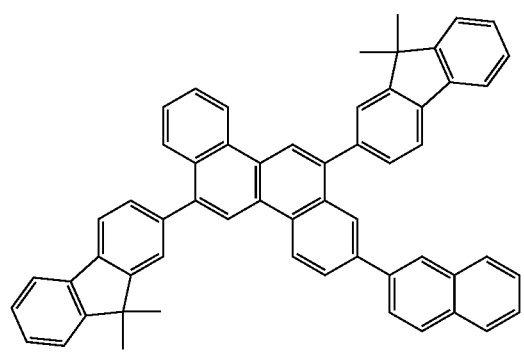
C111
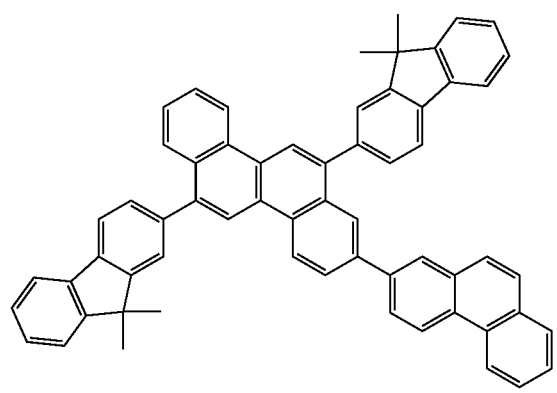
C112
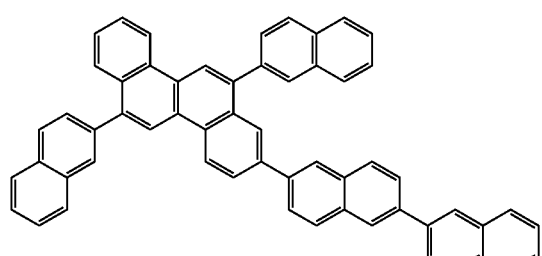
C201
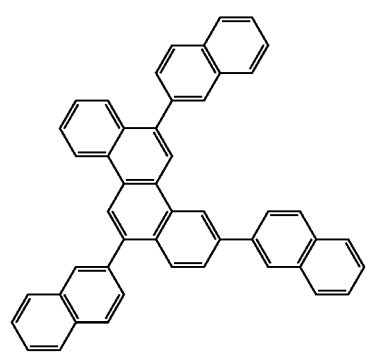

-continued
C202
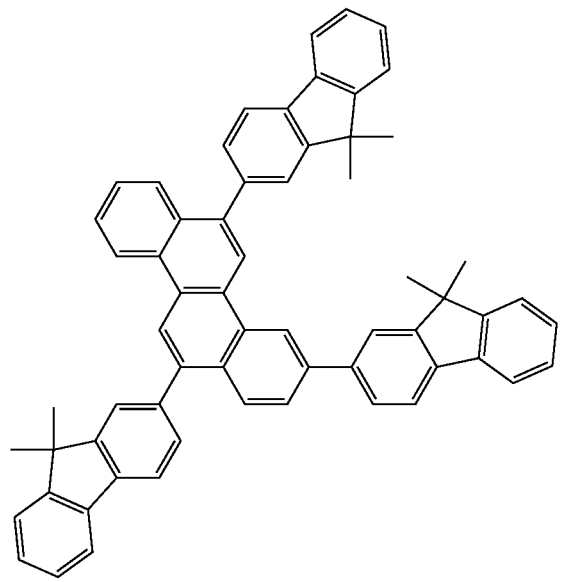
C203
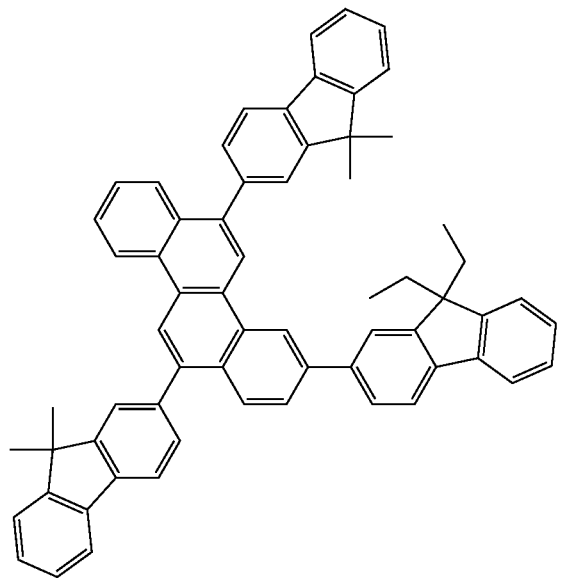
C204
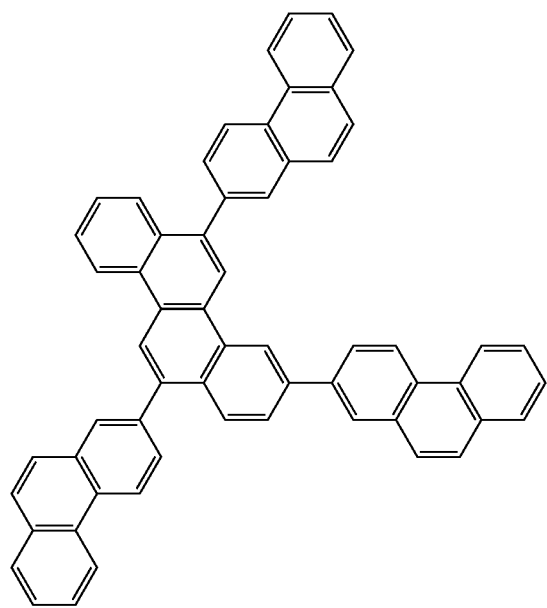
C205
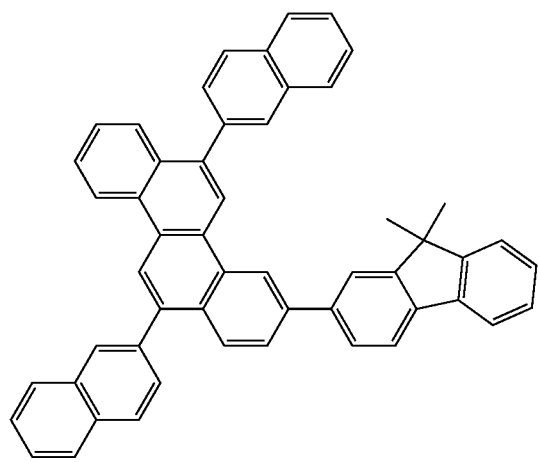

-continued
C206
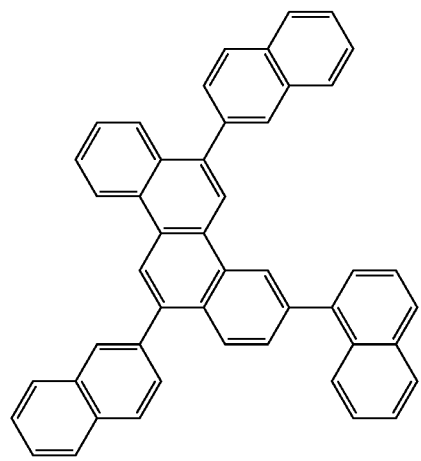
C207
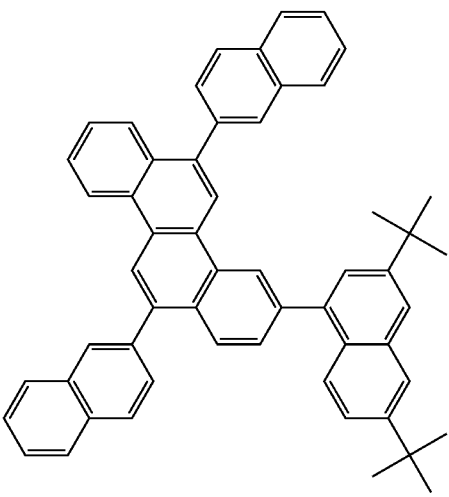
C208
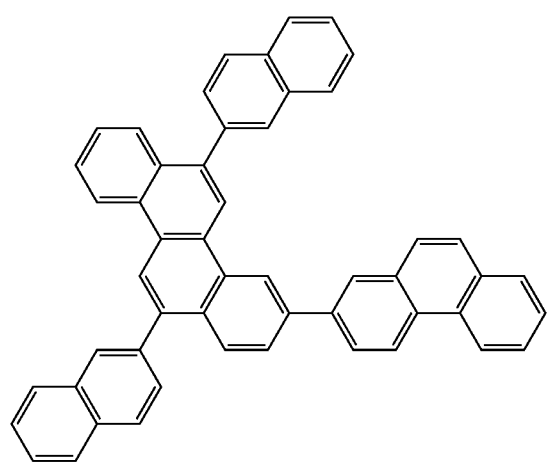
C209
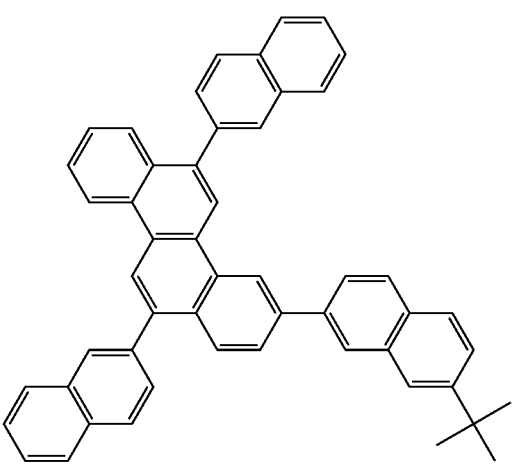
C210
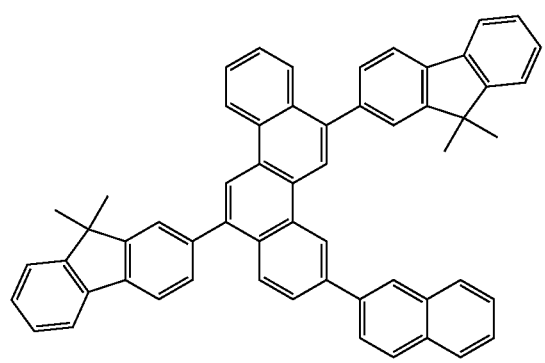
C211
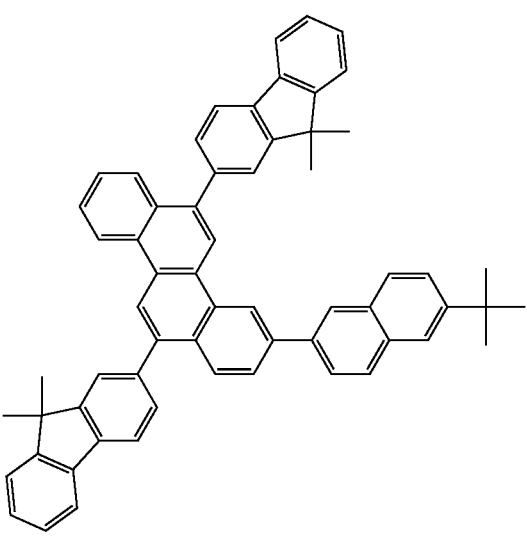

-continued
C212
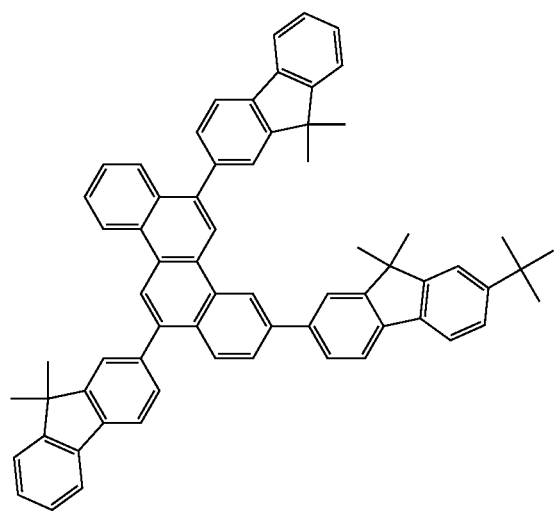
C213
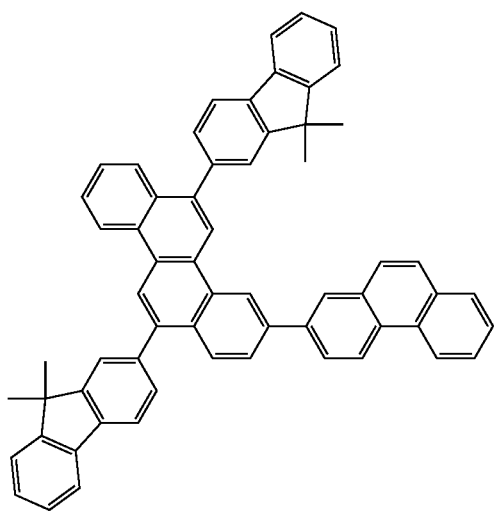
C214
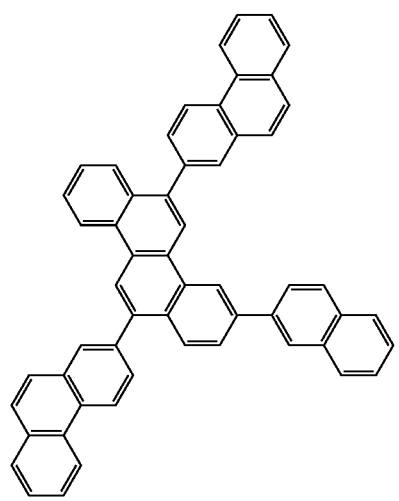
C215
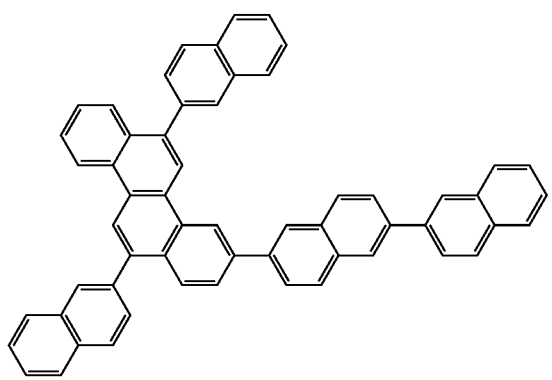
C301
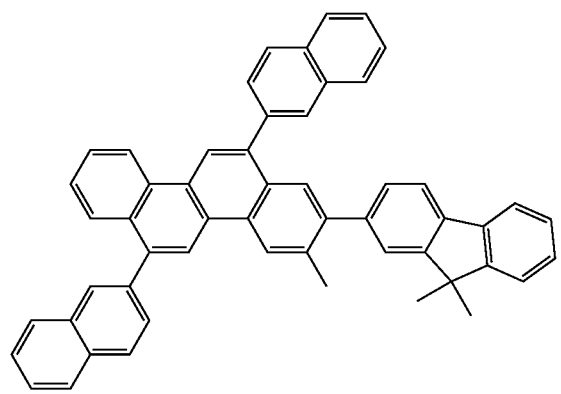
C302
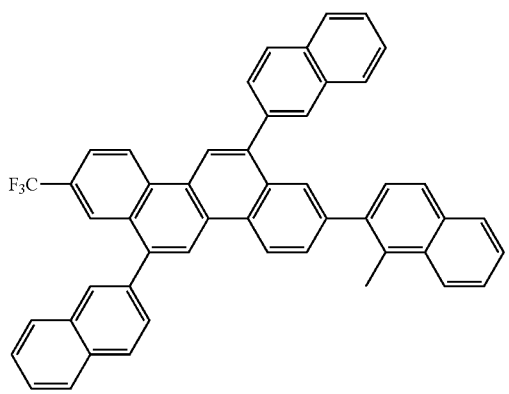

-continued
C303
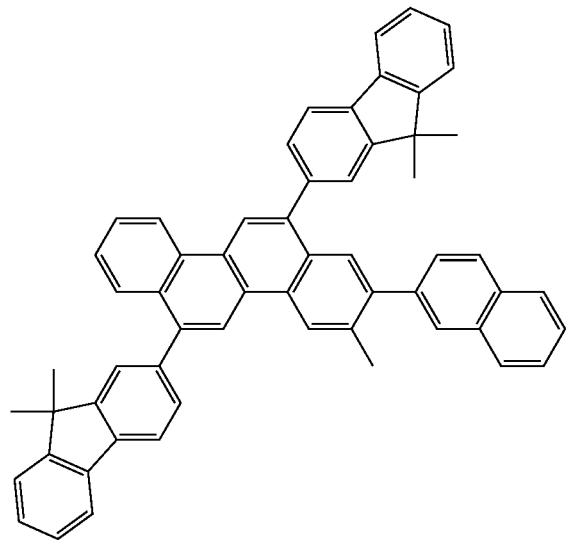
C401
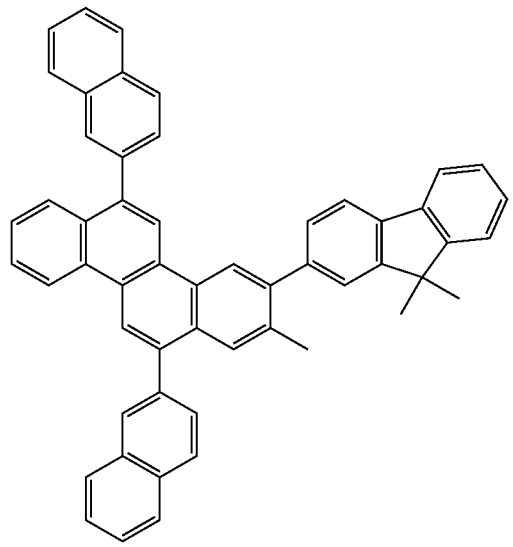
C402
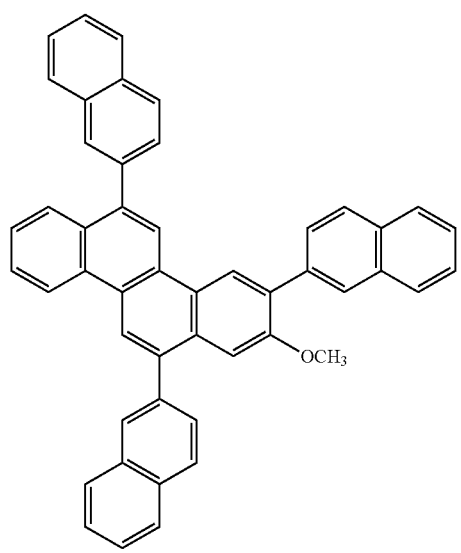
C403
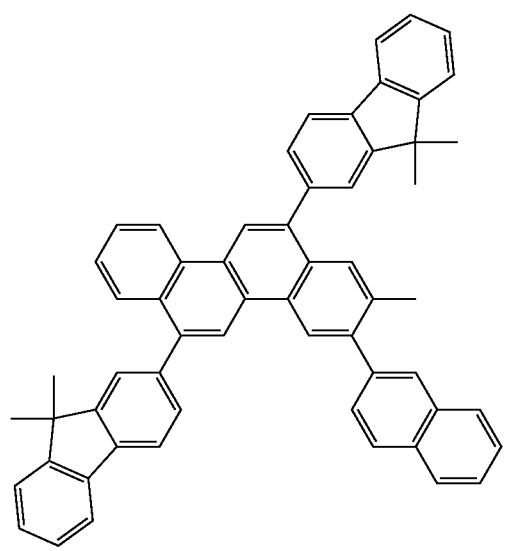
C501
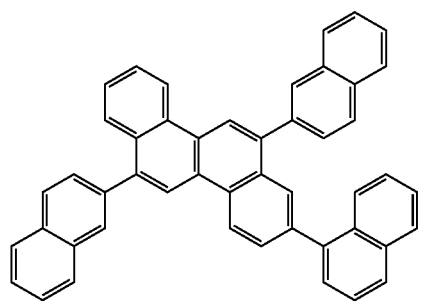
C502
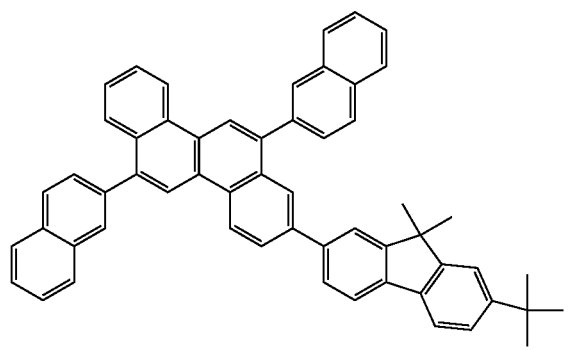

-continued
C503 C504 C505 C506 C507 C508
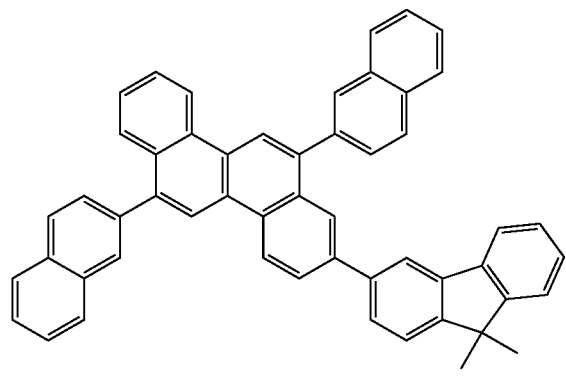

-continued
C509
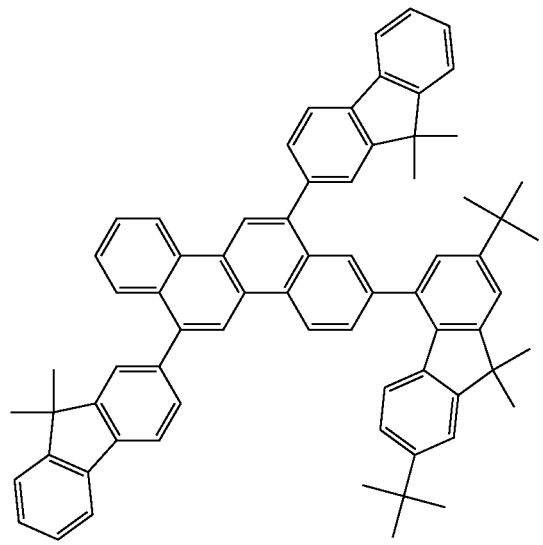
C510
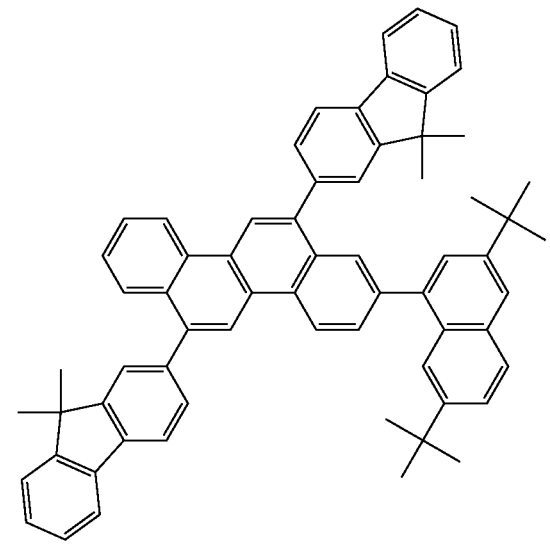
C511
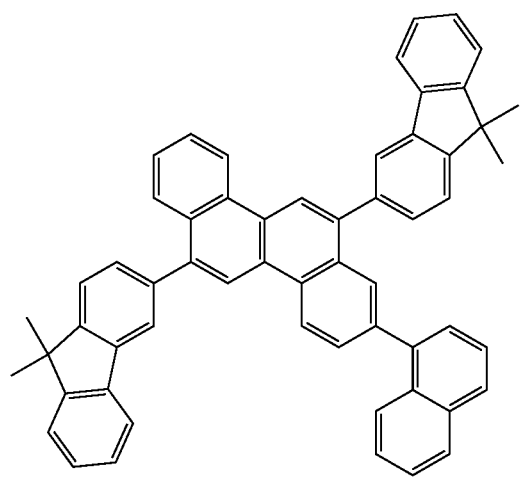
C512
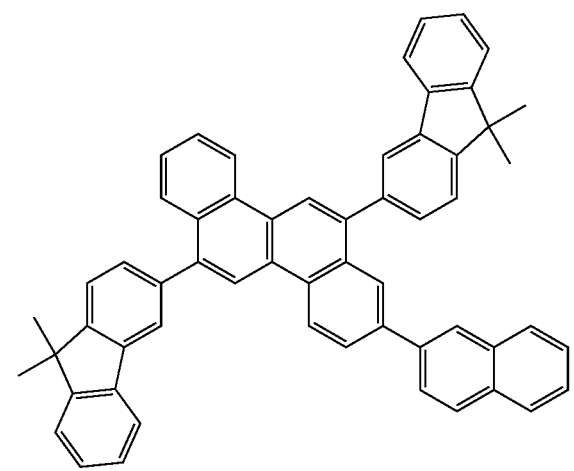
C513
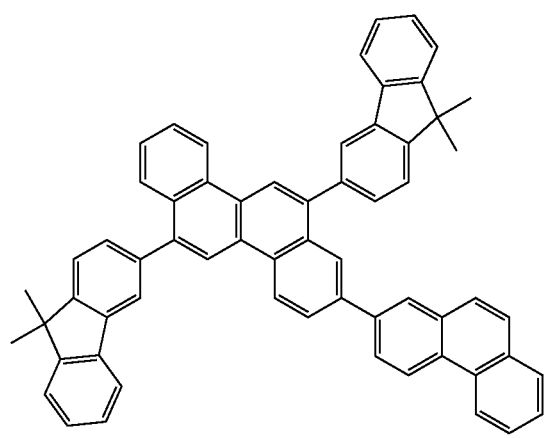
C514
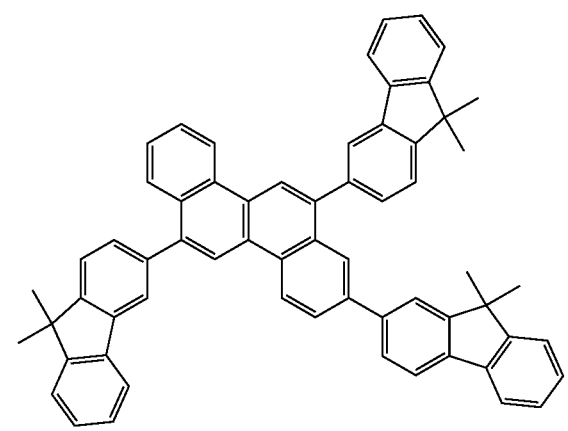

-continued
C515
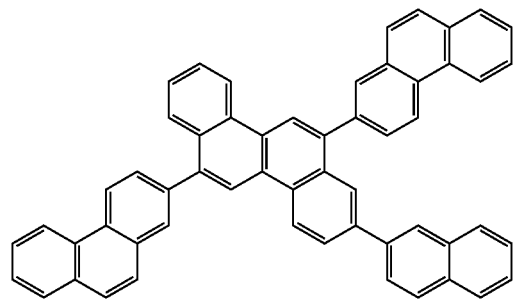
C516
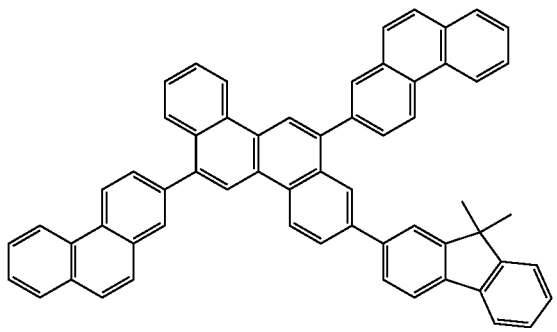
C517
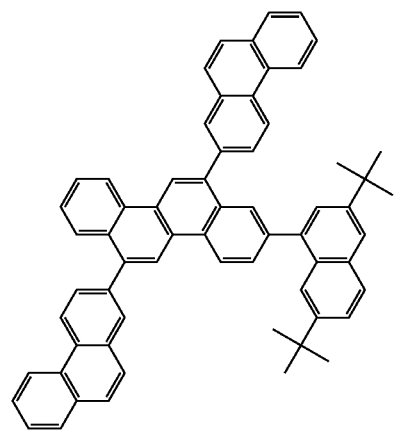
C518
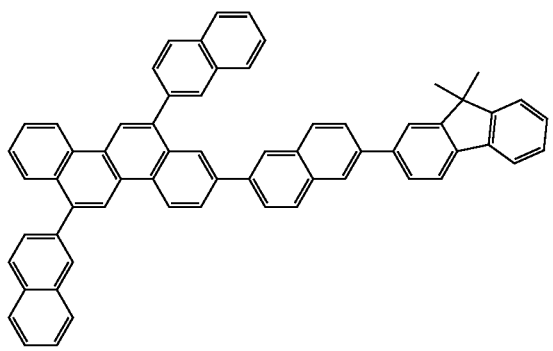
C519
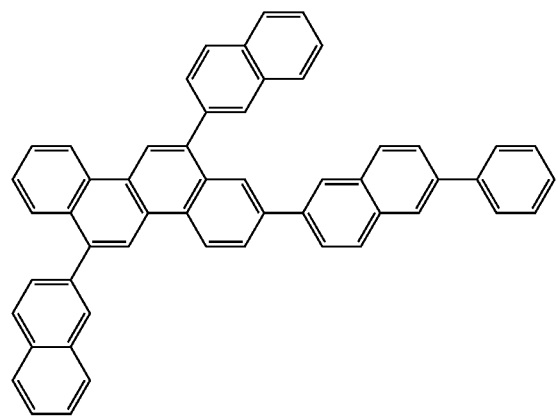

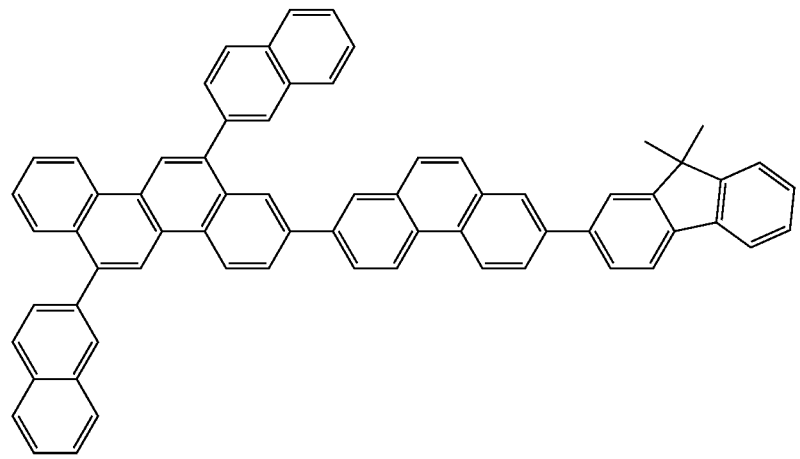
C520
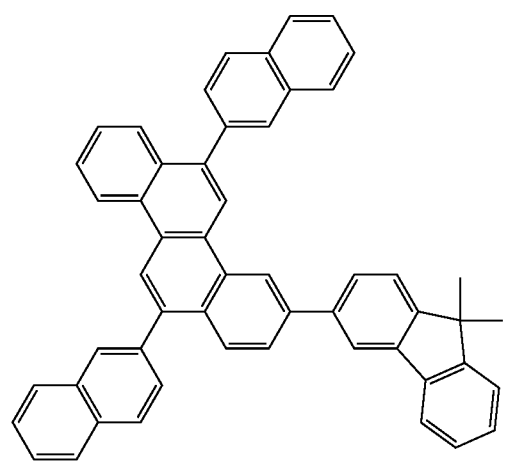
C601
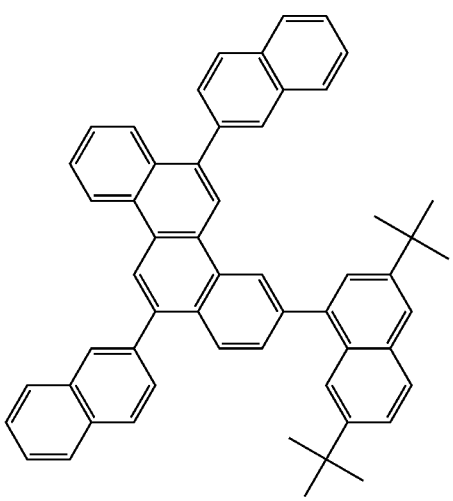
C602
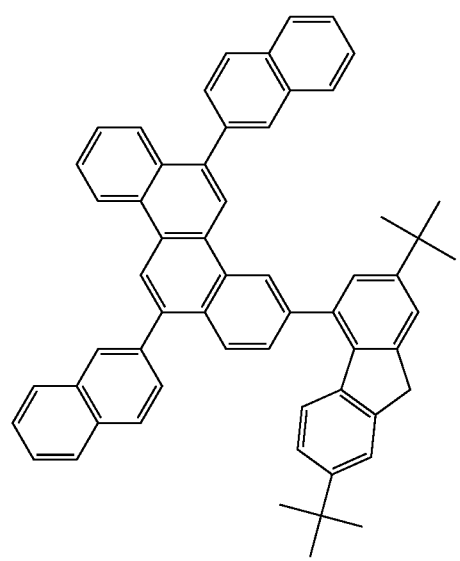
C603
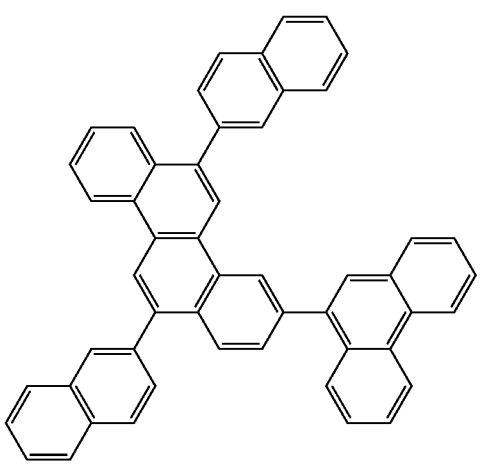
C604

-continued
C605
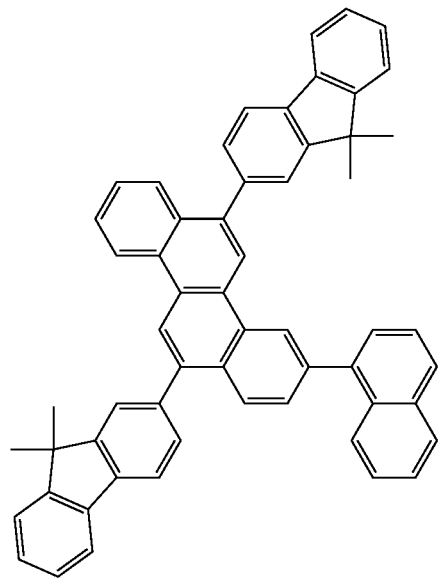
C606
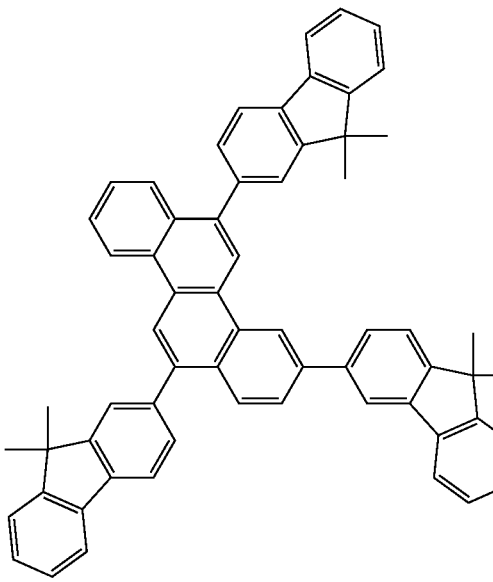
C607
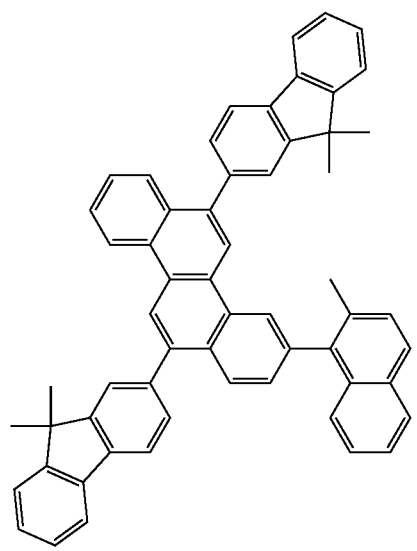
C608
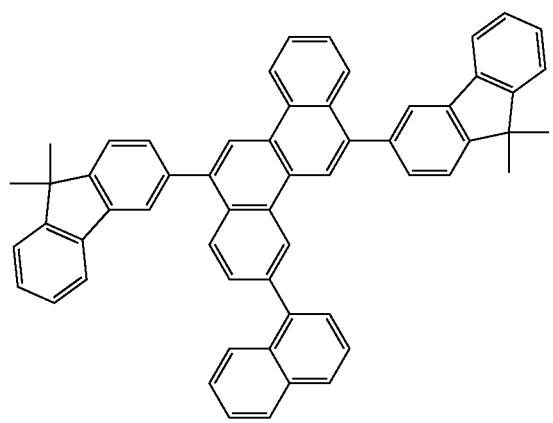
C609
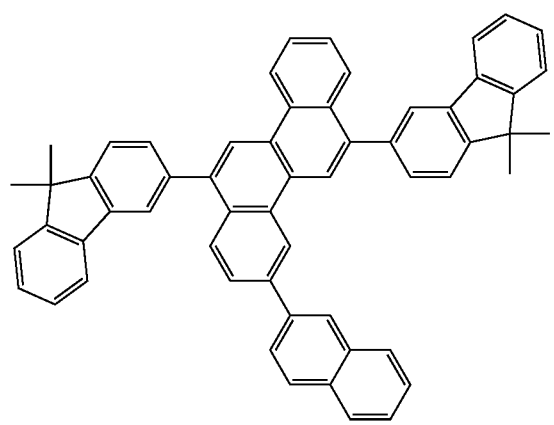
C610
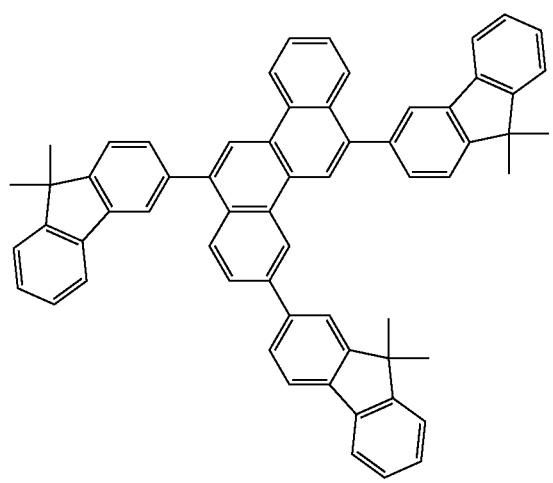

-continued
C611
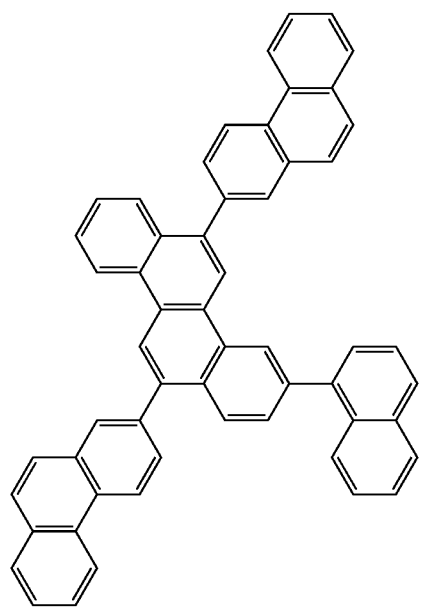
C612
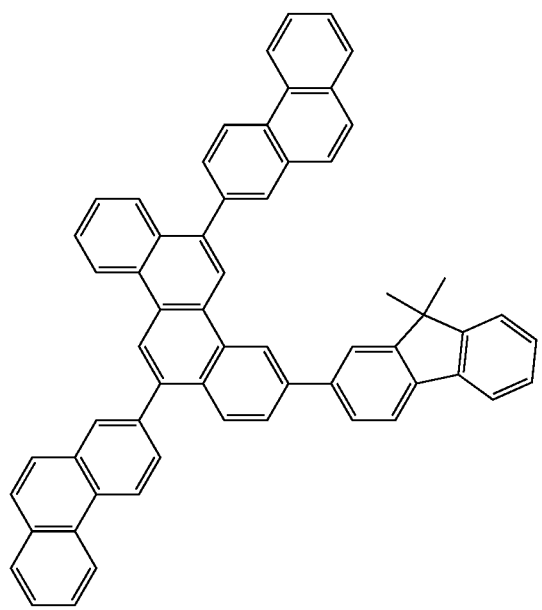
C613
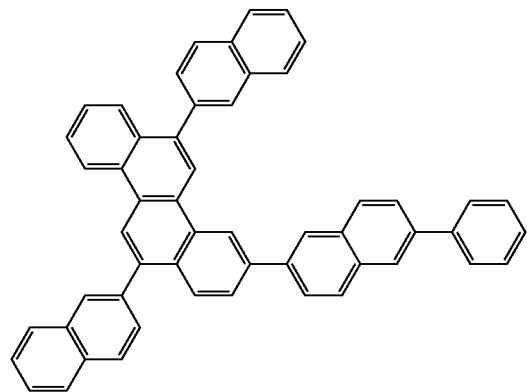
C614
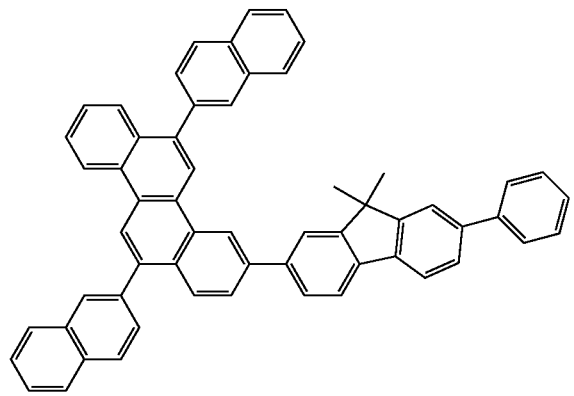
C615
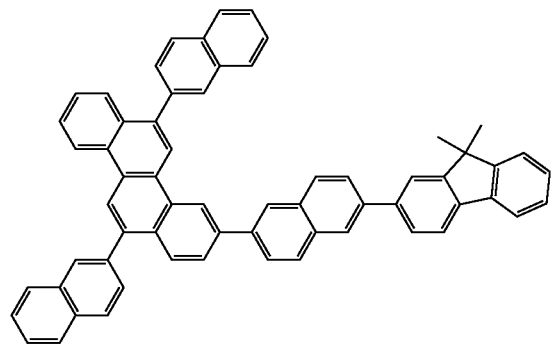
C701
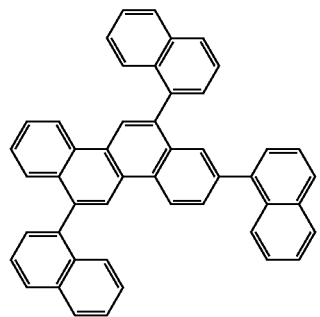

-continued
C702
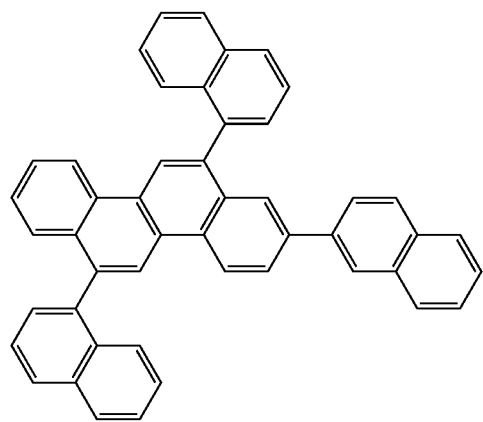
C703
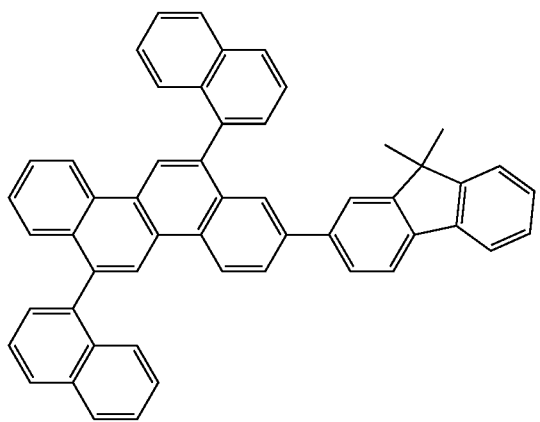
C704
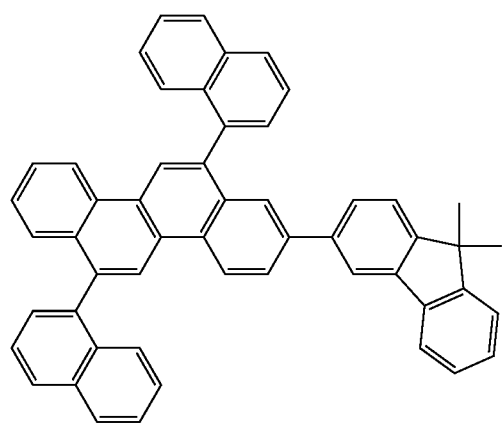
C705
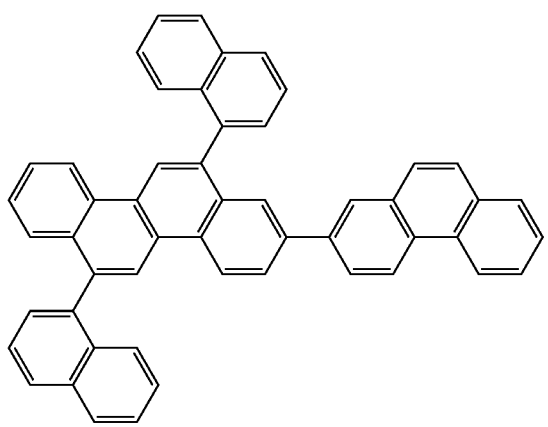
C706
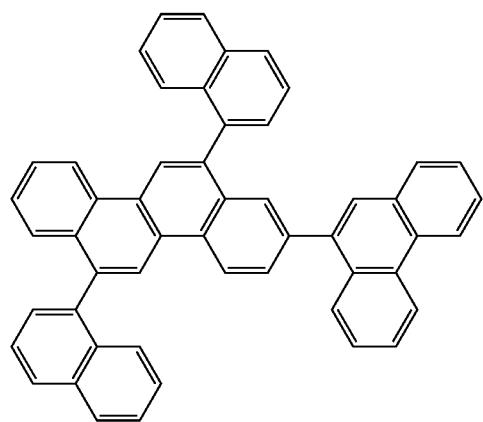
C707
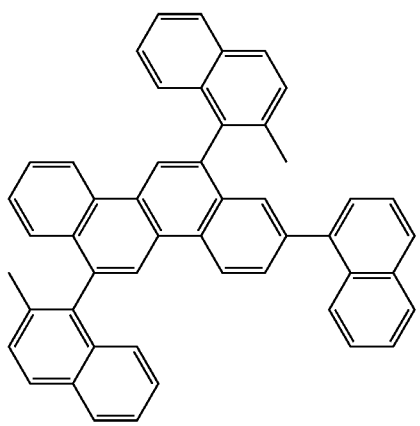

-continued
C708
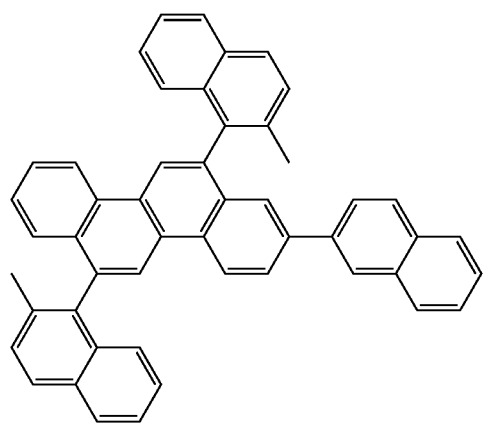
C709
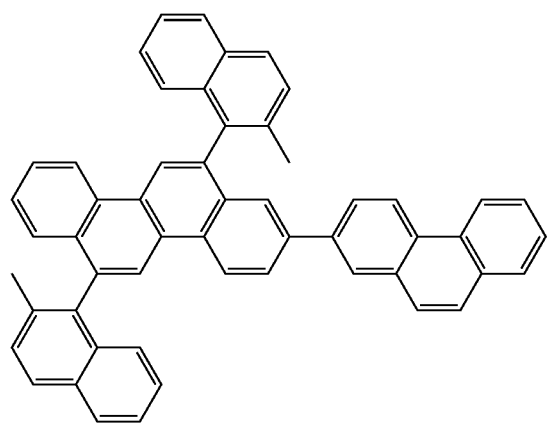
C710
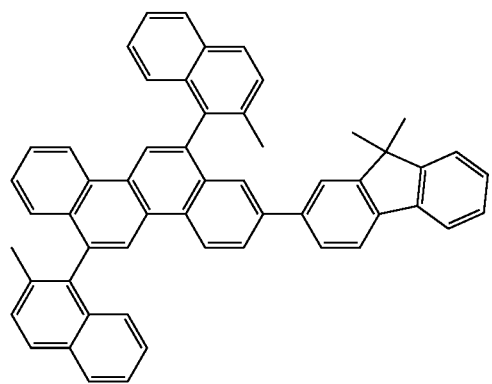
C711
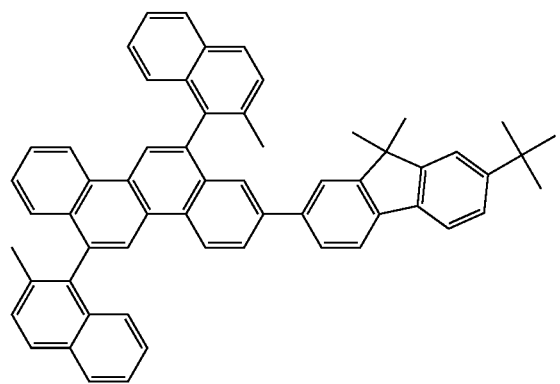
C712
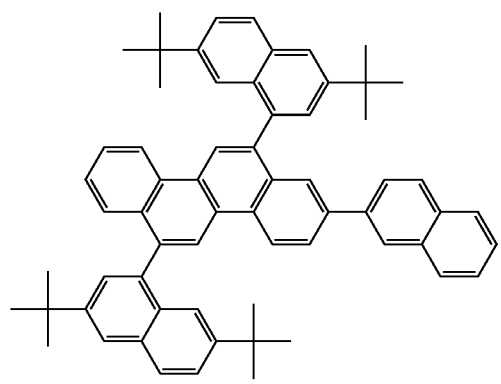
C713
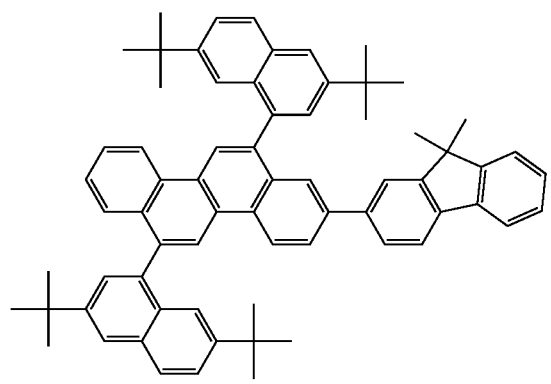

-continued
C714
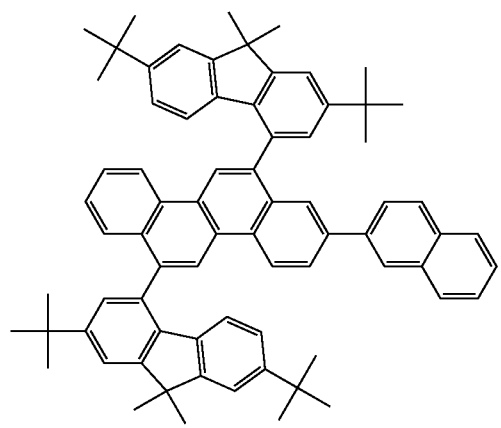
C715
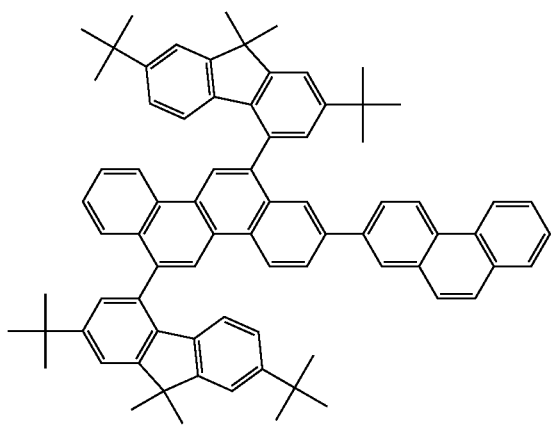
C716
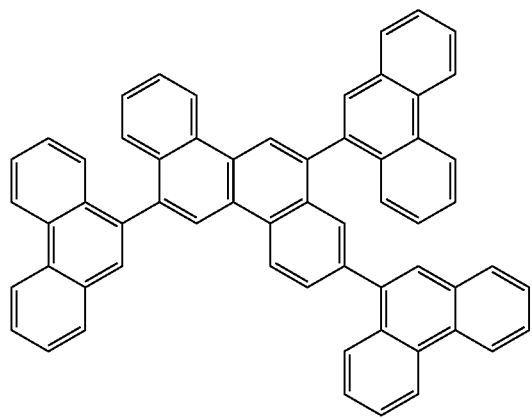
C717
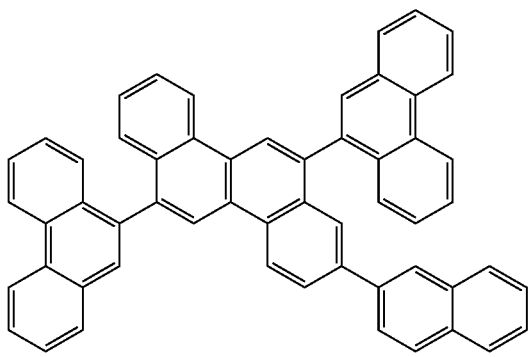
C718
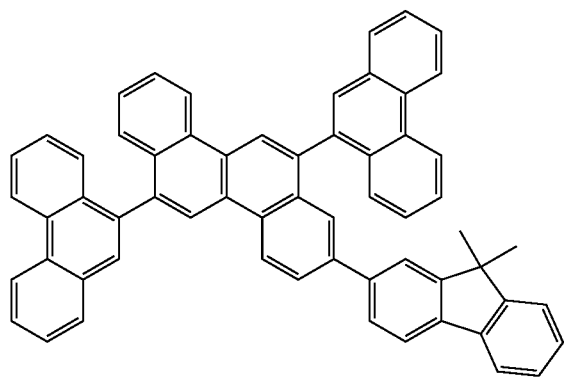
C719
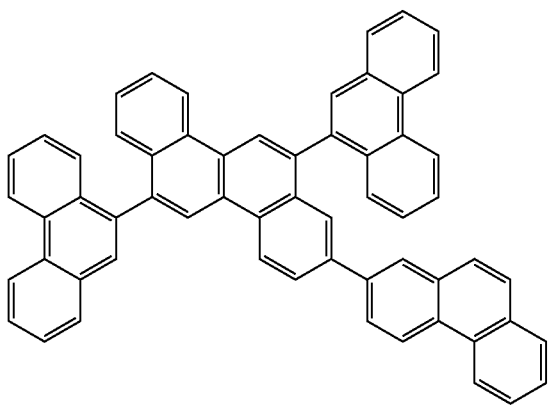

-continued
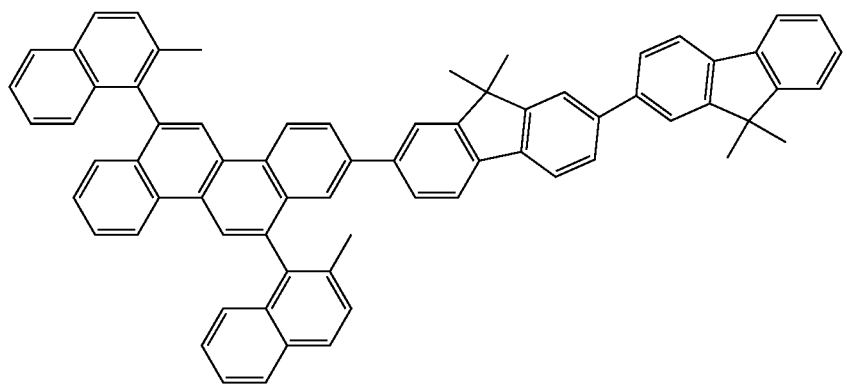
C720
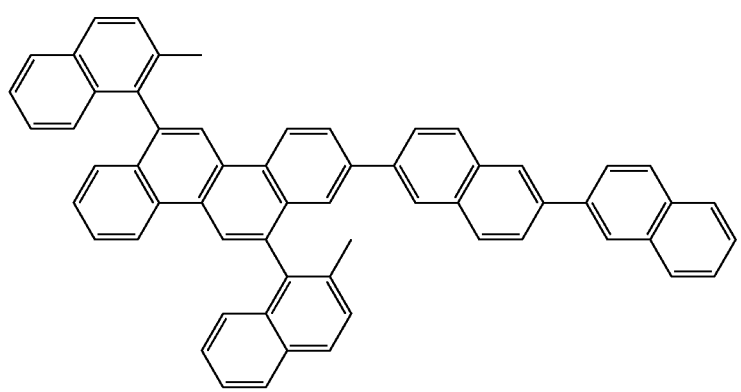
C721
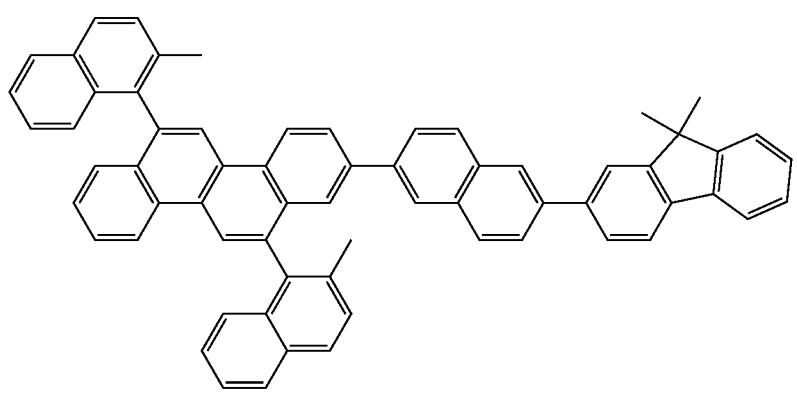
C722
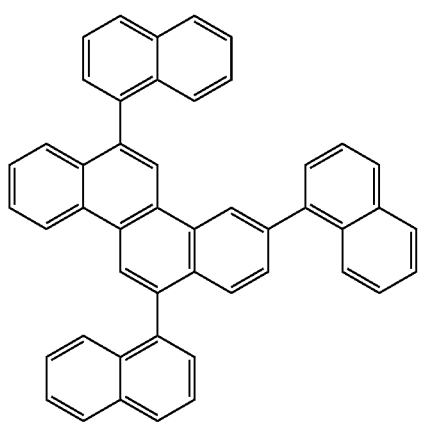
C801
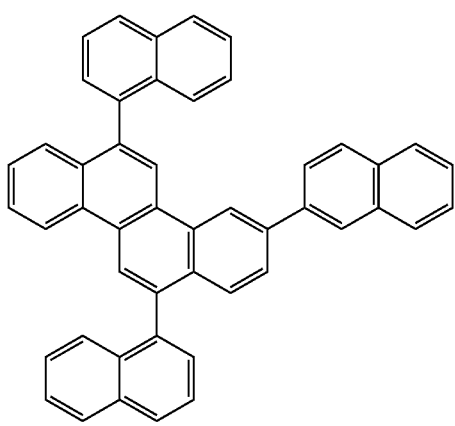
C802

-continued
C803
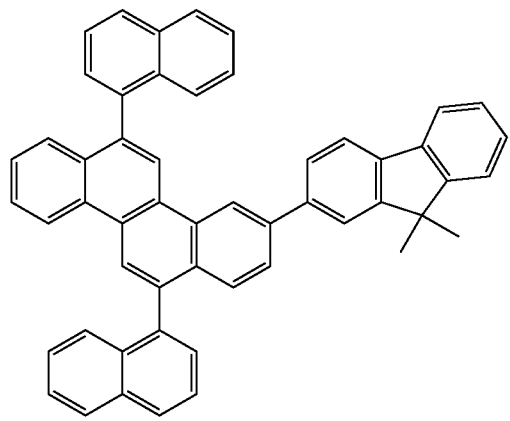
C804
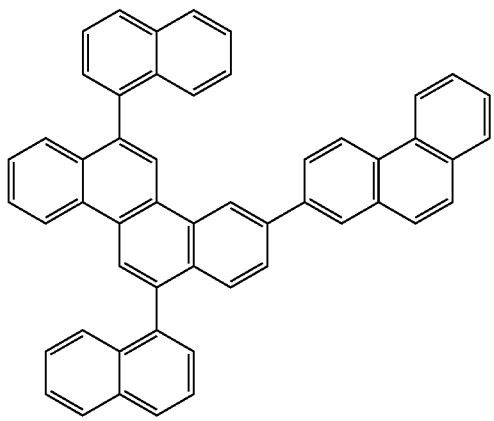
C805
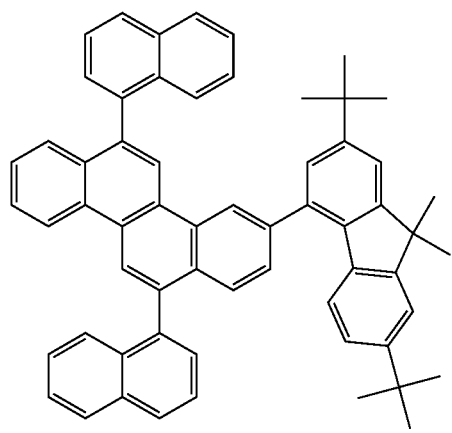
C806
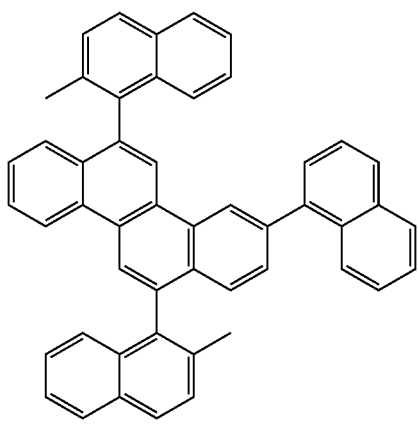
C807
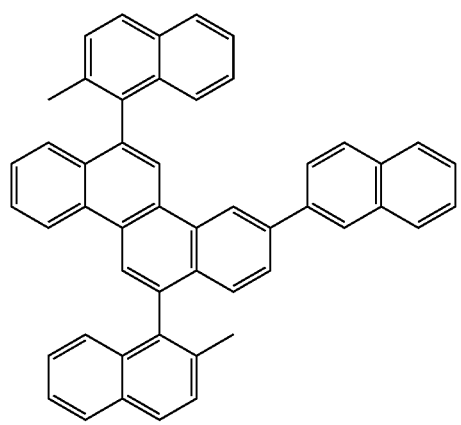
C808
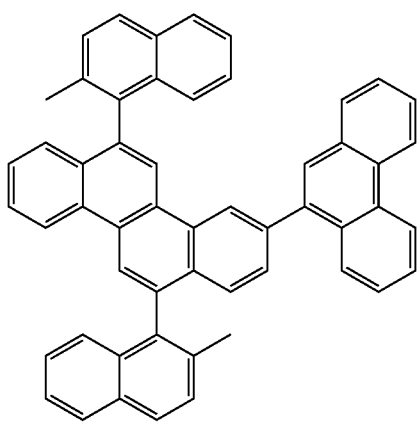

-continued
C809
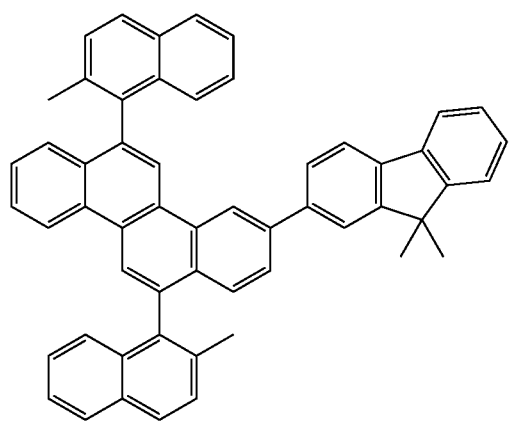
C810
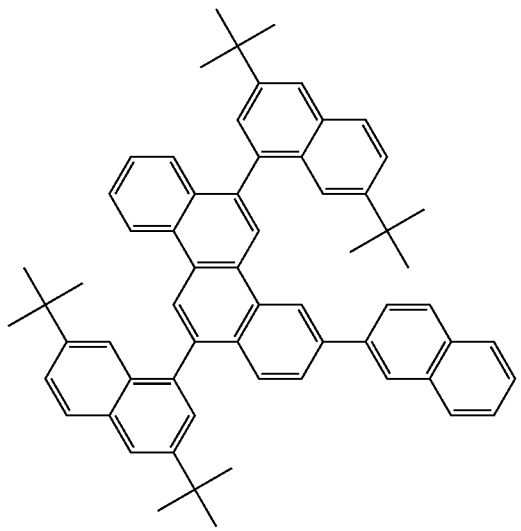
C811
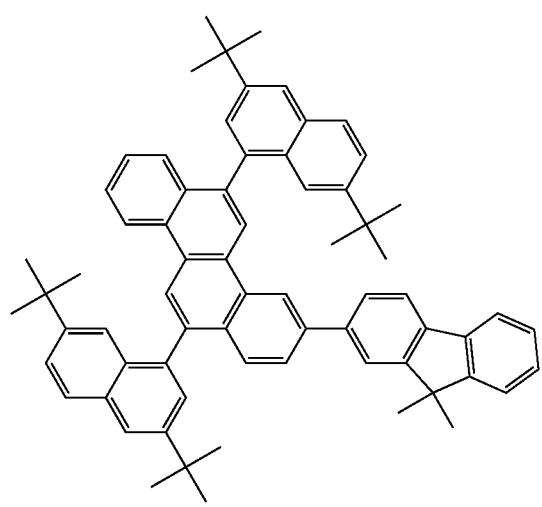
C812
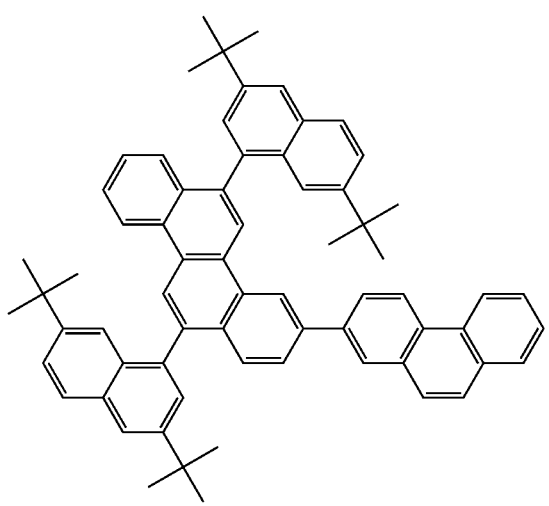
C813
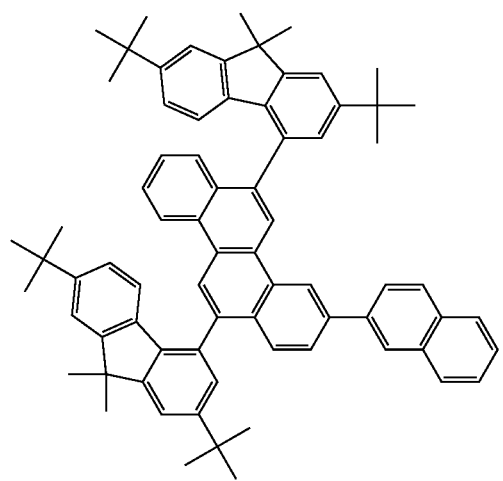
C814
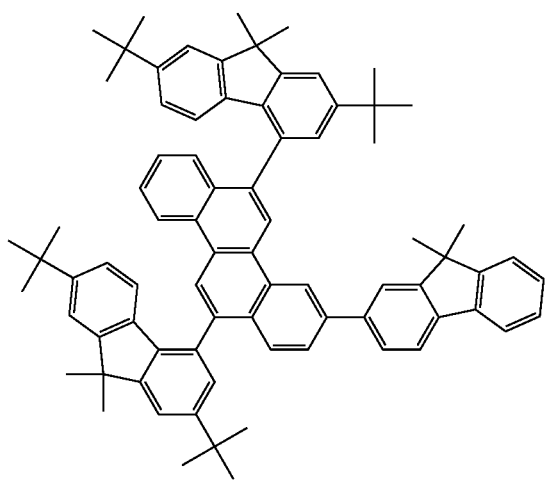

-continued
C815
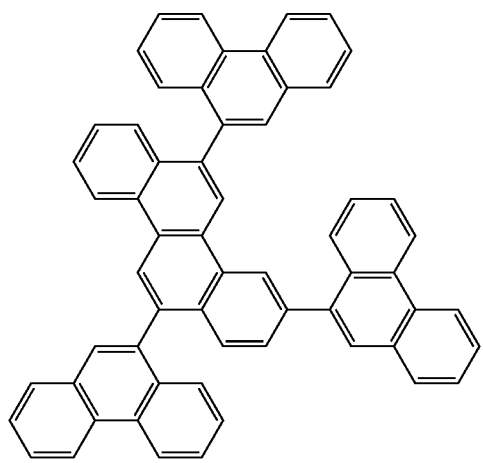
C816
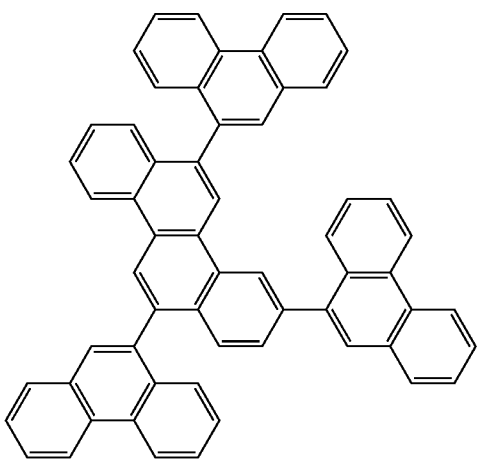
C817
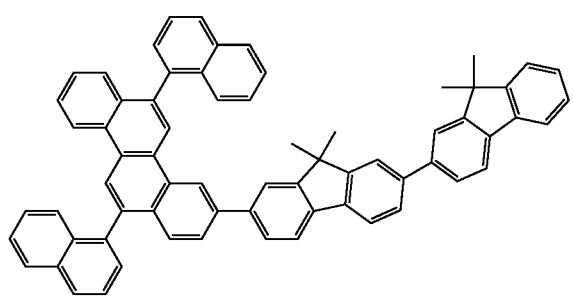
C818
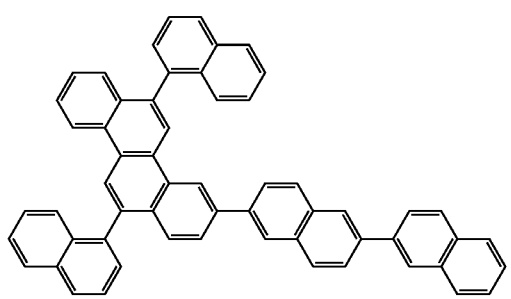
C819
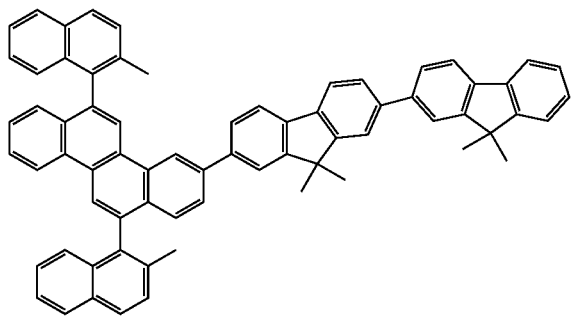
C820
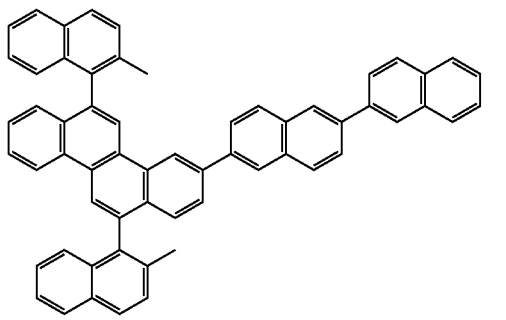
C821
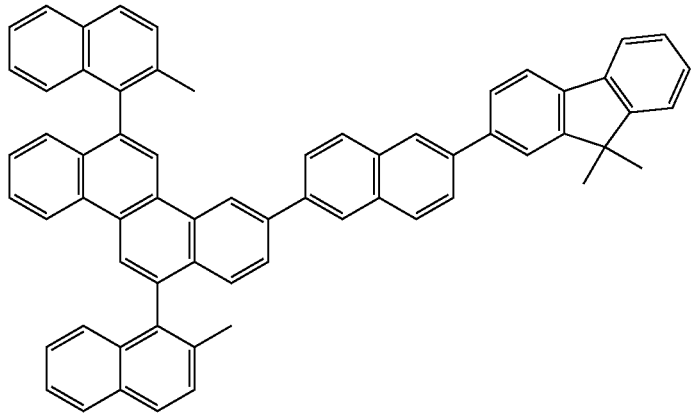
Compounds C101 to C112 (hereinafter referred to as "C100 group"), C501 to C520 (hereinafter referred to as "C500 group"), and C701 to C722 (hereinafter referred to as "C700 group") shown above are specific examples of the 2,6,12-triaryl chrysene compound represented by the general formula [3].

Compounds C201 to C215 (hereinafter referred to as "C200 group"), C601 to C615 (hereinafter referred to as "C600 group"), and C801 to C821 (hereinafter referred to as "C800 group") shown above are specific examples of the 3,6,12-triaryl chrysene compound represented by the general formula [4].

Compounds C301 to C303 (hereinafter referred to as "C300 group") and C401 to C403 (hereinafter referred to as "C400 group") shown above are specific examples of a compound in which at least one of $R_1$ to $R_9$ in the general formula [1] represents a substituent except a hydrogen atom.

Of the C100 group, Compounds C102, C107, C109, and C112 each have the same nature as that of Compound C101 in terms of a relatively deep HOMO level and high hole blocking property when used in an electron transport layer. Each of those compounds can be generally represented by the following general formula [7].

[7]

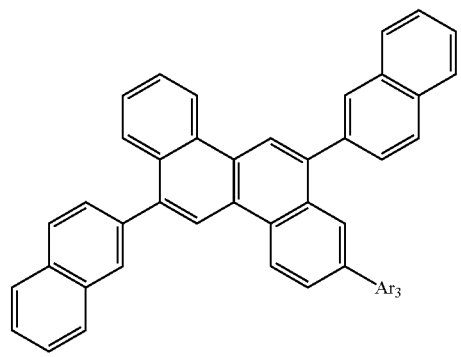

Of the C100 group, Compounds C104, C105, C110, and C111 each have the same nature as that of Compound C103 in terms of a relatively shallow HOMO level and high hole injection property when used as a host material for an emission layer. Each of those compounds can be generally represented by the following general formula [8].

[8]

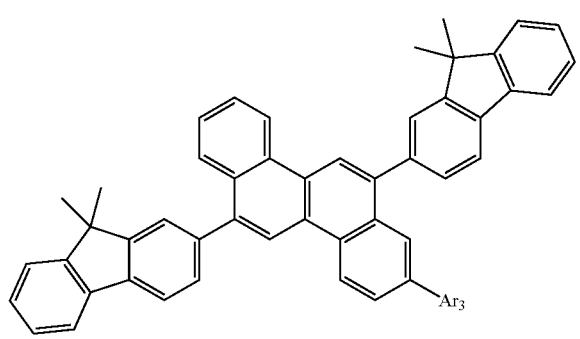

Of the C200 group, Compounds C205, C208, C209, and C215 each have the same nature as that of Compound C201 in terms of a relatively deep HOMO level and high hole blocking property when used in an electron transport layer. Each of those compounds can be generally represented by the following general formula [9].

[9]

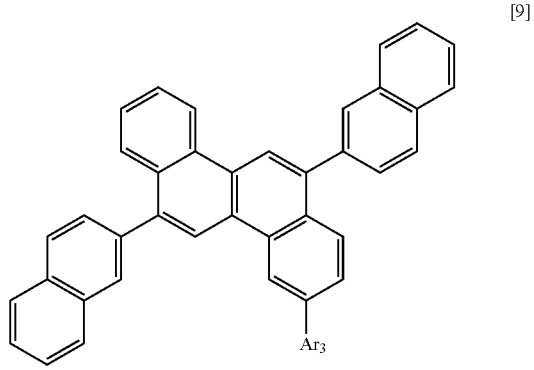

Of the C200 group, Compounds C203, C210, C211, C212, and C213 each have the same nature as that of Compound C202 in terms of a relatively shallow HOMO level and high hole injection property when used as a host material for an emission transport layer. Each of those compounds can be generally represented by the following general formula [10].

[10]

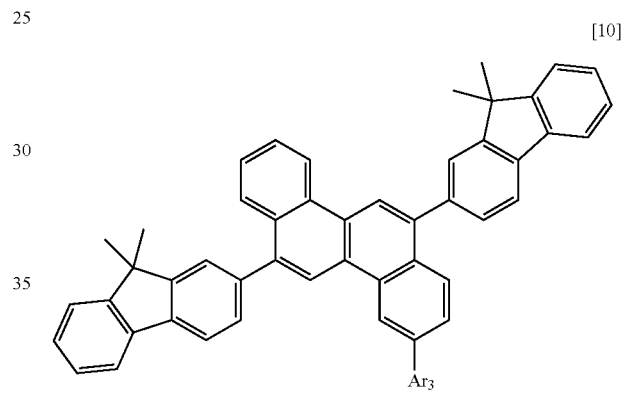

Of the C500 group, Compounds C506, C507, C510, C511, and C517 each have the same nature as that of Compound C501. Each of those compounds can be generally represented by the following general formula [11]. Those compounds are common to one another in terms of high hole blocking property and high exciton blocking property when used in an electron transport layer because of a deep HOMO level and a relatively large energy gap.

[11]

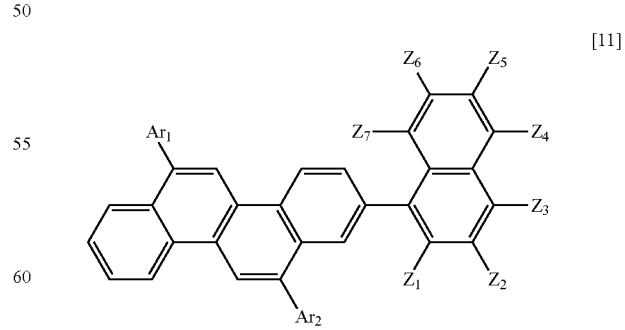

(In the formula [11], $Z_1$ to $Z_7$ each independently represents a hydrogen atom or an alkyl group.)

Of the C500 group, Compound C509 has the same nature as that of Compound C505 in terms of a relatively large energy gap and high exciton blocking property when used in an electron transport layer. The compound can be generally represented by the following general formula [12].

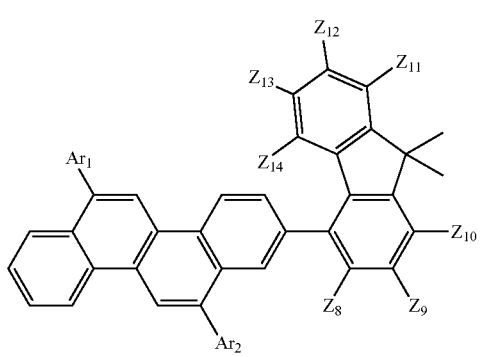

[12]

(In the formula [12], $Z_8$ to $Z_{14}$ each independently represents a hydrogen atom or an alkyl group.)

Of the C700 group, Compounds C702, C704, C705, C708, C709, C710, C711, C712, C713, C720, C721, and C722 each have the same nature as that of Compound C703. Each of those compounds can be generally represented by the following general formula [13].

Those compounds are common to one another in terms of a deep HOMO level and a large energy gap, and high hole blocking property and high exciton blocking property when used in an electron transport layer.

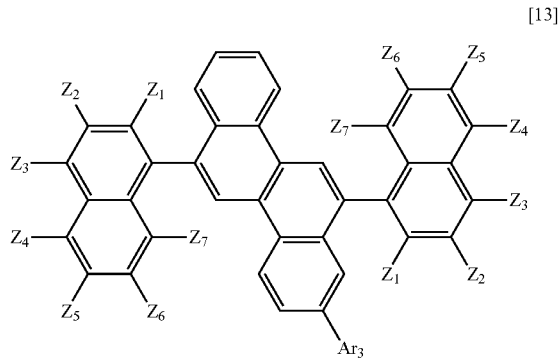

[13]

(In the formula [13], $Z_1$ to $Z_7$ each independently represents a hydrogen atom or an alkyl group.)

It should be noted that the substituents $Ar_1$ to $Ar_3$ in each of the formulae [8] to [13] are identical to the substituents $Ar_1$ to $Ar_3$ in the formula [1].

Next, the organic light-emitting device according to the present invention is described in detail.

The organic light-emitting device according to the present invention is an organic light-emitting device formed of a pair of electrodes formed of an anode and a cathode, and an organic compound layer interposed between the pair of electrodes, in which the organic compound layer contains an organic compound represented by the general formula [1].

The device may have a compound layer except the above-mentioned organic compound layer between the pair of electrodes. Alternatively, two or more compound layers including the organic compound layer may be provided between the pair of electrodes, and the device in such case is called a multilayer organic light-emitting device.

Hereinafter, preferred examples of the multilayer organic light-emitting device, i.e., first to sixth examples are described.

An organic light-emitting device of such a constitution that the anode, an emission layer, and the cathode are sequentially provided on a substrate can be given as the first example of the multilayer organic light-emitting device. An organic light-emitting device of such a constitution that the anode, a hole transport layer, an electron transport layer, and the cathode are sequentially provided on a substrate can be given as the second example of the multilayer organic light-emitting device. In this case, the emission layer is any one of the hole transport layer and the electron transport layer.

An organic light-emitting device of such a constitution that the anode, the hole transport layer, the emission layer, the electron transport layer, and the cathode are sequentially provided on a substrate can be given as the third example of the multilayer organic light-emitting device. An organic light-emitting device of such a constitution that the anode, a hole injection layer, the hole transport layer, the emission layer, the electron transport layer, and the cathode are sequentially provided on a substrate can be given as the fourth example of the multilayer organic light-emitting device.

An organic light-emitting device of such a constitution that the anode, the hole injection layer, the hole transport layer, the emission layer, the electron transport layer, the electron injection layer, and the cathode are sequentially provided on a substrate can be given as the fifth example of the multilayer organic light-emitting device. An organic light-emitting device of such a constitution that the anode, the hole transport layer, the emission layer, a hole blocking layer or exciton blocking layer, the electron transport layer, and the cathode are sequentially provided on a substrate can be given as the sixth example of the multilayer organic light-emitting device.

However, the first to sixth examples of the multilayer organic light-emitting device have only a basic device constitution, and the constitution of the organic light-emitting device according to the present invention is not limited thereto. There can be given various layer constitutions, for example, a constitution in which an insulating layer is provided at an interface of an electrode and an organic layer, an adhesive layer or an interference layer is provided, an electron transport layer or a hole transport layer is formed of two layers having different ionization potentials, or an emission layer has a stacked structure formed of two layers or more.

The organic compound layer in the organic light-emitting device according to the present invention may contain one kind of chrysene compound according to the present invention, or may have multiple kinds of the chrysene compounds according to the present invention.

In the organic light-emitting device according to the present invention, the chrysene compound of the present invention is preferably used as a host material for the emission layer.

Alternatively, the chrysene compound according to the present invention may be used as a guest material for the emission layer.

Further, the chrysene compound according to the present invention may be used in any one of the respective layers except the emission layer, i.e., the hole injection layer, the hole transport layer, the hole blocking layer, the exciton blocking layer, the electron transport layer, and the electron injection layer. Further, the chrysene compound according to the present invention is preferably provided on the electron transport layer.

The organic light-emitting device is such a device that an emission material as an organic compound interposed between a pair of electrodes emits light. The layer having the emission material is the emission layer.

The emission layer may be formed only of the chrysene compound according to the present invention, or may partly have the chrysene compound according to the present invention. When the emission layer partly has the chrysene compound according to the present invention, the chrysene compound may be the emission material in the emission layer, or may be a non/emission material in the layer.

When the emission layer is formed of multiple kinds of components, the components can be classified into a main component and sub-components. The term "main component" refers to a compound present in a large amount in terms of, for example, weight or number of moles out of all compounds of which the emission layer is formed, and the term "sub-component" refers to a compound present in a small amount in terms of any such parameter. A material as the main component can be called a host material. Materials as sub-components can be called a guest (dopant) material, an emission assist material, and a charge injection material. Here, the guest material is a compound which plays a role of main light emission inside the emission layer. On the other hand, the host material is a compound which is present as a matrix in the periphery of the guest material inside the emission layer, and mainly plays roles of transporting carriers and donating excitation energy to the guest material.

The concentration of the guest material with respect to the host material is 0.01 wt % to 50 wt % and preferably 0.1 wt % to 20 wt % based on the total amount of the constituent materials of the emission layer. More preferably, in order to prevent concentration quenching, the concentration of the guest material is desirably 10 wt % or less. Further, the guest material may be uniformly included throughout the layer formed of the host material, may be included in the layer with a concentration gradient existing, or may be partially included in a certain area to form an area formed of the host material layer where no guest material is included.

Next, the fact that the chrysene compound according to the present invention is useful in improving the durability life of the organic light-emitting device is described.

There are some possible causes for the degradation of the light-emitting characteristics of the organic light-emitting device due to electrification.

The possible causes include an emission center material itself and a cause related to a change in environment surrounding the emission material due to a molecule around the material. In addition, the possible causes include the degradation of the amorphous film quality of a film (layer) due to, for example, crystallization and the degradation of an organic layer over time due to the electrification itself as well. The degradation of the emission material due to oxidation is one kind of the degradation of the material, and the presence of an oxide in the organic light-emitting device is known to shorten the durability life of the device.

An anthracene compound having an anthracene ring as a core in its molecule has been generally known as the emission material for an organic light-emitting device. The carbon atoms at the 9- and 10-positions of the anthracene ring are oxidized with extreme ease. Therefore, the use of the anthracene compound as a host material for the emission layer of the organic light-emitting device often shortens the durability life of the organic light-emitting device owing to the above-mentioned degradation of the material due to oxidation.

Meanwhile, chrysene can be given as a hydrocarbon aromatic ring having carbon atoms comparable in number to those of anthracene. Unlike the anthracene ring, a chrysene ring has strong oxidation resistance, and a chrysene compound having the chrysene ring as a core in its molecule has extremely high chemical stability. In view of the foregoing, the inventors of the present invention have thought that the use of the chrysene compound in the organic light-emitting device is effective in lengthening the life of the device. In addition, the inventors have though that, in this case, it is important that the center of the charge distribution of each of an HOMO and an LUMO germane to an emission process be present on the chrysene ring in order for the chrysene compound to show its chemical stability. The inventors have paid attention to the fact that, with regard to an aromatic ring substituent on the chrysene ring of such chrysene compound, the singlet energy of the aromatic ring must be larger than that of chrysene. This is because, when dealing with the molecule by classifying the molecule into the core (main skeleton) and the substituent, the inventors wish to expect a main function from chrysene as the core and to expect only tuning for the function from the substituent. When the singlet energy of the aromatic ring substituent of the chrysene ring is larger than that of chrysene, a field for carrier recombination or carrier transport serving as an energetically large load in terms of energy can be converged on the chrysene ring having high chemical stability in one molecule.

The singlet energies of chrysene and various aromatic rings are compared in view of such way of thinking.

Table 1 below shows representative aromatic rings and their singlet energies in terms of wavelength. In addition, the singlet energy of chrysene in terms of wavelength is also shown in the same table. Of those aromatic rings, a phenyl group, a fluorenyl group, a naphthyl group, and a phenanthryl group each have a higher singlet energy than that of chrysene. When the chrysene compound has any such aromatic ring as a substituent, the HOMO and LUMO of the compound having the substituent are localized on the chrysene ring as the core.

TABLE 1

| Aromatic ring | Singlet energy (in terms of wavelength) |
|---|---|
| Benzene | 261 nm |
| Fluorene | 301 nm |
| Naphthalene | 310 nm |
| Phenanthrene | 345 nm |
| Chrysene | 361 nm |
| Pyrene | 371 nm |
| Anthracene | 376 nm |
| Perylene | 435 nm |

On the other hand, for example, when an aromatic ring group substituting for the chrysene ring is an aromatic ring having a smaller singlet energy than that of chrysene such as a pyrenyl group, there is a possibility that chemical stability derived from chrysene cannot be obtained.

By the way, out of a phenyl group, a fluorenyl group, a naphthyl group, and a phenanthryl group, groups excluding the phenyl group, i.e., the fluorenyl group, the naphthyl group, and the phenanthryl group may be preferred substituents.

Even when the aromatic ring group substituting for the chrysene ring is a phenyl group, the center of the charge distribution of each of the HOMO and LUMO of a chrysene molecule is present on the chrysene ring as in the case of each of a fluorenyl group, a naphthyl group, and a phenanthryl group. In addition, in this case, the energy gap of the chrysene molecule becomes extremely large. The term "energy gap" refers to a difference between the HOMO level and LUMO level of a compound. This is because of the following reason. Because the singlet energy of the phenyl group is extremely large and the phenyl group has smaller π conjugation than that of each of the three other aromatic ring groups, the expansion of the π conjugation of the entire chrysene compound is small. As described later, it is not preferred that such chrysene compound having an extremely large energy gap be used as a host material for the emission layer.

As is understood from the foregoing, the chrysene compound according to the present invention has a substituent represented by the formula [2] in the chrysene core represented by the general formula [1]. As a result, chemical stability is obtained.

When a blue organic light-emitting device has the chrysene compound according to the present invention as a host material for its emission layer, the energy gap of the chrysene compound is preferably about 3.0 eV, or specifically 3.0±0.2 eV, or more preferably from 3.0 eV to 3.1 eV.

This is because a carrier injection barrier difference between the HOMO or LUMO of the emission layer and the HOMO or LUMO of an organic layer adjacent to the emission layer such as the hole transport layer or electron transport layer is requested to be small. This is also because the host material is requested to have a wider energy gap than that of an emission material that emits blue light, i.e., a guest material in order that energy may be favorably supplied to the guest material.

The chrysene compound according to the present invention can be preferably used as a host material for the emission layer of the blue organic light-emitting device because the compound satisfies an energy gap within any such numerical range.

Next, the fact that a substituent represented by the formula [2] is bonded to the chrysene core at a specific position of the chrysene core is described. As described above, the chrysene compound according to the present invention is a chrysene compound having an energy gap preferred for use as a host material for a blue emission layer.

The numbers of the substitution positions of the chrysene ring are shown below.

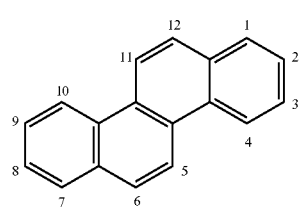 [SMILES: c1ccc2c(c1)ccc1c3ccccc3ccc21]

First, a diaryl-substituted chrysene compound in which two aromatic ring groups substitute for the chrysene ring, or specifically, a 6,12-diaryl chrysene compound has a large energy gap. Accordingly, the compound is still susceptible to improvement in order that the compound may be used as a host material for the blue emission layer.

This is because, even when the two aromatic ring substituents are each changed from a phenyl group to a fluorenyl group, naphthyl group, or phenanthryl group with which a π-conjugated surface additionally expands, the expansion of the π conjugation of the entire chrysene compound is still too small with the substituents alone. The use of the compound as a host for the blue emission layer increases the voltage at which a light-emitting device is driven and reduces the emission efficiency of the device.

In addition, the energy gap of a tetraaryl-substituted chrysene compound in which four aromatic ring groups substitute for the chrysene ring is small. This is because of the following reason. Because the number of aromatic ring substituents is as large as four, the expansion of the π conjugation of the entire chrysene compound becomes excessively large. The compound disqualifies for a host material for a blue organic light-emitting device. The 3,6,9,12-tetraaryl-substituted chrysene derivative in Japanese Patent Application Laid-Open No. 2007-273055 and the 2,6,8,12-tetraaryl-substituted chrysene derivative in Chem. Commun. 2008, 2319 are each mainly used as a guest material for the blue emission layer.

Chem. Commun. 2008, 2319 describes that an organic light-emitting device using 3,6,9,12-tetrakis(4-tert-butylphenyl)chrysene alone in its emission layer has an emission peak wavelength of 450 nm. In consideration of the Stokes shift of a hydrocarbon aromatic polycyclic compound that shows ordinary π-π* type light emission, the energy gap of the chrysene compound in a film state is expected to be at most about 2.95 eV (420 nm in terms of wavelength). Therefore, it can be easily anticipated that, when any such tetraaryl-substituted chrysene compound is used as a host for the blue emission layer, the transfer of an excitation energy to a guest no longer occurs, and hence emission efficiency reduces. That is, the tetraaryl-substituted chrysene compound has too small an energy gap to qualify for a host material for the blue emission layer.

Meanwhile, the triaryl-substituted chrysene compound of the present invention is intermediate in energy gap between the diaryl-substituted chrysene compound and the tetraaryl-substituted chrysene compound because three aromatic ring groups substitute for the chrysene ring. Accordingly, the energy gap is about 3.0 eV, which is preferred in order that the compound may be used as a host material for the blue emission layer. This is because the expansion of the π conjugation of the entire chrysene compound becomes moderate by virtue of the three aromatic ring substituents in order that the compound may be used as a host material for the blue emission layer.

Here, the substitution positions of the three substituents of the triaryl-substituted chrysene compound are discussed.

A dihedral angle between a substituting aromatic ring and the chrysene ring as a core varies largely depending on a position of the chrysene ring to which the substituent is attached. When the structures of compounds in which the respective positions of the chrysene ring are each substituted with a phenyl group as an aromatic ring substituent are optimized by molecular orbital calculation, a dihedral angle between a benzene ring and the chrysene ring is as shown in Table 2 below. It can be said that the dihedral angle in the case where the substitution occurs at the 2- or 3-position is smaller than that in the case where the substitution occurs at any other substitution position.

TABLE 2

| | Structural formula | Dihedral angle |
|---|---|---|
| 1-phenyl-substituted | | 61.2° |
| 2-phenyl-substituted | | 40.5° |
| 3-phenyl-substituted | | 41.9° |
| 4-phenyl-substituted | | 62.6° |
| 5-phenyl-substituted | | 60.9° |
| 6-phenyl-substituted | | 62.2° |

In addition, a small dihedral angle means that the twist of an aromatic ring substituent relative to the chrysene ring is small. In this case, π conjugation on the chrysene ring largely expands toward the substituting aromatic ring, and the expansion leads to a reduction in energy gap of the compound.

Therefore, in the chrysene compound according to the present invention, a third aromatic ring substituent, i.e., $Ar_3$ in the general formula [1] substitutes for the 2- or 3-position of the chrysene ring. As described above, those substitution positions are each such a substitution position that a dihedral angle between a substituting aromatic ring and the chrysene ring becomes small and a twist between the two rings becomes small, and hence the elongation of the π conjugation becomes additionally large. Accordingly, it can be said that any such substitution position is effective in reducing the energy gap of the diaryl-substituted chrysene compound, the energy gap being so large that the compound disqualifies for a host material for the blue emission layer, with the third aromatic ring substituent. In addition, the 3-position of the chrysene ring has a larger narrowing effect on the energy gap than that of the 2-position of the ring.

Further, when the third aromatic ring substituent substitutes for any one of the 2- and 3-positions of the chrysene ring of the chrysene compound according to the present invention, linearly long π conjugation is formed by the substituting aromatic ring and the chrysene ring. Such π conjugation is effective in improving carrier transport property. Therefore, when the chrysene compound of the present invention is used as a host material for an emission layer, carriers are efficiently supplied from both carrier transport layers, and improving effects on the efficiency and life of a light-emitting device can be sufficiently expected.

Meanwhile, a small dihedral angle and a small twist between the chrysene ring and the third substituting aromatic ring improve the planarity of an entire molecule of the chrysene compound. Accordingly, a stack due to an intermolecular interaction may be remarkable. The case where a stack between molecules, or in particular, between host molecules occurs in an organic light-emitting device is not preferred because an efficient transfer of an excitation energy from a host to a guest is no longer performed owing to, for example, the formation of an excimer between the host molecules, and a reduction in emission efficiency of the light-emitting device may occur.

However, in the triaryl-substituted chrysene compound according to the present invention, a substituted or unsubstituted, hydrocarbon aromatic ring group is introduced into each of the 6- and 12-positions of the chrysene ring, i.e., $Ar_1$ and $Ar_2$ in the general formula [1]. As a result, such intermolecular stack can be avoided because of the following reason. That is, as described above, the aromatic ring group substituting for the 6-position of the chrysene ring has a large dihedral angle relative to the chrysene ring by virtue of steric repulsion from a peri-position atom at the 7-position of the chrysene ring, and hence the aromatic ring group serves as a hindrance group for an interaction between the chrysene rings of molecules.

Such hindrance group for reducing the stack is preferably a hydrocarbon aromatic ring group like the present invention rather than a bulky alkyl group. The reason for the foregoing is as described below. A large quantity of charge of an HOMO and an LUMO directly involved in the emission process is distributed on the chrysene ring, and hence a substituent in which sp2 carbons are directly bonded to each other like an aromatic ring substituent is advantageous in terms of energy.

By the way, according to Table 2, the 1-, 4-, and 5-positions of the chrysene ring where large dihedral angles are similarly obtained are also each a possible substitution position of such hindrance group. However, when an aromatic ring substitutes for the 4-position of the chrysene ring, the atom at the 5-position of the chrysene ring sterically interferes with the aromatic ring surface of the substituting aromatic ring, and hence the chrysene ring itself as a core is distorted. Such distortion of the chrysene ring is not preferred because the distortion reduces the structural stability of a molecule of the compound. The case where an aromatic ring substitutes for the 5-position of the chrysene ring is not preferred either because the chrysene ring is distorted by steric interference by the atom at the 4-position of the chrysene ring.

On the other hand, even when an aromatic ring substitutes for the 6-position of the chrysene ring, the above-mentioned steric repulsion from the peri-position atom at the 7-position of the chrysene ring does not distort the chrysene ring itself. The same holds true for steric repulsion from a peri-position atom at the 1-position of the chrysene ring when an aromatic ring substitutes for the 12-position of the chrysene ring.

When an aromatic ring substitutes for the 1-position of the chrysene ring, steric repulsion from a peri-position atom at the 12-position of the chrysene ring does not distort the chrysene ring either. However, the closer to the center of the chrysene ring the position for which an aromatic ring substitutes, the more effective the function of the aromatic ring as a hindrance group for avoiding the intermolecular stack. Accordingly, it can be said that the 6- and 12-positions that are close to the center are each an optimum substitution position of such hindrance group. Further, the 6- and 12-positions of the chrysene ring are each a substitution position into which an aromatic ring group can be easily introduced in a synthesis reaction such as a bromination reaction. Accordingly, in that sense as well, the positions are each more preferably a substitution position of the above-mentioned hindrance group.

In view of the foregoing, the triaryl-substituted chrysene compound according to the present invention is one of a 2,6,12-triaryl chrysene compound and a 3,6,12-triaryl chrysene compound.

When aromatic ring substituents are introduced into two or more of the 2-, 3-, 8-, and 9-positions of the chrysene ring as positions where small dihedral angles are obtained in addition to the aromatic ring substituents at the 6- and 12-positions of the chrysene ring, the energy gap becomes excessively small. Therefore, a triaryl-substituted chrysene compound in which the third aromatic ring substituent is introduced into the 2-position alone or the 3-position alone is an optimum host material for the blue emission layer. In addition, the first and second aromatic ring substituents at the 6- and 12-positions of the chrysene ring are each a substituent needed when the suppression of the intermolecular stack and the stability of a molecule of the compound are taken into consideration. That is, the triaryl-substituted chrysene compound according to the present invention has such an optimum energy gap as to be used as a host material for the blue emission layer, and has all of chemical stability such as oxidation resistance, such structural stability as to be free of distortion, and an ability to suppress the intermolecular stack at the same time.

In addition, further, the entire molecular structure of the triaryl-substituted chrysene compound according to the present invention can be provided with larger asymmetry than that of each of the above-mentioned diaryl-substituted chrysene compound and the tetraaryl-substituted chrysene compound. The large asymmetry allows the triaryl-substituted chrysene compound according to the present invention to have low crystallinity and high amorphous property. It can be generally said that a compound having a high glass transition temperature has high amorphous property. The triaryl-substituted chrysene compound of the present invention has a glass transition temperature of 140° C. or higher. In other words, the compound has a higher glass transition temperature than that of the diaryl-substituted chrysene compound in which only the 6- and 12-positions of the chrysene ring are each substituted with an aryl group. A possible reason for the foregoing is as described below. The symmetry of a molecule of the compound is lost by the introduction of the third aromatic ring substituent into the 2- or 3-position of the chrysene ring. As a result, the compound has more conspicuous amorphous property than its crystallinity, and hence high glass property is obtained. Therefore, when the compound is used in the organic light-emitting device, a stable amorphous film is maintained even in an driving device, which may have an alleviating effect on the degradation of the light emission of the device.

By the way, as described above, the chrysene compound according to the present invention has good carrier transport property, and hence the compound is preferably incorporated into the electron transport layer that transports an electron from the cathode to the adjacent emission layer. In particular, the chrysene compound according to the present invention has a relatively deep HOMO level (a relatively large ionization potential), and hence hole blocking property is also showed when the compound is used in the electron transport layer. As a result, a hole as a carrier can be trapped in the emission layer, and the emission efficiency of the device can be improved. In particular, some of the chrysene compounds according to the present invention can each be preferably used in the electron transport layer even when the compounds each have somewhat too large an energy gap to be used as a host material for the blue emission layer. Any such compound has a larger energy gap than that of the adjacent emission layer, and hence the exciton blocking property, hole blocking property, or the like of the compound is good. As a result, the emission efficiency of the device becomes additionally high.

Specific examples of such chrysene compound include the Exemplified Compound C700 group and Exemplified Compound C800 group shown above. An effect common to those compounds is that a dihedral angle between the chrysene ring and the aromatic ring substituting for each of the b- and 12-positions of the chrysene ring is so large that the rings are substantially perpendicular to each other, π conjugation between the chrysene ring and the substituting aromatic ring is cut, and the energy gap of a compound is large.

The aromatic ring substituent that exerts the above-mentioned effect is, for example, a naphthalen-1-yl group. This is because, when the naphthalen-1-yl group substitutes for the 6-position of the chrysene ring, the chrysene ring and the naphthalene ring are substantially perpendicular to each other by virtue of large steric repulsion between the hydrogen atom at the 7-position of the chrysene ring and the peri-position hydrogen atom at the 8-position of the naphthalene ring. Similarly, even when the 6-position of the chrysene ring is substituted with a fluoren-4-yl group or phenanthren-9-yl group, the chrysene ring and the substituting aromatic ring are substantially perpendicular to each other, and hence a similar expanding effect on the energy gap is obtained. In this case, it is each of the hydrogen atom at the 5-position of the fluorene ring and the hydrogen atom at the 8-position of the phenanthrene ring that undergoes large steric repulsion with the hydrogen atom at the 7-position of the chrysene ring.

On the other hand, in each of the Exemplified Compound C100 group and Exemplified Compound C500 group, an aromatic ring substituent which is free of such steric repulsion as described above and which does not have a large dihedral angle relative to the chrysene ring is introduced into each of the 6- and 12-positions of the chrysene ring, and the third aromatic ring substituent is introduced into the 2-position of the chrysene ring. Therefore, as described above, the energy gap of each of the compounds falls within such a range that the compound is preferably used as a host material for the blue emission layer. In addition, at the same time, the energy gap is of such magnitude that the compound can exert sufficient exciton blocking property even when used as a material for the electron transport layer. Accordingly, the Exemplified Compound C100 group and Exemplified Compound C500 group can each be preferably used as each of both a host material for the blue emission layer and a material for the electron transport layer.

Similarly, the Exemplified Compound C200 group and Exemplified Compound C600 group can each be preferably used as each of both a host material for the blue emission layer and a material for the electron transport layer. Further, the energy gap of each of the compounds is apt to be relatively small because the third aromatic ring substituent is introduced into the 3-position of the chrysene ring having a large narrowing effect on the energy gap. Accordingly, exciton blocking property may be insufficient, and hence the compounds are each more preferably used as a host material for the blue emission layer.

Further, similarly, the Exemplified Compound C300 group and Exemplified Compound C400 group can each be preferably used as each of both a host material for the blue emission layer and a material for the electron transport layer. In particular, a compound in which a methyl group and an alkoxy group serving as electron-donating groups are directly introduced into the chrysene ring is a compound having an additionally shallow HOMO level, and hole injectability from the hole transport layer is expected to be large when the compound is used as a host material for the blue emission layer. In addition, a compound in which a halogenated alkyl group serving as an electron-withdrawing group is directly introduced into the chrysene ring is a compound having an additionally deep HOMO level, and hole blocking property is expected to be large when the compound is used as a material for the electron transport layer.

In addition, the chrysene compound according to the present invention is preferably subjected to sublimation purification as purification immediately before its use in an organic light-emitting device. This is because the sublimation purification exerts a large purifying effect in an increase in purity of the organic compound. Such sublimation purification generally requires a higher temperature as the molecular weight of the organic compound increases. In this case, thermal decomposition or the like is apt to occur owing to the high temperature. Therefore, the organic compound used in the organic light-emitting device has a molecular weight of preferably 1000 or less so that the sublimation purification can be performed without any excessive heating.

As described above, the organic light-emitting device of the present invention is such that at least one kind of chrysene compound of the present invention is incorporated into the layer formed of the organic compound. In addition, the chrysene compound of the present invention is preferably used as a host material for the emission layer of a blue light-emitting device or a material for the electron transport layer of the device, but its applications are not limited to the foregoing. A specific example of the other applications is as described below. The compound may be used as, for example, a host material in the emission layer of a green light-emitting device.

Specific compounds each of which is preferably used as a guest material for a blue light-emitting device when the chrysene compound according to the present invention is used as a host material for the emission layer of the blue light-emitting device are shown below.

(Blue Light-Emitting Guest Materials)

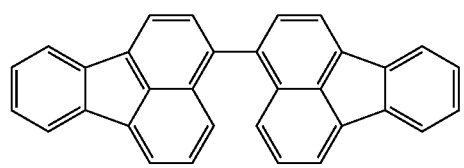

BD-1

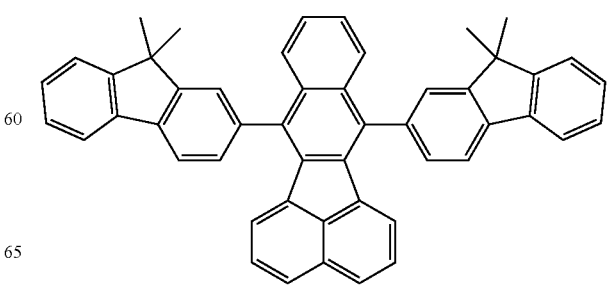

BD-2

BD-3
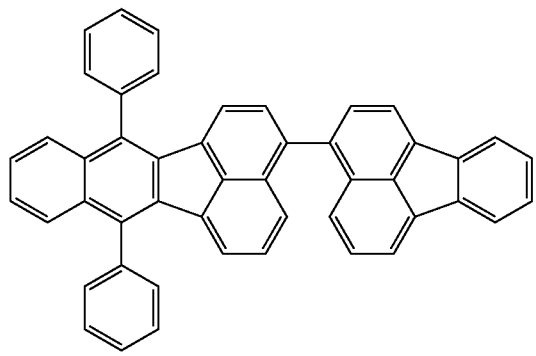
BD-4
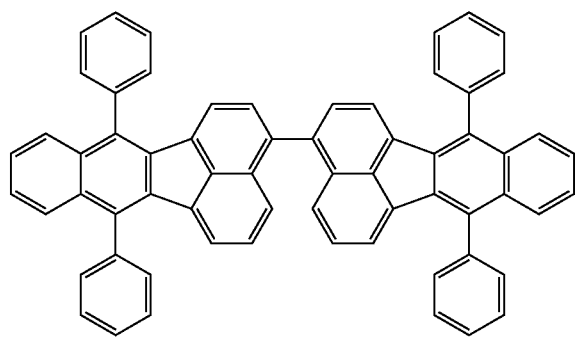
BD-5
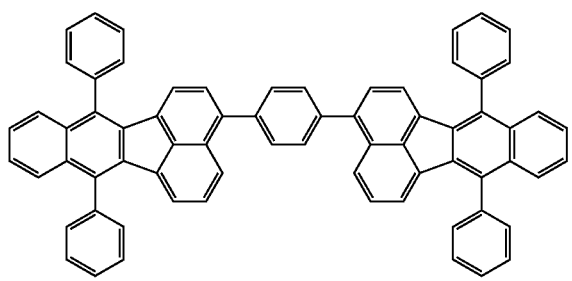
BD-6
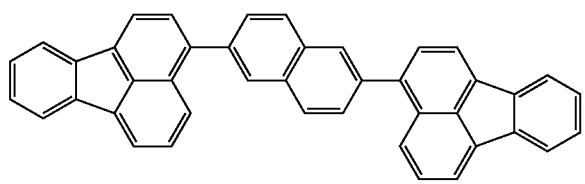
BD-7
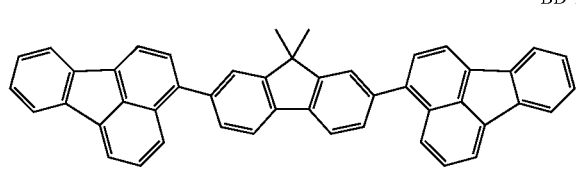
BD-8
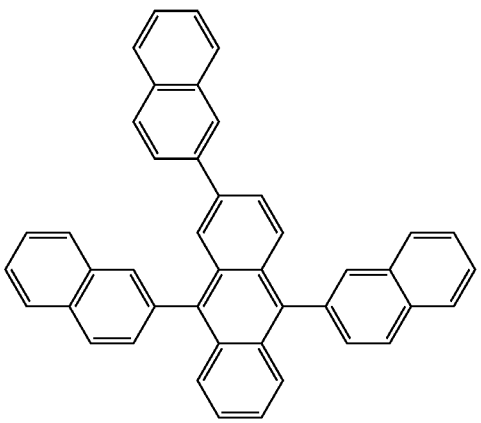
BD-9
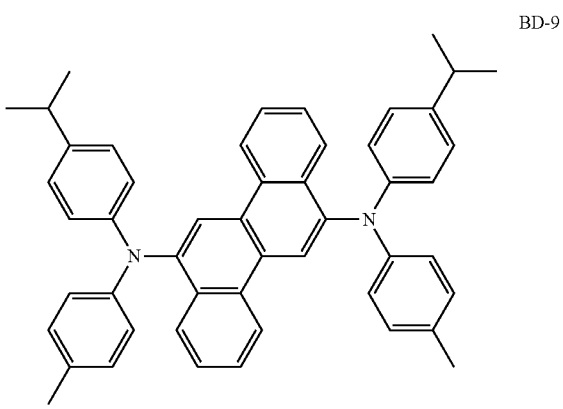
BD-10
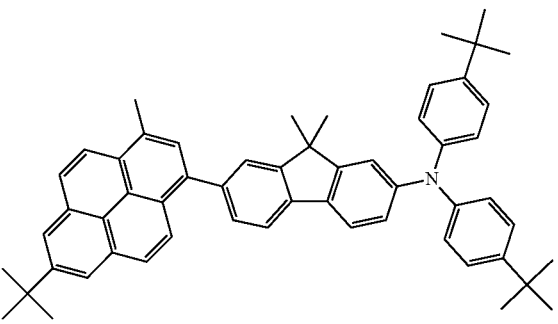
BD-11
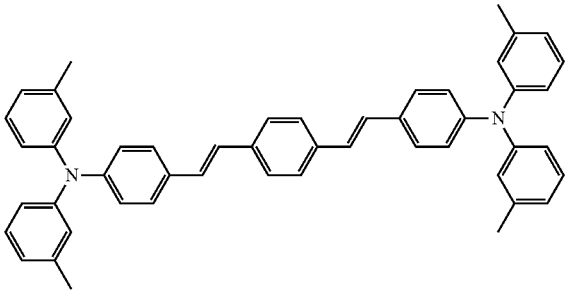

BD-12

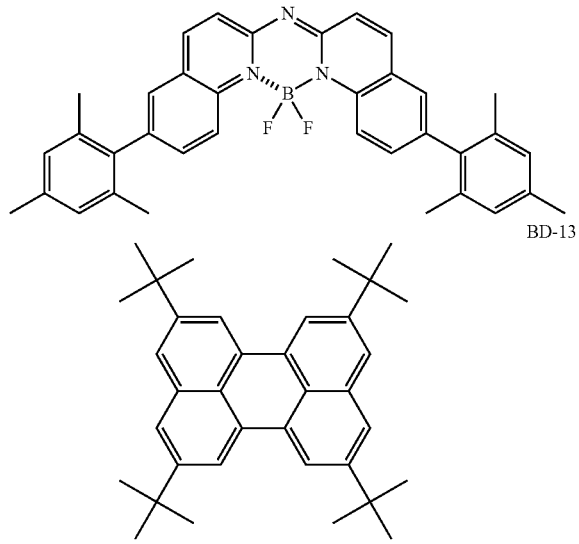

BD-13

Alternatively, the chrysene compound according to the present invention may be used as a guest material for the emission layer.

Further, the chrysene compound according to the present invention may be used in any one of the respective layers except the emission layer, i.e., the hole injection layer, the hole transport layer, the hole blocking layer, the exciton blocking layer, the electron transport layer, and the electron injection layer.

Here, in the organic light-emitting device according to the present invention, there can be used together the following conventionally known compound as required, in addition to the chrysene compound according to the present invention: a low-molecular or high-molecular hole transport compound, a light-emitting compound, an electron transport compound, or the like.

Those compounds are exemplified below.

A hole injection/transport material is preferably a material having a high hole mobility to facilitate the injection of a hole from an anode and to transport the injected hole to an emission layer. As low-molecular and high-molecular materials having hole injection/transport properties, there are exemplified a triarylamine derivative, a phenylene diamine derivative, a stilbene derivative, a phthalocyanine derivative, a porphyrin derivative, poly(vinylcarbazole), poly(thiophene), and other conductive polymers.

As an emission material mainly involved in the emission function, in addition to the above-mentioned blue light-emitting guest material and derivatives thereof, there are exemplified: fused ring compounds (such as fluorene derivatives, naphthalene derivatives, pyrene derivatives, perylene derivatives, tetracene derivatives, anthracene derivatives, and rubrene); quinacridone derivatives; coumarin derivatives; stilbene derivatives; organic aluminum complexes such as tris(8-quinolinolato)aluminum; organic beryllium complexes; and polymer derivatives such as poly(phenylene vinylene) derivatives, poly(fluorene) derivatives, and poly(phenylene) derivatives.

The electron injection/transport material may be arbitrarily selected from compounds each of which facilitates the injection of an electron from a cathode and is capable of transporting the injected electron to the emission layer. In addition, the material is selected in consideration of, for example, a balance with the hole mobility of the hole injection/transport material. As materials having electron injection/transport properties, there are exemplified an oxadiazole derivative, an oxazole derivative, a pyrazine derivative, a triazole derivative, a triazine derivative, a quinoline derivative, a quinoxaline derivative, a phenanthroline derivative, and organic aluminum complexes.

As an anode material, a material having as large a work function as possible is preferred. Examples of the material which may be used include: metal elements such as gold, platinum, silver, copper, nickel, palladium, cobalt, selenium, vanadium, and tungsten, and alloys including a combination of those metal elements; and metal oxides such as tin oxide, zinc oxide, indium oxide, indium tin oxide (ITO), and indium zinc oxide. Further, conductive polymers such as polyaniline, polypyrrole, and polythiophene may also be used. Each of those electrode substances may be used alone, or two or more kinds thereof may be used in combination. Further, the anode may be formed of a single layer, or may be formed of multiple layers.

On the other hand, as a cathode material, a material having a small work function is preferred. Examples of the material include: alkali metals such as lithium; alkali earth metals such as calcium; and metal elements such as aluminum, titanium, manganese, silver, lead, and chromium. Alternatively, alloys including a combination of those metal elements may also be used. For example, magnesium-silver, aluminum-lithium, and aluminum-magnesium can be used. Metal oxides such as indium tin oxide (ITO) may also be used. One kind of electrode substance may be used alone or two or more kinds thereof may be used in combination. Further, the cathode may be formed of a single layer, or may be formed of multiple layers.

Examples of the substrate to be used in the organic light-emitting device of the present invention include, but are not particularly limited to: opaque substrates such as metallic substrates and ceramic substrates; and transparent substrates such as glass, quartz, and plastic sheet substrates. In addition, a color filter film, a fluorescent color conversion filter film, a dielectric reflection film, or the like may be used in the substrate to control emission color.

It should be noted that a protective layer or a sealing layer may be formed on the prepared device to prevent the device from contacting oxygen, moisture, or the like. Examples of the protective layer include a diamond thin film, a film made of an inorganic material such as a metal oxide or a metal nitride, a polymer film made of a fluorine resin, polyethylene, a silicone resin, a polystyrene resin, or the like, and a photo-curing resin. Further, the device itself can be covered with glass, a gas-impermeable film, a metal, or the like and packaged with an appropriate sealing resin. Moreover, with respect to a direction of extracting light from the device, both a bottom emission structure (structure in which light is extracted from the substrate side) and a top emission structure (structure in which light is extracted from a side opposite to the substrate) may be adopted.

In the organic light-emitting device of the present invention, a layer containing the chrysene compound of the present invention and a layer formed of another organic compound are formed by a method described below. Specifically, a thin film is formed by a vacuum evaporation method, an ionization-assisted evaporation method, a sputtering method, or a plasma method, or the thin film may be formed by dissolving the compound in an appropriate solvent and subjecting the resultant to a coating method (e.g., a spin coating method, a dipping method, a casting method, an LB method, or an ink jet method). Here, when the layer is formed by the vacuum evaporation method, a solution coating method, or the like, the layer hardly undergoes crystallization or the like, and is excellent in stability over time. In addition, in film formation by the coating method, the film may be formed by using a compound in combination with an appropriate binder resin.

Examples of the above-mentioned binder resin include, but are not limited to, a polyvinylcarbazole resin, a polycarbonate resin, a polyester resin, an ABS resin, an acrylic resin, a polyimide resin, a phenol resin, an epoxy resin, a silicone resin, and a urea resin. In addition, as a homopolymer or a copolymer, one kind of binder resin may be used alone or a mixture of two or more kinds may be used. Further, a known additive such as a plasticizer, an antioxidant, or a UV absorber, as required, may be used in combination.

The organic light-emitting device of the present invention can be applied to products which require energy saving and high luminance. Examples of the application include a display apparatus such as a flat panel display, a light source for a photosensitive member of an electrophotographic image-forming apparatus such as a laser beam printer, lighting equipment, and a backlight of a liquid crystal display apparatus.

The term "display apparatus" comprehends not only an apparatus that displays an image by causing multiple organic light-emitting devices to independently emit light but also an apparatus as, for example, an emission point for informing the anomaly of the above-mentioned apparatus. A digital camera or an electrophotographic image-forming apparatus may have the display apparatus as a display unit.

In addition, a product formed by the following procedure can be provided as an exposure light source for the photosensitive member of an electrophotographic image-forming apparatus such as a laser beam printer. Multiple organic light-emitting devices are arranged in the long axis direction of the photosensitive member in a line fashion, and each of the organic light-emitting devices is adapted so that its light emission can be independently controlled. With such procedure, the apparatus volume of the exposing unit of the image-forming apparatus can be significantly reduced.

Next, an active matrix type display apparatus using the organic light-emitting device according to the present invention is described with reference to the drawing. The display apparatus includes the organic light-emitting devices and units for supplying electrical signals to the organic light-emitting devices.

FIG. 1 is a schematic sectional view of a display apparatus according to this embodiment. A display apparatus 3 has multiple organic light-emitting devices on a substrate 31. Two organic light-emitting devices are illustrated in the FIGURE. The organic light-emitting devices each have an anode 311, an organic layer 312, and a cathode 313.

The substrate 31 is, for example, a glass plate.

The substrate 31 is provided with a moisture-proof film 32. The moisture-proof film 32 is provided for protecting a member to be formed on the substrate (a TFT or the organic layer). A material of which the moisture-proof film 32 is formed is, for example, silicon oxide or a composite of silicon oxide and silicon nitride. A gate electrode 33 which each of two TFTs has is provided on the moisture-proof film 32. The gate electrode can be obtained by providing a metal such as Cr on the moisture-proof film 32 by sputtering, and patterning the metal.

A gate insulation film 34 is provided to cover the gate electrode 33. The gate insulation film 34 is obtained by forming silicon oxide or the like into a film by, for example, a plasma CVD method or a catalytic chemical vapor deposition method (cat-CVD method), and patterning the film.

A semiconductor layer 35 is provided on the gate insulation film 34. The semiconductor layer 35 is obtained by forming a silicon film by a plasma CVD method or the like (annealing is performed at a temperature of 290° C. or higher in some cases), and patterning the film.

Further, the semiconductor layer 35 is provided with a drain electrode 36 and a source electrode 37. Thus, two TFT devices 38 as switching devices are illustrated in the FIGURE.

The respective switching devices are connected to the respective organic light-emitting devices in correspondence with the organic light-emitting devices. The switching devices each switch the emission and non/emission of the organic light-emitting device. In the FIGURE, the source electrode 37 of each of the TFT devices 38 as switching devices is connected to the anode 311 of the organic light-emitting device through a contact hole 310.

The TFT devices 38 are each covered with an insulation film 39.

The insulation films 39 not only cover the two TFT devices but also have flat upper surfaces. The organic light-emitting devices are provided on the insulation films 39.

The number of the organic layers 312 may be two or more, or may be one. The FIGURE further illustrates a first protective layer 314 and a second protective layer 315 for preventing the degradation of each organic light-emitting device.

The switching devices in the display apparatus according to this embodiment are not particularly limited, and a single-crystal silicon substrate, MIM device, a-Si type device, or the like may be used.

EXAMPLES

Example 1

Synthesis of Exemplified Compound C101

(1) Synthesis of 2-chlorochrysene

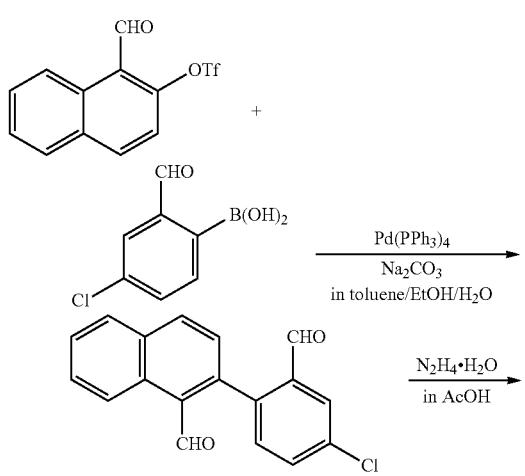

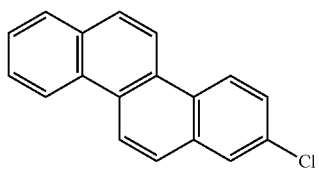

First, 1-formylnaphthalen-2-yl-trifluoromethanesulfonic acid was synthesized from 2-hydroxy-1-naphthaldehyde. In addition, 4-chloro-2-formylphenylboronic acid was synthesized from 2-bromo-5-chlorobenzaldehyde.

The following reagents and solvents were placed in a 300-mL three-necked flask.

| | |
|---|---|
| 1-formylnaphthalen-2-yl-trifluoromethanesulfonic acid: | 9.97 g (32.8 mmol) |
| 4-chloro-2-formylphenylboronic acid: | 5.75 g (31.2 mmol) |
| Tetrakis(triphenylphosphine)palladium(0): | 1.0 g (0.86 mmol) |
| Toluene: | 100 mL |
| Ethanol: | 50 mL |
| 10-wt % aqueous solution of sodium carbonate: | 50 mL |

The reaction solution was heated under reflux for 3 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:toluene/heptane=2/1). Thus, 6.55 g of 2-(4-chloro-2-formylphenyl)-1-naphthaldehyde were obtained (in 71% yield).

Subsequently, the following reagent and solvent were placed in a 500-mL three-necked flask provided with a dropping funnel.

| | |
|---|---|
| 2-(4-chloro-2-formylphenyl)-1-naphthaldehyde: | 6.55 g (22.2 mmol) |
| Acetic acid: | 350 mL |

The reaction solution was heated under reflux under nitrogen with stirring. A solution prepared by mixing 30 mL of acetic acid with 1.45 g (28.9 mmol) of hydrazine monohydrate was slowly dropped from the dropping funnel to the reaction solution over 50 minutes. After the completion of the dropping, the mixture was continuously heated under reflux for additional 3.5 hours. After the completion of the reaction, 100 mL of water were added to the reaction solution, and the mixture was stirred. The precipitated product was separated by filtration, and was then purified by dispersion washing under heat with a mixed solvent of methanol and acetone. Thus, 4.44 g of 2-chlorochrysene were obtained (in 76% yield).

In addition, the resultant compound was identified by $^1$H-NMR analysis.

($^1$H-NMR (400 MHz, CDCl$_3$))

δ 8.75 (d, 1H), 8.73 (d, 1H), 8.68 (d, 1H), 8.62 (d, 1H), 8.01 (d, 1H), 7.99 (dd, 1H), 7.95 (d, 1H), 7.90 (d, 1H), 7.74 (td, 1H), 7.64 (m, 2H).

(2) Synthesis of 6,12-dibromo-2-chlorochrysene

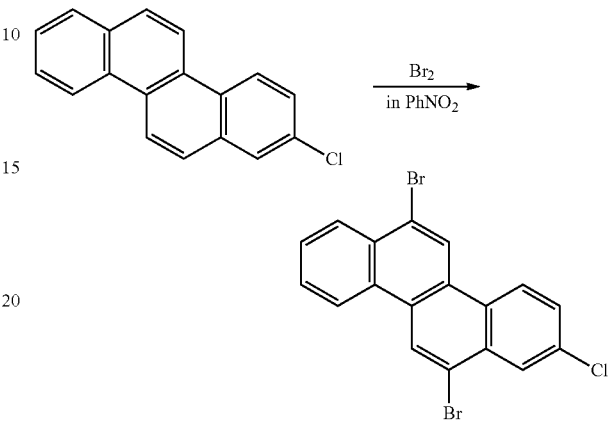

The following reagent and solvent were placed in a 300-mL three-necked flask provided with a dropping funnel.

| | |
|---|---|
| 2-chlorochrysene: | 4.10 g (15.6 mmol) |
| Nitrobenzene: | 170 mL |

The reaction solution was heated to 105° C. under nitrogen with stirring. A solution prepared by mixing 30 mL of nitrobenzene with 1.8 mL (34.9 mmol) of bromine was slowly dropped from the dropping funnel to the reaction solution over 10 minutes. After the completion of the dropping, the mixture was continuously heated for an additional 3.5 hours. After the completion of the reaction, 50 mL of methanol were added to the reaction solution, and the mixture was stirred. The precipitated crystal was separated by filtration, and was then washed with methanol, ethanol, and hexane. The resultant crystal was purified by recrystallization from toluene. Thus, 5.94 g of 6,12-dibromo-2-chlorochrysene were obtained (in 84% yield).

In addition, the resultant compound was identified by $^1$H-NMR analysis.

($^1$H-NMR (400 MHz, CDCl$_3$))

δ 9.01 (s, 1H), 8.91 (s, 1H), 8.67 (d, 1H), 8.61 (d, 1H), 8.50-8.35 (m, 2H), 8.77-8.73 (m, 3H).

(3) Synthesis of Intermediate Cl-204

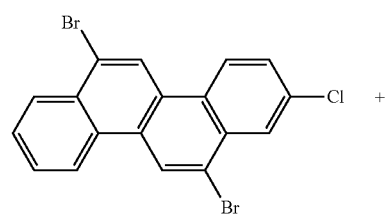 +

-continued

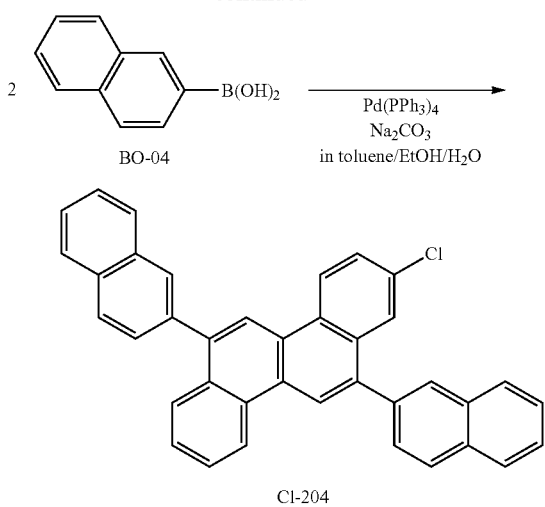

The following reagents and solvents were placed in a 200-mL recovery flask.

| | |
|---|---|
| 6,12-dibromo-2-chlorochrysene: | 1.50 g (3.57 mmol) |
| Boronic acid compound BO-04: | 1.29 g (7.49 mmol) |
| Tetrakis(triphenylphosphine)palladium(0): | 0.20 g (0.17 mmol) |
| Toluene: | 50 mL |
| Ethanol: | 25 mL |
| 10-wt % aqueous solution of sodium carbonate: | 25 mL |

The reaction solution was heated under reflux for 4.5 hours under nitrogen with stirring. After the completion of the reaction, the precipitated crystal was separated by filtration, and was then washed with water, ethanol, and hexane. Thus, a crude product was obtained. Next, the crude product was dissolved in chlorobenzene under heat. After that, the solution was subjected to hot filtration, and was then purified by dispersion washing under heat with a mixed solvent of toluene and heptane. Thus, 1.67 g of Intermediate Cl-204 were obtained (in 91% yield).

(4) Synthesis of Exemplified Compound C101

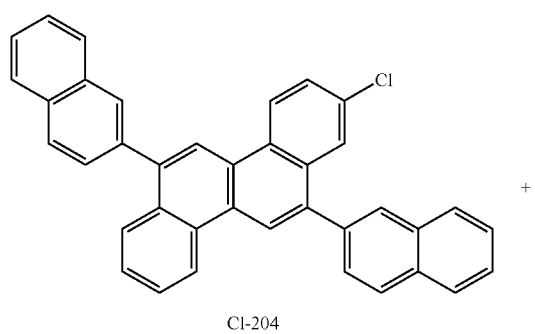

-continued

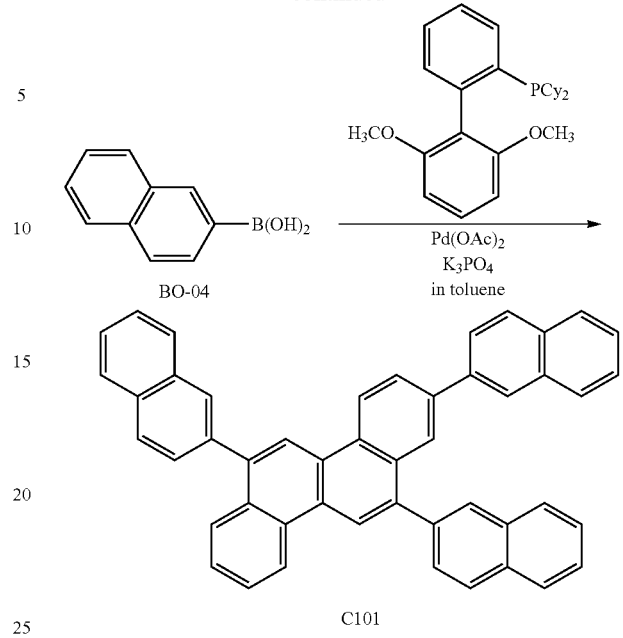

The following reagents and solvents were placed in a 100-mL recovery flask.

| | |
|---|---|
| Intermediate Cl-204: | 800 mg (1.55 mmol) |
| Boronic Acid Compound BO-04: | 320 mg (1.86 mmol) |
| Palladium(II) acetate: | 18 mg (80 µmol) |
| Dicyclohexyl(2',6'-dimethoxybiphenyl-2-yl)phosphine: | 80 mg (194 µmol) |
| Potassium phosphate: | 0.99 g (4.66 mmol) |
| Toluene: | 40 mL |

The reaction solution was heated under reflux for 7 hours with stirring. After the completion of the reaction, the precipitated crystal was separated by filtration, and was then washed with water, ethanol, and acetone. Thus, a crude product was obtained. Next, the crude product was dissolved in toluene under heat. After that, the solution was subjected to hot filtration, and was then recrystallized with toluene and octane. The resultant crystal was vacuum-dried at 150° C., and was then subjected to sublimation purification under conditions of $10^{-4}$ Pa and 360° C. Thus, 518 mg of Exemplified Compound C101 having a high purity were obtained (in 55% yield).

The results of the identification of the resultant compound are shown below.

(MALDI-TOF-MS (Matrix-Assisted Laser Desorption/Ionization Time-of-Flight Mass Spectrometry))

Observed value: m/z=605.99, calculated value: $C_{48}H_{30}$=606.23

($^1$H-NMR (400 MHz, CDCl$_3$))

δ 9.00 (d, 1H), 8.91 (d, 1H), 8.84 (d, 2H), 8.42 (d, 1H), 8.23 (s, 1H), 8.18 (s, 1H), 8.15-7.95 (m, 9H), 7.92-7.70 (m, 7H), 7.65-7.55 (m, 5H), 7.47 (m, 2H).

In addition, the energy gap of Exemplified Compound C101 was measured by the following method.

Exemplified Compound C101 was evaporated from the vapor onto a glass substrate under heat. Thus, an evaporated thin film having a thickness of 20 nm was obtained. The light absorption spectrum of the evaporated thin film was measured with an ultraviolet-visible spectrophotometer (V-560 manufactured by JASCO Corporation). The absorption edge of the resultant light absorption spectrum was determined to be 403 nm, and Exemplified Compound C101 had an energy gap of 3.08 eV.

Further, DSC analysis was conducted on Exemplified Compound C101 with a differential scanning calorimeter (manufactured by PerkinElmer, Inc.). As a result, the compound was found to have a glass transition temperature of 144° C.

Example 2

Synthesis of Exemplified Compound C103

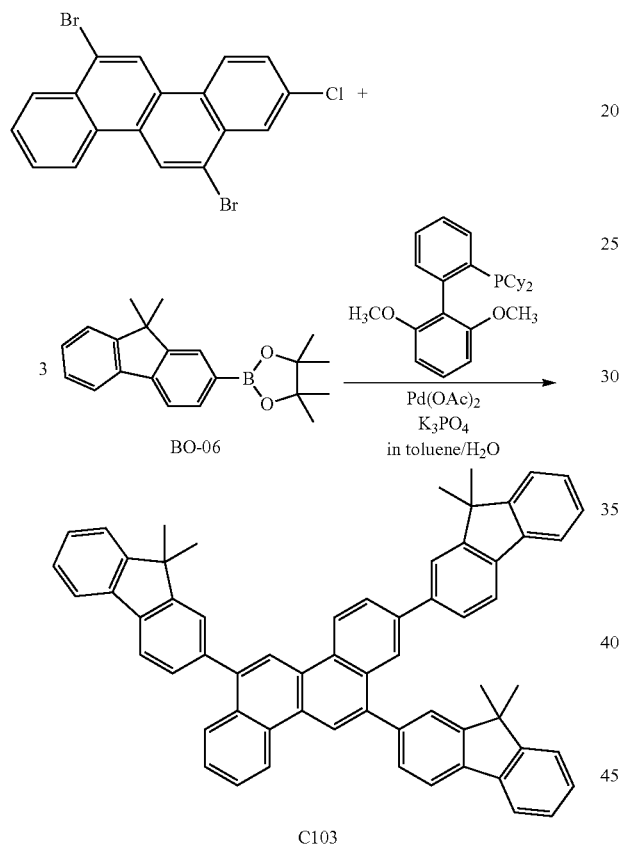

C103

The following reagents and solvents were placed in a 100-mL recovery flask.

| | |
|---|---|
| 6,12-dibromo-2-chlorochrysene: | 400 mg (0.95 mmol) |
| Boronic Acid Compound BO-06: | 1.01 g (3.14 mmol) |
| Palladium(II) acetate: | 22 mg (98 μmol) |
| Dicyclohexyl(2',6'-dimethoxybiphenyl-2-yl)phosphine: | 98 mg (239 μmol) |
| Potassium phosphate: | 606 mg (2.85 mmol) |
| Toluene: | 30 mL |
| Water: | 0.75 mL |

The reaction solution was heated at 100° C. for 33 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:heptane/toluene=3/1). After that, the solution was further recrystallized with a mixed solvent of toluene and heptane. The resultant crystal was vacuum-dried at 150° C., and was then subjected to sublimation purification under conditions of $10^{-4}$ Pa and 370° C. Thus, 473 mg of Exemplified Compound C103 having a high purity were obtained (in 62% yield).

The results of the identification of the resultant compound are shown below.

(MALDI-TOF-MS)

Observed value: m/z=804.40, calculated value: $C_{63}H_{48}$=804.38

($^1$H-NMR (400 MHz, $CDCl_3$))

δ 8.99 (d, 1H), 8.93 (d, 1H), 8.81 (d, 2H), 8.47 (d, 1H), 8.13 (d, 1H), 8.05 (dd, 1H), 7.95 (t, 2H), 7.86 (m, 3H), 7.81-7.57 (m, 9H), 7.53 (m, 2H), 7.50-7.30 (m, 7H), 1.66 (s, 6H), 1.62 (s, 6H), 1.49 (s, 6H).

In addition, the energy gap of Exemplified Compound C103 was measured in the same manner as in Example 1-(4). As a result, the absorption edge of the light absorption spectrum was 405 nm, and Exemplified Compound C103 had an energy gap of 3.06 eV.

Further, DSC analysis was conducted on Exemplified Compound C103 in the same manner as in Example 1-(4). As a result, the compound was found to have a glass transition temperature of 189° C.

Example 3

Synthesis of Exemplified Compound C107

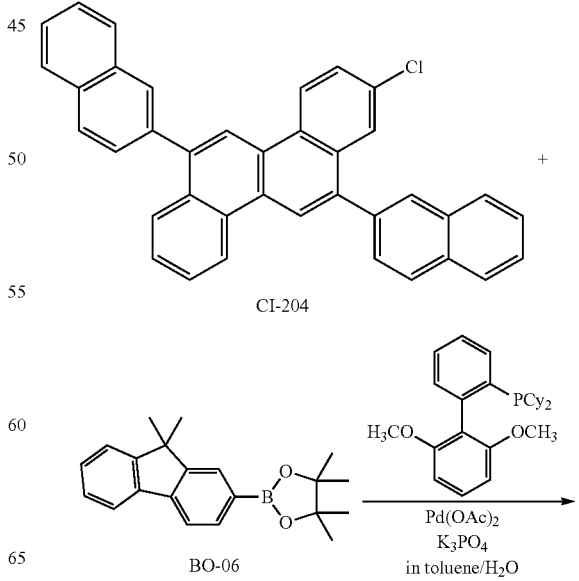

-continued

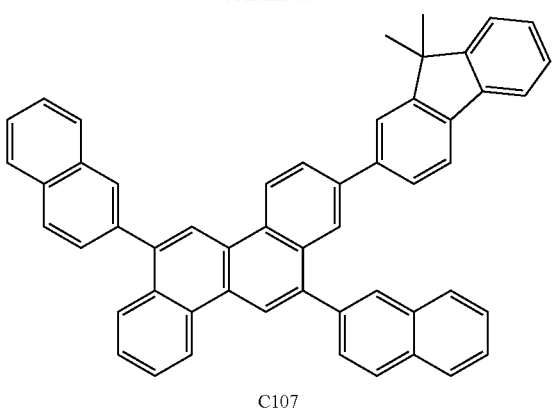

C107

The following reagents and solvents were placed in a 200-mL recovery flask.

| | |
|---|---|
| Intermediate Cl-204: | 1.60 g (3.11 mmol) |
| Boronic Acid Compound BO-06: | 1.05 g (3.26 mmol) |
| Palladium(II) acetate: | 42 mg (186 μmol) |
| Dicyclohexyl(2',6'-dimethoxybiphenyl-2-yl)phosphine: | 191 mg (466 μmol) |
| Potassium phosphate: | 1.98 g (9.32 mmol) |
| Toluene: | 80 mL |
| Water: | 2 mL |

The reaction solution was heated at 100° C. for 5 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:heptane/chloroform=3/1). After that, the solution was further recrystallized with a mixed solvent of toluene and octane. The resultant crystal was vacuum-dried at 150° C., and was then subjected to sublimation purification under conditions of $10^{-4}$ Pa and 370° C. Thus, 0.99 g of Exemplified Compound C107 having a high purity were obtained (in 47% yield).

The results of the identification of the resultant compound are shown below.

(MALDI-TOF-MS)

Observed value: m/z=672.16, calculated value: $C_{53}H_{36}$=672.28

($^1$H-NMR (400 MHz, CDCl$_3$))

δ 8.96 (d, 1H), 8.91 (d, 1H), 8.83 (d, 2H), 8.37 (d, 1H), 8.22 (s, 1H), 8.17 (s, 1H), 8.15-7.94 (m, 8H), 7.87 (dd, 1H), 7.81 (dd, 1H), 7.72 (t, 4H), 7.68-7.51 (m, 6H), 7.43 (m, 1H), 7.32 (m, 2H), 1.50 (s, 6H).

In addition, the energy gap of Exemplified Compound C107 was measured in the same manner as in Example 1-(4). As a result, the absorption edge of the light absorption spectrum was 403 nm, and Exemplified Compound C107 had an energy gap of 3.08 eV.

Further, DSC analysis was conducted on Exemplified Compound C107 in the same manner as in Example 1-(4). As a result, the compound was found to have a glass transition temperature of 161° C.

Example 4

Synthesis of Exemplified Compound C110

(1) Synthesis of Intermediate Cl-206

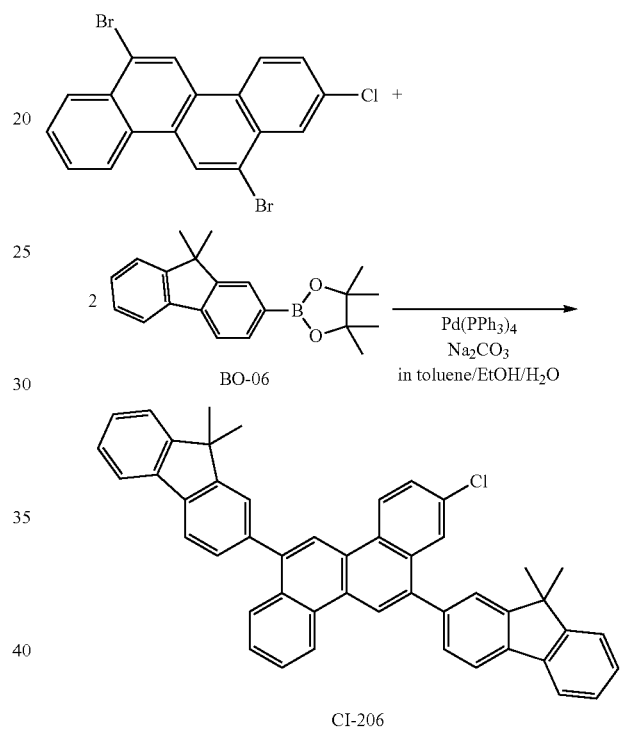

The following reagents and solvents were placed in a 300-mL recovery flask.

| | |
|---|---|
| 6,12-dibromo-2-chlorochrysene: | 2.00 g (4.76 mmol) |
| Boronic Acid Compound BO-06: | 3.20 g (9.99 mmol) |
| Tetrakis(triphenylphosphine)palladium(0): | 165 mg (143 μmol) |
| Toluene: | 80 mL |
| ethanol: | 40 mL |
| 10 wt % aqueous solution of sodium carbonate: | 40 mL |

The reaction solution was heated under reflux for 3 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:heptane/chloroform=4/1). After that, the solution was further purified by dispersion washing under heat with a mixed solvent of heptane and ethanol. Thus, 2.71 g of Intermediate Cl-206 were obtained (in 88% yield).

(2) Synthesis of Exemplified Compound C110

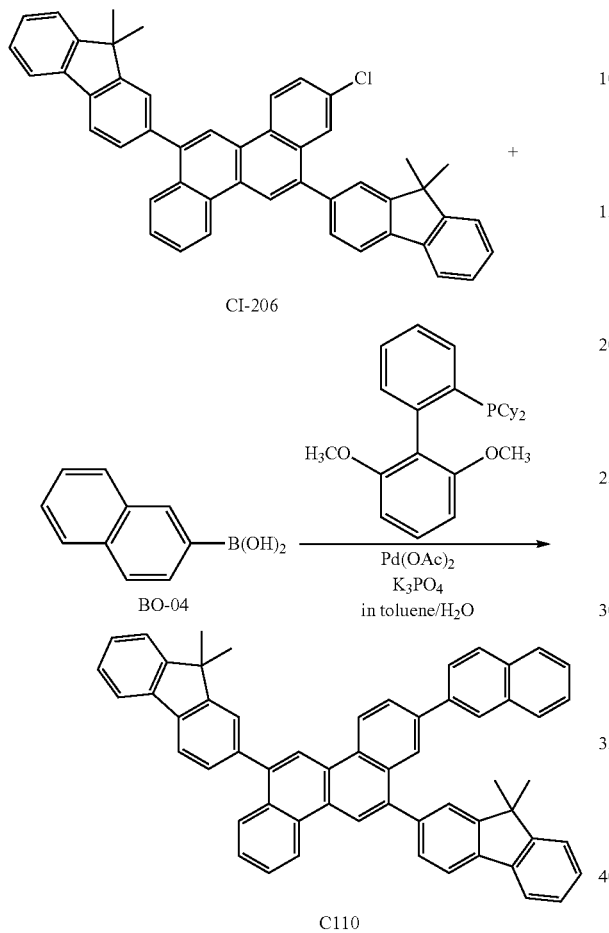

The following reagents and solvents were placed in a 200-mL recovery flask.

| | |
|---|---|
| Intermediate Cl-206: | 1.80 g (2.78 mmol) |
| Boronic Acid Compound BO-04: | 574 mg (3.34 mmol) |
| Palladium(II) acetate: | 62 mg (276 μmol) |
| Dicyclohexyl(2',6'-dimethoxybiphenyl-2-yl)phosphine: | 285 mg (694 μmol) |
| Potassium phosphate: | 1.77 mg (8.34 mmol) |
| Toluene: | 90 mL |

The reaction solution was heated at 105° C. for 16 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:heptane/chloroform=3/1). After that, the solution was purified by dispersion washing under heat with a mixed solvent of heptane and ethyl acetate, and was further recrystallized twice with a mixed solvent of toluene and octane. The resultant crystal was vacuum-dried at 150° C., and was then subjected to sublimation purification under conditions of $10^{-4}$ Pa and 380° C. Thus, 1.24 g of Exemplified Compound C110 having a high purity were obtained (in 60% yield).

(MALDI-TOF-MS)

Observed value: m/z=738.46, calculated value: $C_{58}H_{42}$=738.33

($^1$H-NMR (400 MHz, CDCl$_3$))

δ 9.01 (d, 1H), 8.93 (d, 1H), 8.84 (s, 1H), 8.80 (s, 1H), 8.52 (d, 1H), 8.13 (m, 3H), 7.95 (t, 2H), 7.91-7.78 (m, 7H), 7.78-7.70 (m, 3H), 7.67 (dd, 1H), 7.61 (t, 1H), 7.53 (m, 2H), 7.50-7.32 (m, 6H), 1.67 (s, 6H), 1.62 (s, 6H).

In addition, the energy gap of Exemplified Compound C110 was measured in the same manner as in Example 1-(4). As a result, the absorption edge of the light absorption spectrum was 412 nm, and Exemplified Compound C110 had an energy gap of 3.01 eV.

Further, DSC analysis was conducted on Exemplified Compound C110 in the same manner as in Example 1-(4). As a result, the compound was found to have a glass transition temperature of 181° C.

Example 5

Synthesis of Exemplified Compound C201

(1) Synthesis of 3-chlorochrysene

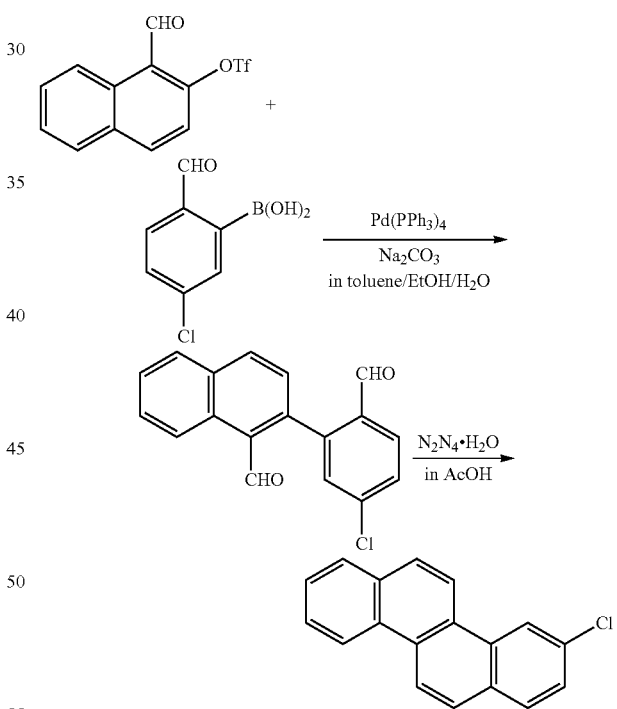

5-chloro-2-formylphenylboronic acid was synthesized from 2-bromo-4-chlorobenzaldehyde.

The following reagents and solvents were placed in a 200-mL recovery flask.

| | |
|---|---|
| 1-formylnaphthalene-2-yl-trifluoromethanesulfonic acid: | 5.37 g (17.7 mmol) |
| 5-chloro-2-formylphenylboronic acid: | 2.96 g (16.1 mmol) |
| tetrakis(triphenylphosphine)palladium (0): | 0.60 g (0.52 mmol) |

| | |
|---|---|
| Toluene: | 60 mL |
| Ethanol: | 30 mL |
| 10 wt % aqueous solution of sodium carbonate: | 30 mL |

The reaction solution was heated under reflux for 7 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:toluene/heptane=5/1). Thus, 2.24 g of 2-(5-chloro-2-formylphenyl)-1-naphthaldehyde were obtained (in 47% yield).

Subsequently, the following reagent and solvent were placed in a 300-mL three-necked flask provided with a dropping funnel.

| | |
|---|---|
| 2-(5-chloro-2-formylphenyl)-1-naphthaldehyde: | 2.05 g (6.96 mmol) |
| Acetic acid: | 160 mL |

The reaction solution was heated under reflux under nitrogen with stirring. A solution prepared by mixing 25 mL of acetic acid with 0.46 g (9.04 mmol) of hydrazine was slowly dropped from the dropping funnel to the reaction solution over 20 minutes. After the completion of the dropping, the mixture was continuously heated under reflux for an additional 5 hours. After the completion of the reaction, 50 mL of water were added to the reaction solution, and the mixture was stirred. The precipitated crystal was separated by filtration, and was then purified by dispersion washing under heat with a mixed solvent of methanol and acetone. Thus, 1.50 g of 3-chlorochrysene were obtained (in 82% yield).

In addition, the resultant compound was identified by $^1$H-NMR analysis.

($^1$H-NMR (400 MHz, CDCl$_3$))
δ 8.78 (d, 1H), 8.75 (d, 1H), 8.72 (d, 1H), 8.61 (d, 1H), 8.05-7.90 (m, 4H), 7.73 (td, 1H), 7.66 (t, 1H), 7.59 (dd, 1H).

(2) Synthesis of 6,12-dibromo-3-chlorochrysene

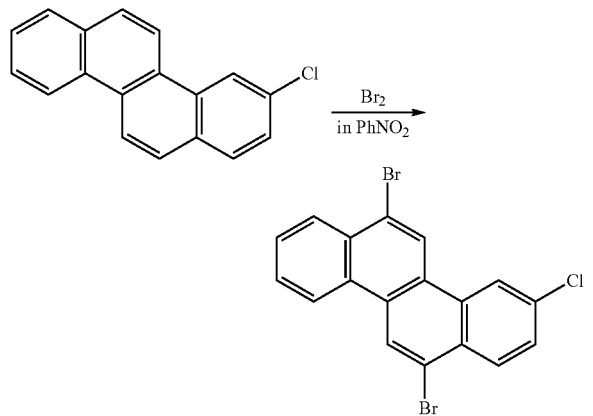

The following reagent and solvent were placed in a 200-mL three-necked flask provided with a dropping funnel.

| | |
|---|---|
| 3-chlorochrysene: | 1.49 g (5.67 mmol) |
| Nitrobenzene: | 65 mL |

The reaction solution was heated to 105° C. under nitrogen with stirring. A solution prepared by mixing 10 mL of nitrobenzene with 0.62 mL (12.0 mmol) of bromine was slowly dropped from the dropping funnel to the reaction solution over 10 minutes. After the completion of the dropping, the mixture was continuously heated for an additional 3.5 hours. After the completion of the reaction, 30 mL of methanol were added to the reaction solution, and the mixture was stirred. The precipitated crystal was separated by filtration, and was then washed with methanol, ethanol, and hexane. The resultant crystal was purified by recrystallization from toluene. Thus, 1.99 g of 6,12-dibromo-3-chlorochrysene were obtained (in 84% yield).

In addition, the resultant compound was identified by $^1$H-NMR analysis.

($^1$H-NMR (400 MHz, CDCl$_3$))
δ 8.99 (s, 1H), 8.89 (s, 1H), 8.75-8.65 (m, 2H), 8.46 (m, 1H), 8.38 (d, 1H), 7.79 (m, 2H), 7.70 (dd, 1H).

(3) Synthesis of Intermediate Cl-304

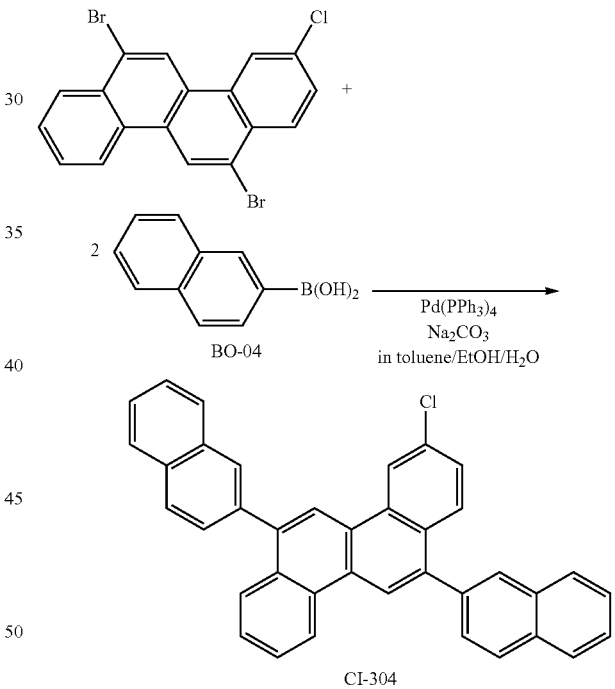

The following reagents and solvents were placed in a 100-mL recovery flask.

| | |
|---|---|
| 6,12-dibromo-3-chlorochrysene: | 0.978 g (2.32 mmol) |
| Boronic acid compound BO-04: | 0.879 g (5.11 mmol) |
| Tetrakis(triphenylphosphine)palladium(0): | 0.134 g (0.116 mmol) |
| Toluene: | 30 mL |
| Ethanol: | 15 mL |
| 10-wt % aqueous solution of sodium carbonate: | 15 mL |

The reaction solution was heated under reflux for 4 hours under nitrogen with stirring. After the completion of the reaction, the precipitated crystal was separated by filtration, and was then washed with water and ethanol. Thus, a crude product was obtained. Next, the crude product was dissolved in chlorobenzene under heat. After that, the solution was subjected to hot filtration, and was then purified by dispersion washing under heat with a mixed solvent of toluene and octane. Thus, 1.10 g of Intermediate Cl-304 were obtained (in 92% yield).

(4) Synthesis of Exemplified Compound C201

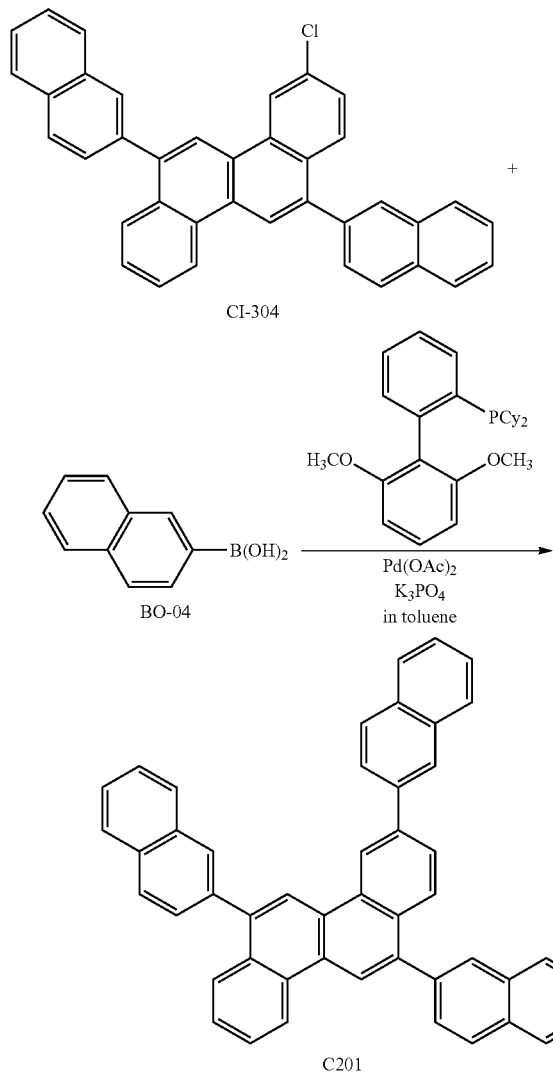

The following reagents and solvents were placed in a 50-mL recovery flask.

| | |
|---|---|
| Intermediate Cl-304: | 600 mg (1.16 mmol) |
| Boronic Acid Compound BO-04: | 241 mg (1.40 mmol) |
| Palladium(II) acetate: | 15 mg (67 μmol) |
| Dicyclohexyl(2',6'-dimethoxybiphenyl-2-yl)phosphine: | 62 mg (151 μmol) |
| Potassium phosphate: | 0.75 g (3.49 mmol) |
| Toluene: | 30 mL |

The reaction solution was heated at 100° C. for 7.5 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:heptane/toluene=3/1). After that, the solution was further recrystallized twice with a mixed solvent of toluene and octane. The resultant crystal was vacuum-dried at 150° C., and was then subjected to sublimation purification under conditions of $10^{-4}$ Pa and 370° C. Thus, 113 mg of Exemplified Compound C201 having a high purity were obtained (in 16% yield).

The results of the identification of the resultant compound are shown below.

(MALDI-TOF-MS)

Observed value: m/z=606.11, calculated value: $C_{48}H_{30}$=606.23

($^1$H-NMR (400 MHz, CDCl$_3$))

δ 9.19 (d, 1H), 8.94 (s, 1H), 8.92 (s, 1H), 8.84 (s, 1H), 8.30-8.15 (m, 4H), 8.15-7.92 (m, 11H), 7.92-7.77 (m, 3H), 7.73 (td, 1H), 7.70-7.55 (m, 5H), 7.50 (m, 2H).

In addition, the energy gap of Exemplified Compound C201 was measured in the same manner as in Example 1-(4). As a result, the absorption edge of the light absorption spectrum was 408 nm, and Exemplified Compound C201 had an energy gap of 3.04 eV.

Further, DSC analysis was conducted on Exemplified Compound C201 in the same manner as in Example 1-(4). As a result, the compound was found to have a glass transition temperature of 144° C.

Example 6

Synthesis of Exemplified Compound C202

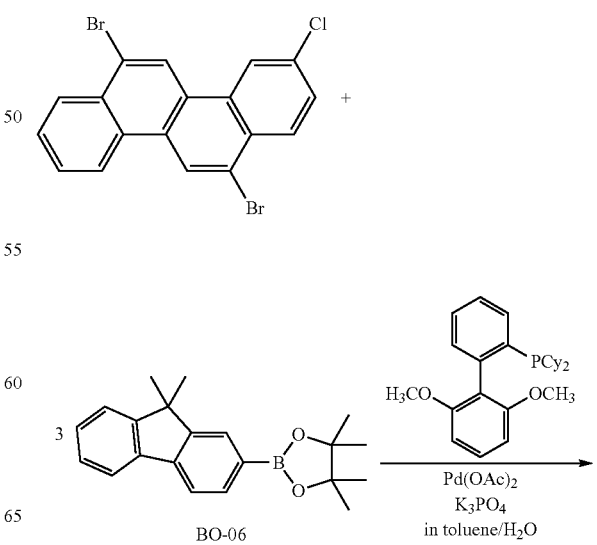

-continued

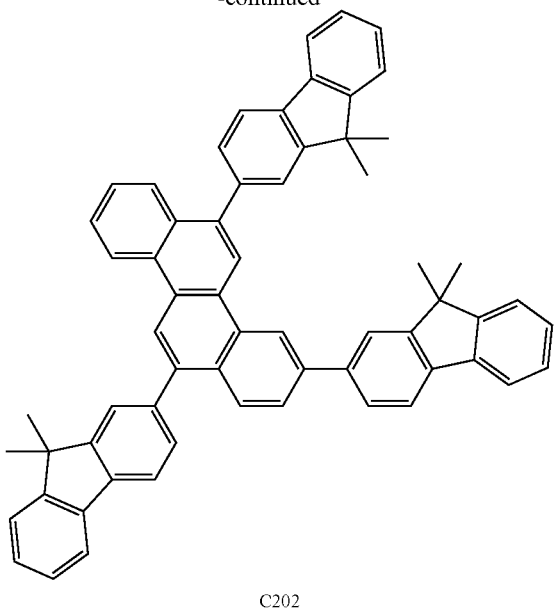

C202

The following reagents and solvents were placed in a 50-mL recovery flask.

| 6,12-dibromo-3-chlorochrysene: | 400 mg (0.95 mmol) |
| Boronic Acid Compound BO-06: | 1.07 g (3.33 mmol) |
| Palladium(II) acetate: | 43 mg (190 μmol) |
| Dicyclohexyl(2',6'-dimethoxybiphenyl-2-yl)phosphine: | 195 mg (476 μmol) |
| Potassium phosphate: | 0.81 g (3.80 mmol) |
| Toluene: | 30 mL |
| Water: | 0.75 mL |

The reaction solution was heated at 100° C. for 12 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:heptane/chloroform=3/1). After that, the solution was further recrystallized with a mixed solvent of toluene and heptane. The resultant crystal was vacuum-dried at 150° C., and was then subjected to sublimation purification under conditions of $10^{-4}$ Pa and 370° C. Thus, 442 mg of Exemplified Compound C202 having a high purity were obtained (in 58% yield).

The results of the identification of the resultant compound are shown below.

(MALDI-TOF-MS)

Observed value: m/z=804.43, calculated value: $C_{63}H_{48}$=804.38

($^1$H-NMR (400 MHz, CDCl$_3$))

δ 9.12 (s, 1H), 8.93 (d, 1H), 8.88 (s, 1H), 8.79 (s, 1H), 8.22 (d, 1H), 8.15 (d, 1H), 8.00-7.50 (m, 15H), 7.51 (t, 2H), 7.49-7.30 (m, 7H), 1.63 (s, 6H), 1.61 (s, 6H), 1.56 (s, 6H).

In addition, the energy gap of Exemplified Compound C202 was measured in the same manner as in Example 1-(4). As a result, the absorption edge of the light absorption spectrum was 412 nm, and Exemplified Compound C202 had an energy gap of 3.01 eV.

Further, DSC analysis was conducted on Exemplified Compound C202 in the same manner as in Example 1-(4). As a result, the compound was found to have a glass transition temperature of 191° C.

Example 7

Synthesis of Exemplified Compound C501

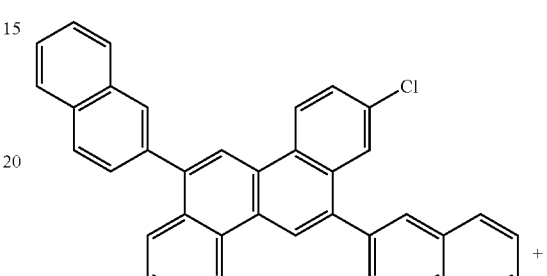

CI-204

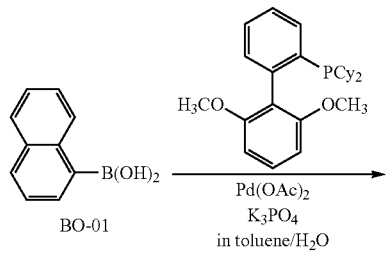

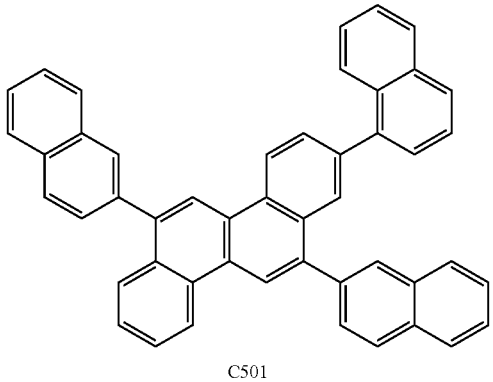

C501

The following reagents and solvents were placed in a 50-mL recovery flask.

| Intermediate Cl-204: | 484 mg (0.94 mmol) |
| Boronic Acid Compound BO-01: | 178 mg (1.03 mmol) |
| Palladium(II) acetate: | 13 mg (56 μmol) |
| Dicyclohexyl(2',6'-dimethoxybiphenyl-2-yl)phosphine: | 58 mg (141 μmol) |
| Potassium phosphate: | 600 mg (2.83 mmol) |
| Toluene: | 24 mL |

The reaction solution was heated at 105° C. for 10 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:heptane/toluene=3/1). After that, the solution was further subjected to dispersion washing under heat with a mixed solvent of acetone and ethanol. The resultant crystal was vacuum-dried at 150° C., and was then subjected to sublimation purification under conditions of $10^{-4}$ Pa and 350° C. Thus, 146 mg of Exemplified Compound C501 having a high purity were obtained (in 26% yield).

The results of the identification of the resultant compound are shown below.

(MALDI-TOF-MS)

Observed value: m/z=606.16, calculated value: $C_{48}H_{30}$=606.23

($^1$H-NMR (400 MHz, CDCl$_3$))

δ 9.00 (d, 1H), 8.92 (d, 1H), 8.87 (d, 2H), 8.35-7.68 (m, 18H), 7.68-7.32 (m, 8H).

In addition, the energy gap of Exemplified Compound C501 was measured in the same manner as in Example 1-(4). As a result, the absorption edge of the light absorption spectrum was 404 nm, and Exemplified Compound C501 had an energy gap of 3.07 eV.

Example 8

Synthesis of Exemplified Compound C505

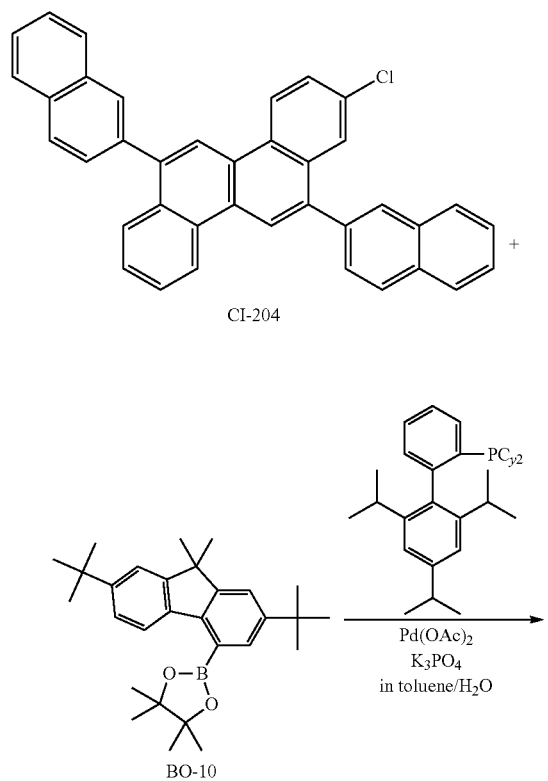

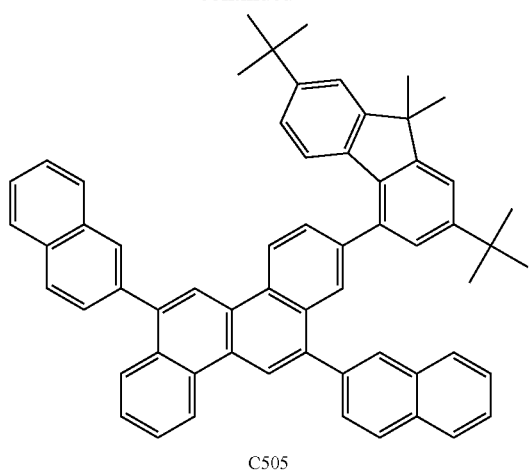

C505

The following reagents and solvents were placed in a 50-mL recovery flask.

| | |
|---|---|
| Intermediate CI-204: | 500 mg (0.97 mmol) |
| Boronic Acid Compound BO-10: | 504 mg (1.17 mmol) |
| Palladium(II) acetate: | 22 mg (97 μmol) |
| Dicyclohexyl(2',4',6'-triisopropylbiphenyl-2-yl)phosphine: | 139 mg (291 μmol) |
| Potassium phosphate: | 618 mg (2.91 mmol) |
| Toluene: | 25 mL |
| Water: | 0.6 mL |

The reaction solution was heated at 100° C. for 6 hours under nitrogen with stirring. After the completion of the reaction, the reaction solution was washed with water and dried over sodium sulfate. Then, the dried product was concentrated. Thus, a crude product was obtained. Next, the crude product was purified by silica gel column chromatography (eluent:heptane/toluene=4/1). After that, the solution was further subjected to dispersion washing under heat with a mixed solvent of ethyl acetate and toluene. The resultant crystal was vacuum-dried at 150° C., and was then subjected to sublimation purification under conditions of $10^{-4}$ Pa and 370° C. Thus, 415 mg of Exemplified Compound C505 having a high purity were obtained (in 54% yield).

The results of the identification of the resultant compound are shown below.

(MALDI-TOF-MS)

Observed value: m/z=784.27, calculated value: $C_{61}H_{52}$=784.41

($^1$H-NMR (400 MHz, CDCl$_3$))

δ 8.99 (d, 1H), 8.94 (d, 1H), 8.88 (d, 2H), 8.28-7.65 (m, 14H), 7.65-7.27 (m, 8H), 7.05 (d, 1H), 6.92 (d, 1H), 1.55 (s, 6H), 1.35 (s, 9H), 1.31 (s, 9H).

In addition, the energy gap of Exemplified Compound C505 was measured in the same manner as in Example 1-(4).

As a result, the absorption edge of the light absorption spectrum was 397 nm, and Exemplified Compound C505 had an energy gap of 3.12 eV.

Example 9

Synthesis of Exemplified Compound C703

(1) Synthesis of Intermediate Cl-201

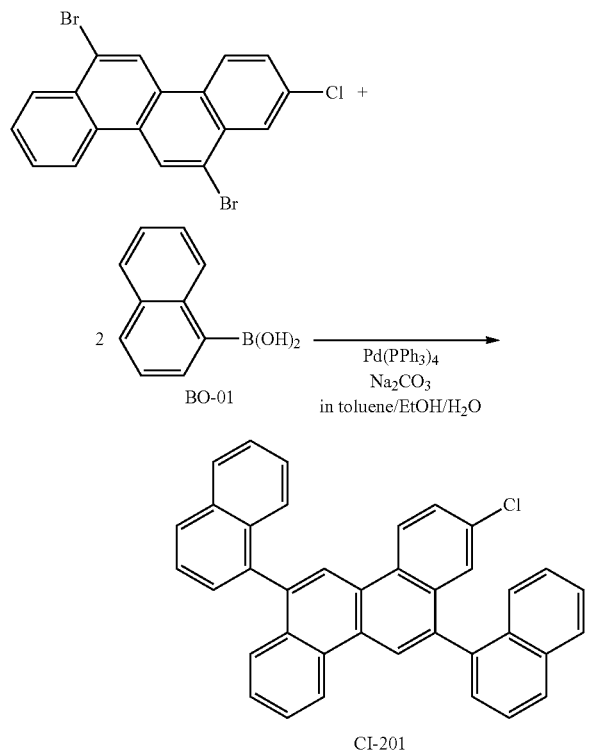

The following reagents and solvents were placed in a 300-mL recovery flask.

| | |
|---|---|
| 6,12-dibromo-2-chlorochrysene: | 0.82 g (1.95 mmol) |
| Boronic acid compound BO-01: | 0.74 g (4.31 mmol) |
| Tetrakis(triphenylphosphine)palladium(0): | 68 mg (59 μmmol) |
| Toluene: | 100 mL |
| Ethanol: | 50 mL |
| 10-wt % aqueous solution of sodium carbonate: | 50 mL |

The reaction solution was heated under reflux for 12 hours under nitrogen with stirring. After the completion of the reaction, the reaction solution was washed with water and dried over magnesium sulfate. Then, the dried product was concentrated. Thus, a crude product was obtained. Next, the crude product was subjected to dispersion washing under heat with a methanol solvent, and was then recrystallized with tolulene to purify the product. Thus, 0.70 g of Intermediate Cl-201 were obtained (in 70% yield).

(2) Synthesis of Exemplified Compound C703

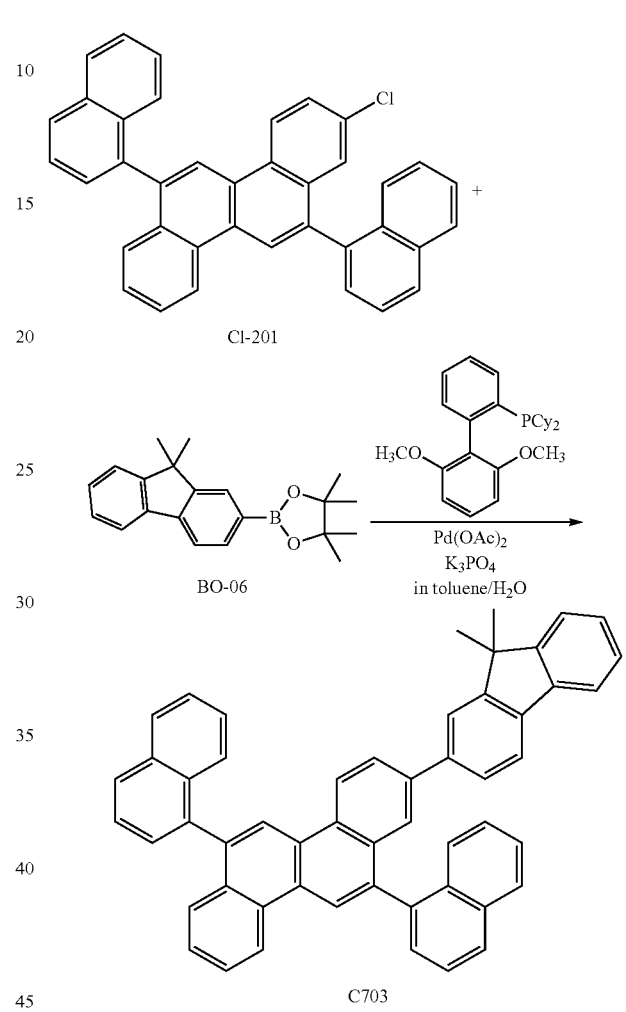

The following reagents and solvents were placed in a 100-mL recovery flask.

| | |
|---|---|
| Intermediate Cl-201: | 0.64 g (1.24 mmol) |
| Boronic Acid Compound BO-06: | 0.43 g (1.35 mmol) |
| Palladium(II) acetate: | 17 mg (80 μmol) |
| Dicyclohexyl(2',6'-dimethoxybiphenyl-2-yl)phosphine: | 71 mg (170 μmol) |
| Potassium phosphate: | 0.91 mg (4.29 mmol) |
| Toluene: | 40 mL |
| Water: | 10 mL |

The reaction solution was heated at 98° C. for 48 hours under nitrogen with stirring. After the completion of the reaction, the reaction solution was washed with water and dried over magnesium sulfate. Then, the dried product was concentrated. Thus, a crude product was obtained. Next, the crude product was subjected to dispersion washing under heat with a methanol solvent, followed by an ethanol solvent, and was then purified by silica gel column chromatography (eluent:

heptane/toluene=3/1). After that, the solution was further subjected to dispersion washing under heat with a methanol solvent. The resultant crystal was vacuum-dried at 150° C., and was then subjected to sublimation purification under conditions of $10^{-4}$ Pa and 370° C. Thus, 378 mg of Exemplified Compound C703 having a high purity were obtained (in 45% yield).

The results of the identification of the resultant compound are shown below.

(MALDI-TOF-MS)

Observed value: m/z=671.93, calculated value: $C_{53}H_{36}$=672.28

($^1$H-NMR (400 MHz, CDCl$_3$))

δ 9.00-8.75 (m, 4H), 8.15-7.99 (m, 4H), 7.94 (dd, 1H), 7.84 (d, 1H), 7.81-7.61 (m, 8H), 7.61-7.50 (m, 4H), 7.50-7.27 (m, 8H), 1.43 (s, 3.3H), 1.40 (s, 2.7H).

In addition, the energy gap of Exemplified Compound C703 was measured in the same manner as in Example 1-(4). As a result, the absorption edge of the light absorption spectrum was 385 nm, and Exemplified Compound C703 had an energy gap of 3.22 eV.

Further, DSC analysis was conducted on Exemplified Compound C703 in the same manner as in Example 1-(4). As a result, the compound was found to have a glass transition temperature of 189° C.

Example 10

Synthesis of Exemplified Compound C702

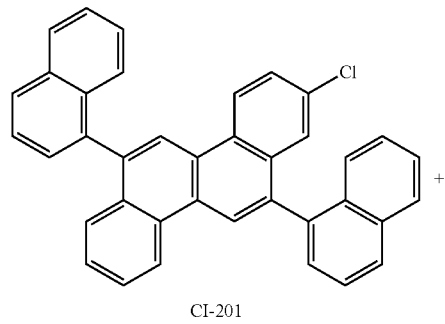

CI-201

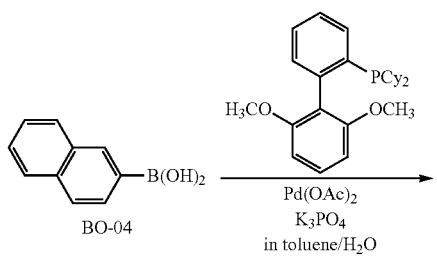

BO-04

→ Pd(OAc)$_2$, K$_3$PO$_4$ in toluene/H$_2$O

-continued

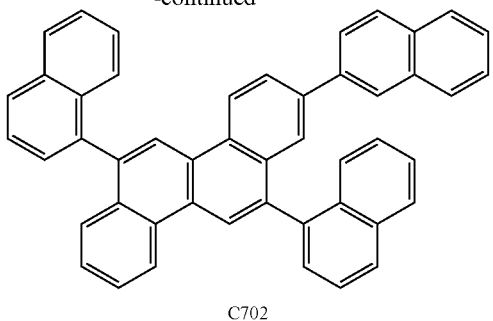

C702

The following reagents and solvents were placed in a 100-mL recovery flask.

| | |
|---|---|
| Intermediate Cl-201: | 0.74 g (1.93 mmol) |
| Boronic Acid Compound BO-04: | 0.33 g (1.35 mmol) |
| Palladium(II) acetate: | 49 mg (0.22 mmol) |
| Dicyclohexyl(2',6'-dimethoxybiphenyl-2-yl)phosphine: | 189 mg (0.46 mmol) |
| Potassium phosphate: | 1.64 g (7.74 mmol) |
| Toluene: | 20 mL |
| Water: | 1 mL |

The reaction solution was heated at 98° C. for 9.5 hours under nitrogen with stirring. After the completion of the reaction, the reaction solution was washed with water and dried over sodium sulfate. Then, the dried product was concentrated. Thus, a crude product was obtained. Next, the crude product was subjected to dispersion washing under heat with a methanol solvent, followed by a mixed solvent of acetone and methanol, and was then purified by silica gel column chromatography (eluent:heptane/toluene=7/3). After that, the solution was further subjected to dispersion washing under heat with a methanol solvent, followed by a mixed solvent of acetone and methanol. The resultant crystal was vacuum-dried at 150° C., and was then subjected to sublimation purification under conditions of $10^{-4}$ Pa and 375° C. Thus, 418 mg of Exemplified Compound C702 having a high purity were obtained (in 43% yield).

The results of the identification of the resultant compound are shown below.

(MALDI-TOF-MS)

Observed value: m/z=606.01, calculated value: $C_{48}H_{30}$=606.23

($^1$H-NMR (400 MHz, CDCl$_3$))

δ 8.91 (d, 1H), 8.88 (d, 2H), 8.83 (d, 1H), 8.20-7.95 (m, 5H), 7.91 (d, 1H), 7.88 (s, 1H), 7.85-7.49 (m, 14H), 7.49-7.39 (m, 3H), 7.39-7.29 (m, 2H).

In addition, the energy gap of Exemplified Compound C702 was measured in the same manner as in Example 1-(4). As a result, the absorption edge of the light absorption spectrum was 376 nm, and Exemplified Compound C702 had an energy gap of 3.30 eV.

Comparative Example 1

Comparison Between Energy Gaps

The energy gaps of Comparative Compounds H01 to H03 shown below were each measured in the same manner as in Example 1-(4). Table 3 shows the results together with the results of Examples 1 to 10.

(Comparative Compounds)

H01

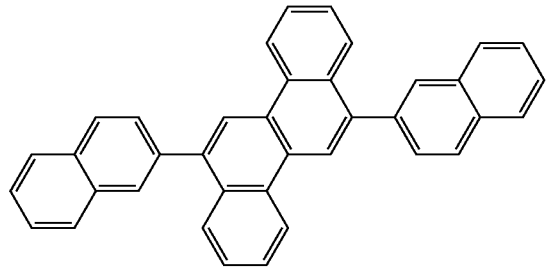

H02

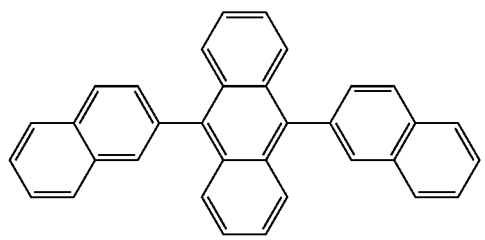

H03

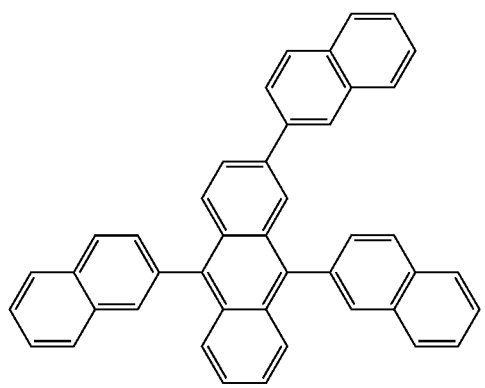

Comparative Example 2

Comparison Between Glass Transition Temperatures

The glass transition temperatures of Comparative Compounds H01 and H03 shown below were each measured in the same manner as in Example 1-(4). Table 3 shows the results together with the results of Examples 1 to 10.

TABLE 3

| | Absorption edge | Energy gap | Glass transition temperature |
|---|---|---|---|
| Exemplified Compound C101 | 403 nm | 3.08 eV | 144° C. |
| Exemplified Compound C103 | 405 nm | 3.06 eV | 189° C. |
| Exemplified Compound C107 | 403 nm | 3.08 eV | 161° C. |
| Exemplified Compound C110 | 412 nm | 3.01 eV | 181° C. |
| Exemplified Compound C201 | 408 nm | 3.04 eV | 144° C. |
| Exemplified Compound C202 | 412 nm | 3.01 eV | 191° C. |
| Exemplified Compound C501 | 404 nm | 3.07 eV | — |
| Exemplified Compound C505 | 397 nm | 3.12 eV | — |
| Exemplified Compound C702 | 376 nm | 3.30 eV | — |
| Exemplified Compound C703 | 385 nm | 3.22 eV | 189° C. |
| Comparative Compound H01 | 395 nm | 3.14 eV | 122° C. |
| Comparative Compound H02 | 426 nm | 2.91 eV | — |
| Comparative Compound H03 | 446 nm | 2.78 eV | 147° C. |

Compounds used in the production of organic light-emitting devices in the following examples and comparative examples are shown below.

HTL-1

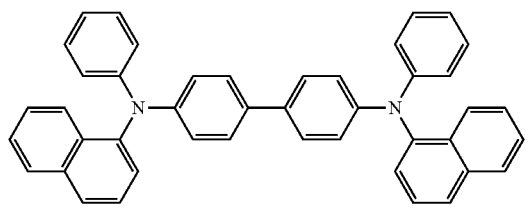

HTL-2

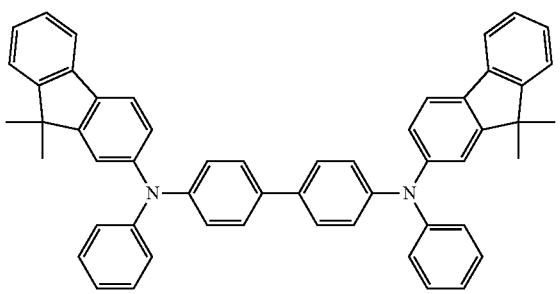

-continued
HTL-3
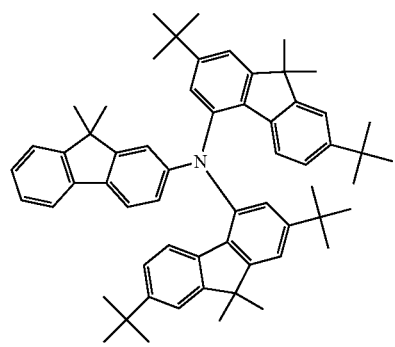
HTL-4
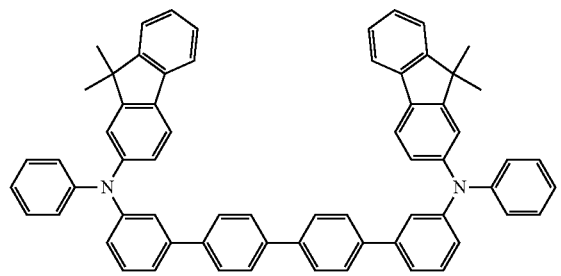
ETL-1
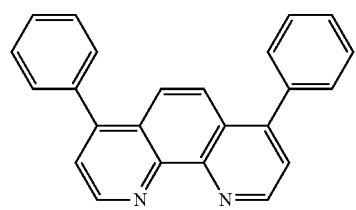
EIL-1
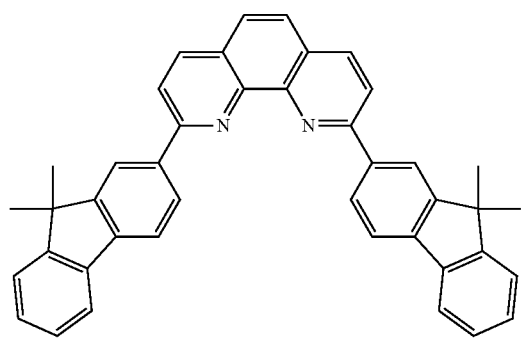
BD-3
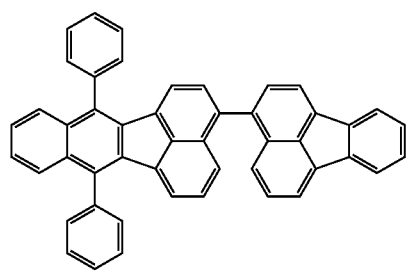
BD-7
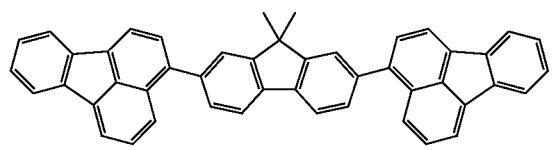
BH-1
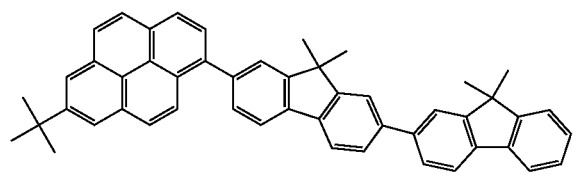
BH-2
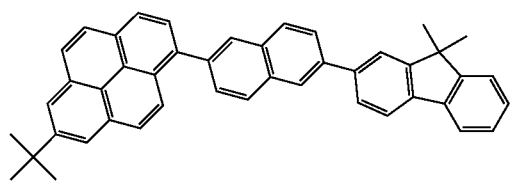
BH-3
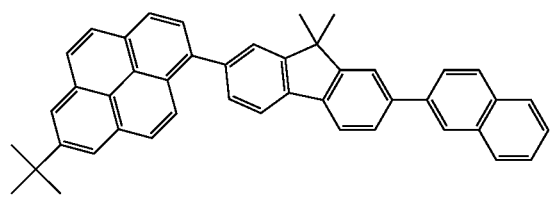
GD-1
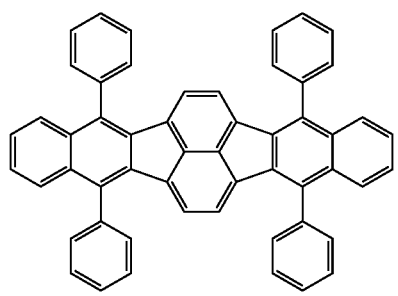

-continued
GH-1
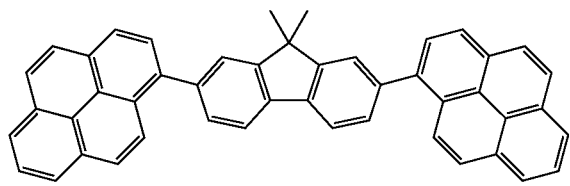
GA-1
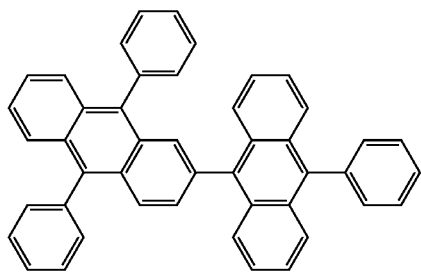
GA-2
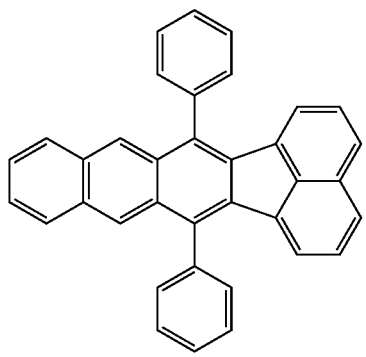
GA-3
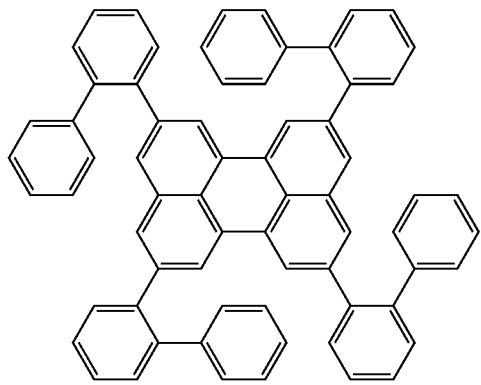
RD-1
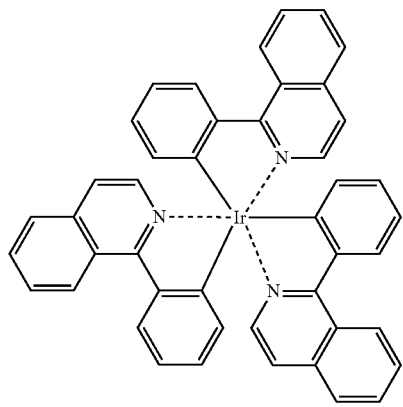
RA-1
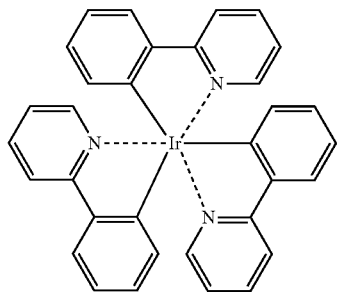
RA-2
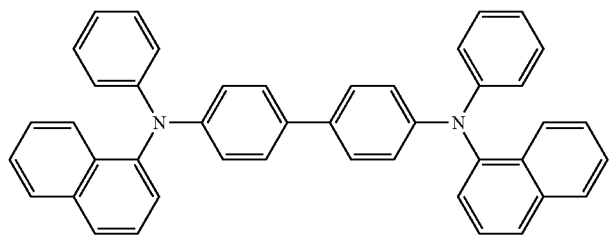
RH-1
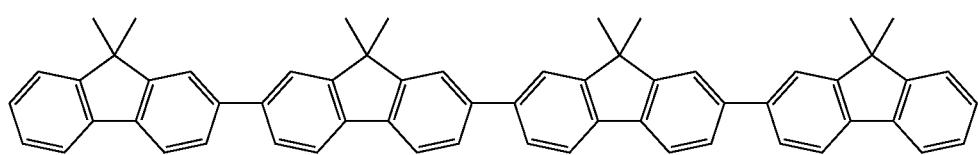

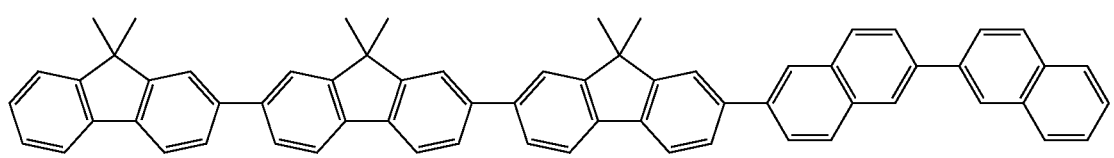

RH-2

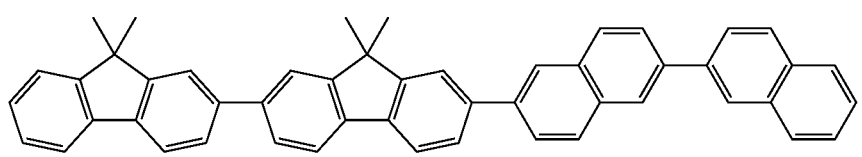

RH-3

Example 11

In this example, a device (including an anode, a hole transport layer, an emission layer, an electron transport layer, and a cathode) described in the third example of a multilayer organic light-emitting device was produced by the following method.

ITO was formed into a film having a thickness of 110 nm to serve as the anode on a glass substrate by a sputtering method, and the resultant was used as a transparent, conductive supporting substrate (ITO substrate). The following organic compound layers and electrode layers were continuously formed on the ITO substrate by vacuum evaporation based on resistance heating in a vacuum chamber having a pressure of $10^{-5}$ Pa. In this case, the device production was performed so that an opposing electrode area might be 3 $mm^2$.

| | |
|---|---|
| Hole transport layer (30 nm) | HTL-1 |
| Emission layer (30 nm) | Host: Exemplified Compound C101 |
| | Guest: BD-3 (5 wt %) |
| Electron transport layer (30 nm) | ETL-1 |
| Metal electrode layer 1 (0.5 nm) | LiF |
| Metal electrode layer 2 (100 nm) | Al |

Next, the resultant was covered with a protective glass plate and sealed with an acrylic resin-based adhesive in a dry air atmosphere in order that the organic light-emitting device might not deteriorate owing to moisture adsorption. Thus, the organic light-emitting device was obtained.

An applied voltage of 4.6 V was applied to the resultant organic light-emitting device while the ITO electrode was used as a positive electrode and the Al electrode was used as a negative electrode. As a result, the device was observed to emit blue light having a luminance of 1200 $cd/m^2$ with an emission efficiency of 7.3 cd/A. In addition, CIE chromaticity coordinates (x, y) in the device were (0.14, 0.21). Further, when the device was durably driven for 100 hours while a constant current density of 100 $mA/cm^2$ was kept, the ratio of reduction in luminance from the initial luminance was 25%.

Example 12

A device was produced by following the same procedure as in Example 11 with the exception that Exemplified Compound C103 was used instead of Exemplified Compound C101 as a host for the emission layer in Example 11. In addition, the resultant device was evaluated in the same manner as in Example 11. Table 4 shows the results.

Example 13

A device was produced by following the same procedure as in Example 11 with the exception that Exemplified Compound C107 was used instead of Exemplified Compound C101 as a host for the emission layer in Example 11. In addition, the resultant device was evaluated in the same manner as in Example 11. Table 4 shows the results.

Example 14

A device was produced by following the same procedure as in Example 11 with the exception that Exemplified Compound C110 was used instead of Exemplified Compound C101 as a host for the emission layer in Example 11. In addition, the resultant device was evaluated in the same manner as in Example 11. Table 4 shows the results.

Example 15

A device was produced by following the same procedure as in Example 11 with the exception that Exemplified Compound C201 was used instead of Exemplified Compound C101 as a host for the emission layer in Example 11. In addition, the resultant device was evaluated in the same manner as in Example 11. Table 4 shows the results.

Example 16

A device was produced by following the same procedure as in Example 11 with the exception that Exemplified Compound C202 was used instead of Exemplified Compound C101 as a host for the emission layer in Example 11. In addition, the resultant device was evaluated in the same manner as in Example 11. Table 4 shows the results.

Comparative Example 3

A device was produced by following the same procedure as in Example 11 with the exception that Comparative Compound H01 was used instead of Exemplified Compound C101 as a host for the emission layer in Example 11. In addition, the resultant device was evaluated in the same manner as in Example 11. Table 4 shows the results.

Comparative Example 4

A device was produced by following the same procedure as in Example 11 with the exception that Comparative Compound H02 was used instead of Exemplified Compound C101 as a host for the emission layer in Example 11. In addition, the resultant device was evaluated in the same manner as in Example 11. Table 4 shows the results.

emit blue light having a luminance of 1300 cd/m² with an emission efficiency of 5.0 cd/A. In addition, CIE chromaticity

TABLE 4

|  | Host | CIE chromaticity | Applied voltage @1200 cd/m² (V) | Emission efficiency @1200 cd/m² (cd/A) | Ratio of reduction in luminance after 100 hours @100 mA/cm² |
| --- | --- | --- | --- | --- | --- |
| Example 11 | Exemplified Compound C101 | (0.14, 0.21) | 4.6 | 7.3 | 25% |
| Example 12 | Exemplified Compound C103 | (0.16, 0.23) | 4.6 | 6.1 | 29% |
| Example 13 | Exemplified Compound C107 | (0.15, 0.24) | 4.4 | 5.9 | 33% |
| Example 14 | Exemplified Compound C110 | (0.16, 0.26) | 4.2 | 6.7 | 20% |
| Example 15 | Exemplified Compound C201 | (0.14, 0.22) | 4.4 | 7.4 | 21% |
| Example 16 | Exemplified Compound C202 | (0.16, 0.25) | 4.2 | 7.1 | 35% |
| Comparative Example 3 | Comparative Compound H01 | (0.14, 0.20) | 6.6 | 4.5 | 58% |
| Comparative Example 4 | Comparative Compound H02 | (0.14, 0.24) | 3.8 | 3.9 | 37% |

Example 17

In this example, a device (including an anode, a hole transport layer, an emission layer, an electron transport layer, and a cathode) described in the third example of a multilayer organic light-emitting device, in which the electron transport layer was formed of two layers having different ionization potentials, was produced by the following method.

The following organic compound layers and electrode layers were continuously formed on an ITO substrate produced by following the same procedure as in Example 8 by vacuum evaporation based on resistance heating in a vacuum chamber having a pressure of $10^{-5}$ Pa. In this case, the device production was performed so that an opposing electrode area might be 3 mm².

| | |
| --- | --- |
| Hole transport layer (25 nm) | HTL-2 |
| Emission layer (35 nm) | Host: BH-1 |
| | Guest: BD-7 (5 wt %) |
| Electron transport layer 1 (10 nm) | Exemplified Compound C101 |
| Electron transport layer 2 (25 nm) | ETL-1 |
| Metal electrode layer 1 (0.5 nm) | LiF |
| Metal electrode layer 2 (100 nm) | Al |

Next, the resultant was covered with a protective glass plate and sealed with an acrylic resin-based adhesive in a dry air atmosphere in order that the organic light-emitting device might not deteriorate owing to moisture adsorption. Thus, the organic light-emitting device was obtained.

An applied voltage of 4.2 V was applied to the resultant organic light-emitting device while the ITO electrode was used as a positive electrode and the Al electrode was used as a negative electrode. As a result, the device was observed to emit blue light having a luminance of 1300 cd/m² with an emission efficiency of 5.0 cd/A. In addition, CIE chromaticity coordinates (x, y) in the device were (0.15, 0.21). Further, when the device was durably driven for 250 hours while a constant current density of 50 mA/cm² was kept, the ratio of reduction in luminance from the initial luminance was 9%.

Example 18

A device was produced by following the same procedure as in Example 17 with the exception that Exemplified Compound C103 was used instead of Exemplified Compound C101 as an electron transport layer 1 in Example 17. In addition, the resultant device was evaluated in the same manner as in Example 17. Table 5 shows the results.

Example 19

A device was produced by following the same procedure as in Example 17 with the exception that Exemplified Compound C107 was used instead of Exemplified Compound C101 as an electron transport layer 1 in Example 17. In addition, the resultant device was evaluated in the same manner as in Example 17. Table 5 shows the results.

Example 20

A device was produced by following the same procedure as in Example 17 with the exception that Exemplified Compound C110 was used instead of Exemplified Compound C101 as an electron transport layer 1 in Example 17. In addition, the resultant device was evaluated in the same manner as in Example 17. Table 5 shows the results.

Example 21

A device was produced by following the same procedure as in Example 17 with the exception that Exemplified Compound C201 was used instead of Exemplified Compound C101 as an electron transport layer 1 in Example 17. In addition, the resultant device was evaluated in the same manner as in Example 17. Table 5 shows the results.

Example 22

A device was produced by following the same procedure as in Example 17 with the exception that Exemplified Compound C202 was used instead of Exemplified Compound C101 as an electron transport layer 1 in Example 17. In addition, the resultant device was evaluated in the same manner as in Example 17. Table 5 shows the results.

Example 23

A device was produced by following the same procedure as in Example 17 with the exception that Exemplified Compound C501 was used instead of Exemplified Compound C101 as an electron transport layer 1 in Example 17. In addition, the resultant device was evaluated in the same manner as in Example 17. Table 5 shows the results.

Example 24

A device was produced by following the same procedure as in Example 17 with the exception that Exemplified Compound C505 was used instead of Exemplified Compound C101 as an electron transport layer 1 in Example 17. In addition, the resultant device was evaluated in the same manner as in Example 17. Table 5 shows the results.

Example 25

A device was produced by following the same procedure as in Example 17 with the exception that Exemplified Compound C702 was used instead of Exemplified Compound C101 as an electron transport layer 1 in Example 17. In addition, the resultant device was evaluated in the same manner as in Example 17. Table 5 shows the results.

Example 26

A device was produced by following the same procedure as in Example 17 with the exception that Exemplified Compound C703 was used instead of Exemplified Compound C101 as an electron transport layer 1 in Example 17. In addition, the resultant device was evaluated in the same manner as in Example 17. Table 5 shows the results.

Comparative Example 5

A device was produced by following the same procedure as in Example 17 with the exception that Comparative Compound H01 was used instead of Exemplified Compound C101 as an electron transport layer 1 in Example 17. In addition, the resultant device was evaluated in the same manner as in Example 17. Table 5 shows the results.

Comparative Example 6

A device was produced by following the same procedure as in Example 17 with the exception that Comparative Compound H02 was used instead of Exemplified Compound C101 as an electron transport layer 1 in Example 17. In addition, the resultant device was evaluated in the same manner as in Example 17. Table 5 shows the results.

TABLE 5

|  | Electron transport layer 1 | CIE chromaticity | Applied voltage @1300 cd/m$^2$ (V) | Emission efficiency @1300 cd/m$^2$ (cd/A) | Ratio of reduction in luminance after 250 hours @50 mA/cm$^2$ |
|---|---|---|---|---|---|
| Example 17 | Exemplified Compound C101 | (0.15, 0.21) | 4.2 | 5.0 | 9% |
| Example 18 | Exemplified Compound C103 | (0.15, 0.23) | 4.6 | 4.7 | 13% |
| Example 19 | Exemplified Compound C107 | (0.15, 0.21) | 4.1 | 5.5 | 7% |
| Example 20 | Exemplified Compound C110 | (0.15, 0.22) | 4.2 | 5.5 | 8% |
| Example 21 | Exemplified Compound C201 | (0.15, 0.21) | 4.0 | 4.8 | 11% |
| Example 22 | Exemplified Compound C202 | (0.16, 0.24) | 4.5 | 4.6 | 15% |
| Example 23 | Exemplified Compound C501 | (0.15, 0.21) | 4.1 | 5.0 | 13% |
| Example 24 | Exemplified Compound C505 | (0.15, 0.23) | 4.2 | 4.8 | 16% |
| Example 25 | Exemplified Compound C702 | (0.15, 0.20) | 4.5 | 5.5 | 10% |
| Example 26 | Exemplified Compound C703 | (0.15, 0.21) | 4.4 | 5.6 | 9% |

TABLE 5-continued

|  | Electron transport layer 1 | CIE chromaticity | Applied voltage @1300 cd/m² (V) | Emission efficiency @1300 cd/m² (cd/A) | Ratio of reduction in luminance after 250 hours @50 mA/cm² |
|---|---|---|---|---|---|
| Comparative Example 5 | Comparative Compound H01 | (0.15, 0.21) | 5.3 | 3.2 | 51% |
| Comparative Example 6 | Comparative Compound H02 | (0.15, 0.28) | 3.9 | 4.3 | 16% |

Example 27

In this example, a device (including an anode, a hole injection layer, a hole transport layer, an emission layer, an electron transport layer, an electron injection layer, and a cathode) described in the fifth example of a multilayer organic light-emitting device, in which an organic light-emitting device has a resonance structure, was produced by the following method.

An aluminum alloy (AlNd) was formed into a film having a thickness of 100 nm to serve as a reflective anode by a sputtering method on a glass substrate as a support member. Further, ITO was formed into a film having a thickness of 40 nm to serve as a transparent anode by a sputtering method. Next, an acrylic device separation film having a thickness of 1.5 μm was formed at the peripheral portions of the anodes, and was provided with openings each having a radius of 3 mm. The resultant was subjected to ultrasonic cleaning with acetone and isopropyl alcohol (IPA) sequentially. After that, the resultant was washed with boiled IPA and dried. Further, the surface of the substrate was cleaned with UV/ozone.

Further, the following organic layers were successively formed by vacuum evaporation based on resistive heating in a vacuum chamber having a pressure of $10^{-5}$ Pa.

| Hole injection layer (90 nm) | HTL-1 |
| Hole transport layer (10 nm) | HTL-3 |
| Emission layer (35 mm) | Host: BH-2 |
| | Guest: BD-3 (2 wt %) |
| Electron transport layer (10 nm) | Exemplified Compound C101 |
| Electron injection layer (70 nm) | EIL-1 (78 wt %), Li (22 wt %) |

Subsequently, IZO was formed into a film to serve as a cathode by a sputtering method. Thus, a transparent electrode having a thickness of 30 nm was formed. After that, the resultant was sealed in a nitrogen atmosphere. Thus, the organic light-emitting device was obtained.

An applied voltage of 4.8 V was applied to the resultant organic light-emitting device while the ITO electrode was used as a positive electrode and the IZO electrode was used as a negative electrode. As a result, the device was observed to emit blue light having a luminance of 1000 cd/m² with an emission efficiency of 4.2 cd/A. In addition, CIE chromaticity coordinates (x, y) in the device were (0.13, 0.09). Further, when the device was durably driven for 100 hours while a constant current density of 100 mA/cm² was kept, the ratio of reduction in luminance from the initial luminance was 3.0%.

Example 28

A device was produced by following the same procedure as in Example 27 with the exception that Exemplified Compound C103 was used instead of Exemplified Compound C101 in the electron transport layer in Example 27. In addition, the resultant device was evaluated in the same manner as in Example 27. Table 6 shows the results.

Example 29

A device was produced by following the same procedure as in Example 27 with the exception that BH-1 was used instead of BH-2 as a host for the emission layer and Exemplified Compound C107 was used instead of Exemplified Compound C101 in the electron transport layer in Example 27. In addition, the resultant device was evaluated in the same manner as in Example 27. Table 6 shows the results.

Example 30

A device was produced by following the same procedure as in Example 27 with the exception that BH-1 was used instead of BH-2 as a host for the emission layer and Exemplified Compound C110 was used instead of Exemplified Compound C101 in the electron transport layer in Example 27. In addition, the resultant device was evaluated in the same manner as in Example 27. Table 6 shows the results.

Example 31

A device was produced by following the same procedure as in Example 27 with the exception that BH-1 was used instead of BH-2 as a host for the emission layer and Exemplified Compound C201 was used instead of Exemplified Compound C101 in the electron transport layer in Example 27. In addition, the resultant device was evaluated in the same manner as in Example 27. Table 6 shows the results.

Example 32

A device was produced by following the same procedure as in Example 27 with the exception that Exemplified Compound C703 was used instead of Exemplified Compound C101 as an electron transport layer in Example 27. In addition, the resultant device was evaluated in the same manner as in Example 27. Table 6 shows the results.

Comparative Example 7

A device was produced by following the same procedure as in Example 27 with the exception that Comparative Compound H01 was used instead of Exemplified Compound C101 as an electron transport layer in Example 27. In addition, the resultant device was evaluated in the same manner as in Example 27. Table 6 shows the results.

TABLE 6

| | Host for emission layer | Electron transport layer | CIE chromaticity | Applied voltage @1000 cd/m² (V) | Emission efficiency @1000 cd/m² (cd/A) | Ratio of reduction in luminance after 100 hours @100 mA/cm² |
|---|---|---|---|---|---|---|
| Example 27 | BH-2 | Exemplified Compound C101 | (0.13, 0.09) | 4.8 | 4.2 | 3.0% |
| Example 28 | BH-2 | Exemplified Compound C103 | (0.13, 0.09) | 5.2 | 3.9 | 6.5% |
| Example 29 | BH-1 | Exemplified Compound C107 | (0.13, 0.09) | 4.8 | 4.2 | 2.8% |
| Example 30 | BH-1 | Exemplified Compound C110 | (0.13, 0.09) | 4.9 | 4.2 | 5.5% |
| Example 31 | BH-1 | Exemplified Compound C201 | (0.13, 0.10) | 4.7 | 4.5 | 9.6% |
| Example 32 | BH-2 | Exemplified Compound C703 | (0.13, 0.09) | 5.0 | 4.1 | 3.4% |
| Comparative Example 7 | BH-2 | Comparative Compound H01 | (0.13, 0.10) | 5.3 | 3.7 | 21% |

Example 33

In this example, a multilayer organic light-emitting device (anode/hole injection layer/hole transport layer/emission layer/electron transport layer/electron injection layer/cathode) having the same resonance structure as that of Example 27 in which a transparent metal thin film layer for resonance was interposed between the electron injection layer and the cathode was produced by the following method.

The following organic layers and electrode layer were continuously formed on an ITO substrate obtained in the same manner as in Example 27 by vacuum evaporation based on resistive heating in a vacuum chamber having a pressure of $10^{-5}$ Pa.

| | |
|---|---|
| Hole injection layer (95 nm) | HTL-2 |
| Hole transport layer (10 nm) | HTL-4 |
| Emission layer (25 nm) | Host: BH-1 |
| | Guest: BD-3 (2 wt %) |
| Electron transport layer (10 nm) | Exemplified Compound C101 |
| Electron injection layer (40 nm) | EIL-1 (70 wt %), Cs (30 wt %) |
| Transparent metal thin film layer (12 nm) | Ag |

Subsequently, IZO was formed into a film to serve as a cathode by a sputtering method. Thus, a transparent electrode having a thickness of 50 nm was formed. After that, the resultant was sealed in a nitrogen atmosphere. Thus, the organic light-emitting device was obtained.

An applied voltage of 4.5 V was applied to the resultant organic light-emitting device while the ITO electrode was used as a positive electrode and the IZO electrode was used as a negative electrode. As a result, the device was observed to emit blue light having a luminance of 2000 cd/m² with an emission efficiency of 4.0 cd/A. In addition, CIE chromaticity coordinates (x, y) in the device were (0.13, 0.11). Further, when the device was durably driven for 60 hours while a constant current density of 100 mA/cm² was kept, the ratio of reduction in luminance from the initial luminance was 19%.

Example 34

A device was produced by following the same procedure as in Example 33 with the exception that BH-2 was used instead of BH-1 as a host for the emission layer and Exemplified Compound C107 was used instead of Exemplified Compound C101 in the electron transport layer in Example 33. In addition, the resultant device was evaluated in the same manner as in Example 33. Table 7 shows the results.

Example 35

A device was produced by following the same procedure as in Example 33 with the exception that BH-2 was used instead of BH-1 as a host for the emission layer and Exemplified Compound C501 was used instead of Exemplified Compound C101 in the electron transport layer in Example 33. In addition, the resultant device was evaluated in the same manner as in Example 33. Table 7 shows the results.

Example 36

A device was produced by following the same procedure as in Example 33 with the exception that BH-3 was used instead of BH-1 as a host for the emission layer and Exemplified Compound C505 was used instead of Exemplified Compound C101 in the electron transport layer in Example 33. In addition, the resultant device was evaluated in the same manner as in Example 33. Table 7 shows the results.

Example 37

A device was produced by following the same procedure as in Example 33 with the exception that BH-3 was used instead of BH-1 as a host for the emission layer and Exemplified Compound C702 was used instead of Exemplified Compound C101 in the electron transport layer in Example 33. In addition, the resultant device was evaluated in the same manner as in Example 33. Table 7 shows the results.

Example 38

A device was produced by following the same procedure as in Example 33 with the exception that Exemplified Compound C703 was used instead of Exemplified Compound C101 in the electron transport layer in Example 33. In addition, the resultant device was evaluated in the same manner as in Example 33. Table 7 shows the results.

Comparative Example 8

A device was produced by following the same procedure as in Example 33 with the exception that Comparative Compound H01 was used instead of Exemplified Compound C101 in the electron transport layer in Example 33. In addition, the resultant device was evaluated in the same manner as in Example 33. Table 7 shows the results.

Subsequently, IZO was formed into a film to serve as a cathode by a sputtering method. Thus, a transparent electrode having a thickness of 30 nm was formed. After that, the resultant was sealed in a nitrogen atmosphere. Thus, the organic light-emitting device was obtained.

An applied voltage of 4.5 V was applied to the resultant organic light-emitting device while the ITO electrode was used as a positive electrode and the IZO electrode was used as a negative electrode. As a result, the device was observed to emit green light having a luminance of 3600 cd/m$^2$ with an emission efficiency of 17.0 cd/A. In addition, CIE chromaticity coordinates (x, y) in the device were (0.21, 0.71). Further, when the device was durably driven for 500 hours while a constant current density of 100 mA/cm$^2$ was kept, the ratio of reduction in luminance from the initial luminance was 10.4%.

TABLE 7

| | Host for emission layer | Electron transport layer | CIE chromaticity | Applied voltage @2000 cd/m$^2$ (V) | Emission efficiency @2000 cd/m$^2$ (cd/A) | Ratio of reduction in luminance after 60 hours @100 mA/cm$^2$ |
|---|---|---|---|---|---|---|
| Example 33 | BH-1 | Exemplified Compound C101 | (0.13, 0.11) | 4.5 | 4.0 | 19% |
| Example 34 | BH-2 | Exemplified Compound C107 | (0.12, 0.12) | 4.6 | 4.2 | 23% |
| Example 35 | BH-2 | Exemplified Compound C501 | (0.13, 0.10) | 4.7 | 3.6 | 25% |
| Example 36 | BH-3 | Exemplified Compound C505 | (0.12, 0.11) | 5.2 | 3.8 | 32% |
| Example 37 | BH-3 | Exemplified Compound C702 | (0.12, 0.11) | 4.8 | 4.0 | 11% |
| Example 38 | BH-1 | Exemplified Compound C703 | (0.13, 0.10) | 4.8 | 4.1 | 11% |
| Comparative Example 8 | BH-1 | Comparative Compound H01 | (0.13, 0.11) | 5.3 | 3.4 | 55% |

Example 39

In this example, a multilayer organic light-emitting device (anode/hole transport layer/emission layer/electron transport layer/electron injection layer/cathode) having the same resonance structure as that of Example 27 in which the emission layer had an assist material in addition to a host material and a guest material was produced by the following method.

The following organic layers and electrode layer were continuously formed on an ITO substrate obtained in the same manner as in Example 27 by vacuum evaporation based on resistive heating in a vacuum chamber having a pressure of 10$^{-5}$ Pa.

| | |
|---|---|
| Hole transport layer (140 nm) | HTL-1 |
| Emission layer (20 nm) | Host: GH-1 |
| | Assist: GA-1 (30 wt %) |
| | Guest: BD-3 (2 wt %) |
| Electron transport layer (10 nm) | Exemplified Compound C101 |
| Electron injection layer (70 nm) | EIL-1 (70 wt %), Cs (30 wt %) |

Example 40

A device was produced by following the same procedure as in Example 39 with the exception that GA-2 was used instead of GA-1 as an assist for the emission layer and Exemplified Compound C107 was used instead of Exemplified Compound C101 in the electron transport layer in Example 39. In addition, the resultant device was evaluated in the same manner as in Example 39. Table 8 shows the results.

Example 41

A device was produced by following the same procedure as in Example 39 with the exception that GA-3 was used instead of GA-1 as an assist for the emission layer and Exemplified Compound C110 was used instead of Exemplified Compound C101 in the electron transport layer in Example 33. In addition, the resultant device was evaluated in the same manner as in Example 39. Table 8 shows the results.

Example 42

A device was produced by following the same procedure as in Example 39 with the exception that GA-3 was used instead of GA-1 as an assist for the emission layer and Exemplified Compound C501 was used instead of Exemplified Compound C101 in the electron transport layer in Example 39. In addition, the resultant device was evaluated in the same manner as in Example 39. Table 8 shows the results.

Example 43

A device was produced by following the same procedure as in Example 39 with the exception that GA-2 was used instead of GA-1 as an assist for the emission layer and Exemplified Compound C702 was used instead of Exemplified Compound C101 in the electron transport layer in Example 39. In addition, the resultant device was evaluated in the same manner as in Example 39. Table 8 shows the results.

Example 44

A device was produced by following the same procedure as in Example 39 with the exception that Exemplified Compound C703 was used instead of Exemplified Compound C101 in the electron transport layer in Example 39. In addition, the resultant device was evaluated in the same manner as in Example 39. Table 8 shows the results.

Comparative Example 9

A device was produced by following the same procedure as in Example 39 with the exception that Comparative Compound H01 was used instead of Exemplified Compound C101 in the electron transport layer in Example 39. In addition, the resultant device was evaluated in the same manner as in Example 39. Table 8 shows the results.

Comparative Example 10

A device was produced by following the same procedure as in Example 39 with the exception that GA-2 was used instead of GA-1 as an assist for the emission layer and Comparative Compound H02 was used instead of Exemplified Compound C101 in the electron transport layer in Example 39. In addition, the resultant device was evaluated in the same manner as in Example 39. Table 8 shows the results.

TABLE 8

| | Assist for emission layer | Electron transport layer | CIE chromaticity | Applied voltage @3600 cd/m$^2$ (V) | Emission efficiency @3600 cd/m$^2$ (cd/A) | Ratio of reduction in luminance after 500 hours @100 mA/cm$^2$ |
|---|---|---|---|---|---|---|
| Example 39 | GA-1 | Exemplified Compound C101 | (0.21, 0.71) | 4.5 | 17.0 | 10.4% |
| Example 40 | GA-2 | Exemplified Compound C107 | (0.22, 0.72) | 4.2 | 19.5 | 8.8% |
| Example 41 | GA-3 | Exemplified Compound C110 | (0.21, 0.72) | 4.1 | 16.6 | 14.1% |
| Example 42 | GA-3 | Exemplified Compound C501 | (0.22, 0.70) | 4.3 | 18.6 | 12.9% |
| Example 43 | GA-2 | Exemplified Compound C702 | (0.23, 0.69) | 4.8 | 20.5 | 9.5% |
| Example 44 | GA-1 | Exemplified Compound C703 | (0.23, 0.69) | 4.9 | 20.8 | 9.1% |
| Comparative Example 9 | GA-1 | Comparative Compound H01 | (0.22, 0.70) | 5.5 | 11.3 | 41.8% |
| Comparative Example 10 | GA-2 | Comparative Compound H02 | (0.21, 0.71) | 5.0 | 9.7 | 30.2% |

Example 45

In this example, a multilayer organic light-emitting device (anode/hole injection layer/hole transport layer/emission layer/electron transport layer/electron injection layer/cathode) having the same resonance structure as that of Example 27 in which the emission layer had an assist material in addition to a host material and a guest material and in which a transparent metal thin film layer for resonance was interposed between the electron injection layer and the cathode was produced by the following method.

The following organic layers and electrode layer were continuously formed on an ITO substrate obtained in the same manner as in Example 27 by vacuum evaporation based on resistive heating in a vacuum chamber having a pressure of 10$^{-5}$ Pa.

| | |
|---|---|
| Hole injection layer (195 nm) | HTL-2 |
| Hole transport layer (10 nm) | HTL-1 |
| Emission layer (20 nm) | Host: RH-1 |
| | Assist: RA-1 (16 wt %) |
| | Guest: RD-1 (2 wt %) |
| Electron transport layer (10 nm) | Exemplified Compound C101 |
| Electron injection layer (30 nm) | EIL-1 (70 wt %), Cs (30 wt %) |

Subsequently, IZO was formed into a film to serve as a cathode by a sputtering method. Thus, a transparent electrode having a thickness of 30 nm was formed. After that, the resultant was sealed in a nitrogen atmosphere. Thus, the organic light-emitting device was obtained.

An applied voltage of 4.6 V was applied to the resultant organic light-emitting device while the ITO electrode was used as a positive electrode and the IZO electrode was used as a negative electrode. As a result, the device was observed to emit red light having a luminance of 3000 cd/m$^2$ with an emission efficiency of 9.1 cd/A. In addition, CIE chromaticity coordinates (x, y) in the device were (0.67, 0.32). Further, when the device was durably driven for 100 hours while a constant current density of 100 mA/cm$^2$ was kept, the ratio of reduction in luminance from the initial luminance was 20%.

Example 46

A device was produced by following the same procedure as in Example 45 with the exception that RH-2 was used instead of RH-1 as a host for the emission layer and Exemplified Compound C103 was used instead of Exemplified Compound C101 in the electron transport layer in Example 45. In addition, the resultant device was evaluated in the same manner as in Example 45. Table 9 shows the results.

Example 47

A device was produced by following the same procedure as in Example 45 with the exception that RH-3 was used instead of RH-1 as a host for the emission layer and Exemplified Compound C107 was used instead of Exemplified Compound C101 in the electron transport layer in Example 45. In addition, the resultant device was evaluated in the same manner as in Example 45. Table 9 shows the results.

Example 48

A device was produced by following the same procedure as in Example 45 with the exception that RA-2 was used instead of RA-1 as an assist for the emission layer and Exemplified Compound C201 was used instead of Exemplified Compound C101 in the electron transport layer in Example 45. In addition, the resultant device was evaluated in the same manner as in Example 45. Table 9 shows the results.

Example 49

A device was produced by following the same procedure as in Example 45 with the exception that RH-2 was used instead of RH-1 as a host for the emission layer, RA-2 was used instead of RA-1 as an assist for the emission layer, and Exemplified Compound C702 was used instead of Exemplified Compound C101 in the electron transport layer in Example 45. In addition, the resultant device was evaluated in the same manner as in Example 45. Table 9 shows the results.

Example 50

A device was produced by following the same procedure as in Example 45 with the exception that RH-3 was used instead of RH-1 as a host for the emission layer, RA-2 was used instead of RA-1 as an assist for the emission layer, and Exemplified Compound C703 was used instead of Exemplified Compound C101 in the electron transport layer in Example 45. In addition, the resultant device was evaluated in the same manner as in Example 45. Table 9 shows the results.

Comparative Example 11

A device was produced by following the same procedure as in Example 45 with the exception that Comparative Compound H01 was used instead of Exemplified Compound C101 in the electron transport layer in Example 45. In addition, the resultant device was evaluated in the same manner as in Example 45. Table 9 shows the results.

Comparative Example 12

A device was produced by following the same procedure as in Example 45 with the exception that RH-2 was used instead of RH-1 as a host for the emission layer, RA-2 was used instead of RA-1 as an assist for the emission layer, and Comparative Compound H02 was used instead of Exemplified Compound C101 in the electron transport layer in Example 45. In addition, the resultant device was evaluated in the same manner as in Example 45. Table 9 shows the results.

TABLE 9

| | Host for emission layer | Assist for emission layer | Electron transport layer | CIE chromaticity | Applied voltage @3000 cd/m$^2$ (V) | Emission efficiency @3000 cd/m$^2$ (cd/A) | Ratio of reduction in luminance after 100 hours @100 mA/cm$^2$ |
|---|---|---|---|---|---|---|---|
| Example 45 | RH-1 | RA-1 | Exemplified Compound C101 | (0.67, 0.32) | 4.6 | 9.1 | 20% |
| Example 46 | RH-2 | RA-1 | Exemplified Compound C103 | (0.68, 0.32) | 4.7 | 11.8 | 31% |
| Example 47 | RH-3 | RA-1 | Exemplified Compound C107 | (0.68, 0.32) | 4.7 | 14.2 | 15% |
| Example 48 | RH-1 | RA-2 | Exemplified Compound C201 | (0.67, 0.32) | 4.5 | 8.7 | 33% |

TABLE 9-continued

| | Host for emission layer | Assist for emission layer | Electron transport layer | CIE chromaticity | Applied voltage @3000 cd/m² (V) | Emission efficiency @3000 cd/m² (cd/A) | Ratio of reduction in luminance after 100 hours @100 mA/cm² |
|---|---|---|---|---|---|---|---|
| Example 49 | RH-2 | RA-2 | Exemplified Compound C702 | (0.67, 0.33) | 5.3 | 9.9 | 19% |
| Example 50 | RH-3 | RA-2 | Exemplified Compound C703 | (0.66, 0.33) | 5.1 | 10.1 | 18% |
| Comparative Example 11 | RH-1 | RA-1 | Comparative Compound H01 | (0.67, 0.33) | 5.7 | 6.6 | 45% |
| Comparative Example 12 | RH-2 | RA-2 | Comparative Compound H02 | (0.67, 0.32) | 4.6 | 6.5 | 48% |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2009-063012, filed Mar. 16, 2009, No. 2009-236435, filed Oct. 13, 2009, and No. 2010-010192, filed Jan. 20, 2010 which are hereby incorporated by reference herein in there entirety.

The invention claimed is:

1. A chrysene compound represented by the general formula [1]:

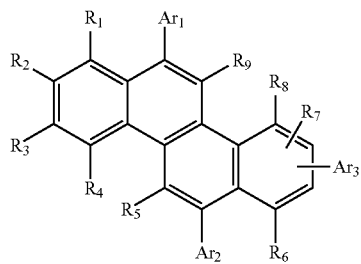

[1]

wherein $R_1$ to $R_9$ are each independently selected from the group consisting of a hydrogen atom, a substituted or unsubstituted alkyl group, and a substituted or unsubstituted alkoxy group; and $Ar_1$, $Ar_2$, and $Ar_3$ are each independently selected from the group represented by the general formulae [2]:

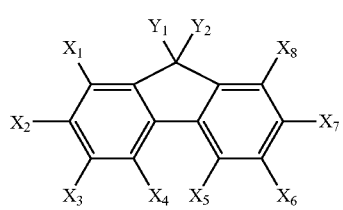

[2]

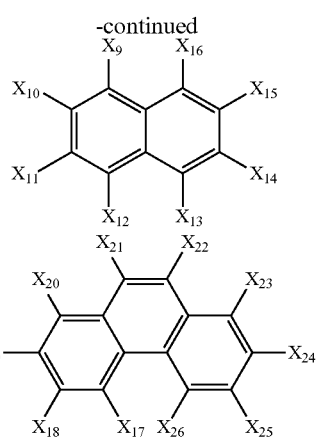

wherein $X_1$ to $X_{26}$ are each independently selected from the group consisting of a hydrogen atom, a substituted or unsubstituted alkyl group, a substituted or unsubstituted alkoxy group, a substituted or unsubstituted phenyl group, a substituted or unsubstituted naphthyl group, a substituted or unsubstituted phenanthryl group, and a substituted or unsubstituted fluorenyl group, provided that one of $X_1$ to $X_8$, one of $X_9$ to $X_{16}$, and one of $X_{17}$ to $X_{26}$ each represent a chrysene ring represented by the general formula [1]; and $Y_1$ and $Y_2$ are each independently selected from a hydrogen atom and a substituted or unsubstituted alkyl group.

2. The chrysene compound according to claim 1, which is a compound represented by the general formula [3]:

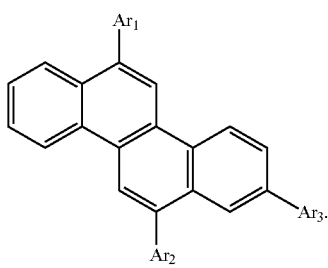

[3]

3. The chrysene compound according to claim 1, which is a compound represented by the general formula [4]:

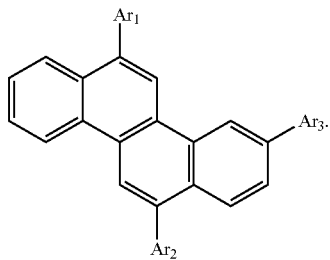

[4]

4. An organic light-emitting device, comprising:
a pair of electrodes; and
an organic compound layer interposed between the pair of electrodes,
wherein the organic compound layer comprises the chrysene compound according to claim 1.

5. The organic light-emitting device according to claim 4, wherein the organic compound layer is an emission layer.

6. The organic light-emitting device according to claim 5, wherein the emission layer comprises a host material and a guest material, and the host material comprises the chrysene compound.

7. The organic light-emitting device according to claim 4, which further comprises another layer different from the organic compound layer between the pair of electrodes, wherein the another layer is an emission layer, and the organic compound layer is an electron transport layer.

8. A display apparatus, comprising:
the organic light-emitting device set forth in claim 4; and
a switching device connected to the organic light-emitting device.

* * * * *